US011884972B2

(12) United States Patent
Wendt et al.

(10) Patent No.: US 11,884,972 B2
(45) Date of Patent: Jan. 30, 2024

(54) METHOD TO SCREEN FOR A MUTANT WITHIN A POPULATION OF ORGANISMS BY APPLYING A POOLING AND SPLITTING APPROACH

(71) Applicant: Carlsberg A/S, Copenhagen (DK)

(72) Inventors: Toni Wendt, Frederiksberg (DK); Ole Olsen, Copenhagen S (DK); Søren Knudsen, Malov (DK); Hanne Cecille Thomsen, Valby (DK); Birgitte Skadhauge, Birkerod (DK); Magnus Wohlfahrt Rasmussen, Copenhagen V (DK); Massimiliano Carciofi, Copenhagen (DK); Alexander Striebeck, Frederiksberg C (DK)

(73) Assignee: Carlsberg A/S, Copenhagen V (DK)

(*) Notice: Subject to any disclaimer, the term of this patent is extended or adjusted under 35 U.S.C. 154(b) by 500 days.

(21) Appl. No.: 16/311,450

(22) PCT Filed: Jun. 23, 2017

(86) PCT No.: PCT/EP2017/065516
§ 371 (c)(1),
(2) Date: Dec. 19, 2018

(87) PCT Pub. No.: WO2018/001884
PCT Pub. Date: Jan. 4, 2018

(65) Prior Publication Data
US 2019/0194723 A1    Jun. 27, 2019

(30) Foreign Application Priority Data

Jul. 1, 2016 (DK) ............................. PA201670485

(51) Int. Cl.
| | | |
|---|---|---|
| *C12Q 1/68* | (2018.01) | |
| *C12Q 1/686* | (2018.01) | |
| *C12N 15/01* | (2006.01) | |
| *C12N 15/10* | (2006.01) | |
| *A01H 6/46* | (2018.01) | |
| *C12Q 1/6806* | (2018.01) | |
| *C12Q 1/6827* | (2018.01) | |
| *C12Q 1/6876* | (2018.01) | |
| *C40B 30/00* | (2006.01) | |
| *C40B 40/02* | (2006.01) | |

(52) U.S. Cl.
CPC ............ *C12Q 1/686* (2013.01); *A01H 6/4624* (2018.05); *C12N 15/01* (2013.01); *C12N 15/1024* (2013.01); *C12Q 1/6806* (2013.01); *C12Q 1/6827* (2013.01); *C12Q 1/6876* (2013.01); *C40B 30/00* (2013.01); *C40B 40/02* (2013.01)

(58) Field of Classification Search
CPC .................................................. C40B 30/00
See application file for complete search history.

(56) References Cited

U.S. PATENT DOCUMENTS

| | | | |
|---|---|---|---|
| 7,622,280 B2 | 11/2009 | Holliger et al. | |
| 2005/0177901 A1* | 8/2005 | Zhu ...................... | C12Q 1/6895 |
| | | | 435/6.12 |

FOREIGN PATENT DOCUMENTS

| | | | | |
|---|---|---|---|---|
| JP | 2001507570 A | 6/2001 | | |
| JP | 2002510506 A | 4/2002 | | |
| WO | 1998023759 A2 | 6/1998 | | |
| WO | WO 98/55502 | 12/1998 | | |
| WO | 9951774 A2 | 10/1999 | | |
| WO | WO-03000905 A2 * | 1/2003 | ............ | C07K 14/415 |
| WO | WO 2010/036352 A1 | 4/2010 | | |
| WO | WO-2012122571 A1 * | 9/2012 | ............ | C12Q 1/6811 |
| WO | WO 2015/131101 A1 | 9/2015 | | |
| WO | 2016001736 A1 | 1/2016 | | |

OTHER PUBLICATIONS

Gilchrist, E.J., Sidebottom, C.H., Koh, C.S., MacInnes, T., Sharpe, A.G. and Haughn, G.W., 2013. A mutant *Brassica napus* (Canola) population for the identification of new genetic diversity via TILLING and next generation sequencing. PLoS One, 8(12), p.e84303. pp. 1-11. (Year: 2013).*

Knoll J, Ramos M, Zeng Y, Holbrook C, Chow M, Chen S, et al. TILLING for allergen reduction and improvement of quality traits in peanut (*Arachis hypogaea* L.). BMC Plant Biol. 2011;11:81. (Year: 2011).*

Tsai H, Howell T, Nitcher R, Missirian V, Watson B, Ngo K, et al. Discovery of rare mutations in populations: TILLING by sequencing. Plant Physiol. 2011;156(3):1257-68. (Year: 2011).*

Wang, N., Wang, Y., Tian, F., King, G.J., Zhang, C., Long, Y., Shi, L. and Meng, J., 2008. A functional genomics resource for *Brassica napus*: development of an EMS mutagenized population and discovery of FAE1 point mutations by TILLING. New Phytologist, 180(4), pp. 751-765. (Year: 2008).*

Zhu, Q., Smith, S.M., Ayele, M., Yang, L., Jogi, A., Chaluvadi, S.R. and Bennetzen, J.L., 2012. High-throughput discovery of mutations in tef semi-dwarfing genes by next-generation sequencing analysis. Genetics, 192(3), pp. 819-829. (Year: 2012).*

(Continued)

*Primary Examiner* — Teresa E Strzelecka
*Assistant Examiner* — Olayinka A Oyeyemi
(74) *Attorney, Agent, or Firm* — McNeill Baur PLLC

(57) ABSTRACT

In traditional plant breeding approaches, chemical mutagenesis may be utilized to introduce nucleotide substitutions at random in the genome of a plant, i.e. without possibilities to control the sites of nucleotide changes. Because of genome complexities, the statistical probability is extremely little when it comes to finding a predetermined nucleotide substitution. The present invention, however, demonstrates how a novel, alternative use of digital polymerase chain reaction (dPCR), preferably droplet dPCR (ddPCR), is developed to exploit finding of specific nucleotide substitutions in mutated genes. The entire platform comprises a screening method with a library of mutagenized organisms, digital PCR-based systems and a set-up to propagate and analyze identified, mutated organisms.

22 Claims, 8 Drawing Sheets
Specification includes a Sequence Listing.

(56) References Cited

OTHER PUBLICATIONS

Goldman, J.J., 2006. High-Throughput DNA Extraction and Allele Specific PCR Primers Enables Efficient Screening for Mutant (gsf) and Wild-Type (GSF) Alleles in Eastern Gamagrass. Crop science, 46(1), pp. 362-364. (Year: 2006).*
Galbiati, M., Moreno, M.A., Nadzan, G., Zourelidou, M. and Dellaporta, S.L., 2000. Large-scale T-DNA mutagenesis in *Arabidopsis* for functional genomic analysis. Functional & integrative genomics, 1(1), pp. 25-34. (Year: 2000).*
Gao, S., Martinez, C., Skinner, D.J., Krivanek, A.F., Crouch, J.H. and Xu, Y., 2008. Development of a seed DNA-based genotyping system for marker-assisted selection in maize. Molecular Breeding, 22(3), pp. 477-494. (Year: 2008).*
Sham, P., Bader, U.S., Craig, I., O'Donovan, M. and Owen, M., 2002. DNA pooling: a tool for large-scale association studies. Nature Reviews Genetics, 3(11), pp. 862-871. (Year: 2002).*
Głowacka, K., Kromdijk, J., Leonelli, L., Niyogi, K.K., Clemente, T.E. and Long, S.P., Epub Jan. 21, 2016. An evaluation of new and established methods to determine T-DNA copy number and homozygosity in transgenic plants. Plant, cell & environment, 39(4), pp. 908-917. (Year: 2016).*
Yang, R.F., Li, W.C., He, J., Zhou, S.F., She, Y.H. and Fu, F.L., 2011. Inducement and identification of an endosperm mutant in maize. African Journal of Biotechnology, 10(76), pp. 17490-17498. (Year: 2011).*
Khan, S., Al-Qurainy, F. and Anwar, F., 2009. Sodium azide: a chemical mutagen for enhancement of agronomic traits of crop plants. Environ. We Int. J. Sci. Tech, 4, pp. 1-21. (Year: 2009).*
He, Y.L., Gao, H.H., Ye, L.Y., Guo, Z.H., Wang, P. and Zhu, Z.Y., 2013. Multiplex polymerase chain reaction with DNA pooling: a cost-effective strategy of genotyping rare blood types. Transfusion Medicine, 23(1), pp. 42-47. (Year: 2013).*
Głowacka et al., Epub Jan. 21, 2016. Supporting Information, ddPCR protocol. Plant, cell & environment, 39(4), pp. 908-917. (Year: 2016).*
Głowacka et al., Epub Jan. 21, 2016. Supporting Information, PRIMERS. Plant, cell & environment, 39(4), pp. 908-917. (Year: 2016).*
Cobb, J.N., DeClerck, G., Greenberg, A., Clark, R. and McCouch, S., 2013. Next-generation phenotyping: requirements and strategies for enhancing our understanding of genotype-phenotype relationships and its relevance to crop improvement. Theoretical and Applied Genetics, 126(4), pp. 867-887. (Year: 2013).*
Collard, B.C., Cruz, C.M.V., McNally, K.L., Virk, P.S. and Mackill, D.J., 2008. Rice molecular breeding laboratories in the genomics era: current status and future considerations. International journal of plant genomics, pp. 1-25. (Year: 2008).*
Balyan et al., 2008. Mutagenesis and High-Throughput Functional Genomics in Cereal Crops: Current Status. Advances in Agronomy, 98, pp. 357-414. (Year: 2008).*
Li et al., 2001. A fast neutron deletion mutagenesis-based reverse genetics system for plants. The Plant Journal, 27(3), pp. 235-242. (Year: 2001).*
Li, X. and Zhang, Y., 2002. Reverse genetics by fast neutron mutagenesis in higher plants. Functional & integrative genomics, 2, pp. 254-258. (Year: 2002).*
McCallum et al., 2000. Targeted screening for induced mutations. Nature biotechnology, 18(4), pp. 455-457. (Year: 2000).*
Pham et al., 2014. Characterization of the fan1 locus in soybean line A5 and development of molecular assays for high-throughput genotyping of FAD3 genes. Molecular breeding, 33, pp. 895-907. (Year: 2014).*
Sussman et al., 2000. The *Arabidopsis* knockout facility at the University of Wisconsin-Madison. Plant Physiology, 124(4), pp. 1465-1467. (Year: 2000).*
Telgmann-Rauber et al., 2007. Genetic and physical maps around the sex-determining M-locus of the dioecious plant asparagus. Molecular Genetics and Genomics, 278, pp. 221-234. (Year: 2007).*

Baker et al, Digital PCR hits its stride, Nature Methods, vol. 9, No. 6, Jun. 2012, p. 541-544.
Botticella et al., High resolution melting analysis for the detection of EMS induced mutations in wheat Sbella genes, BMC Plant Biology, 11:156, 2011.
Stemberger et al, "Novel Serial Positive Enrichment Technology Enables Clinical Multiparameter Cell Sorting", vol. 7 No. 4, Apr. 24, 2012 p. e35798.
Goodyear et al, "Phage-Display Methodology for the Study of Protein-Protein Interaction: Overview", Cold Spring Harbor Protocol, vol. 2008, No. 9, Aug. 1, 2008.
Guo et al., TILLING by sequencing to identify induced mutations in stress resistance genes of peanut (*Arachis hypogaea*), BMC Genomics, 16:157, 2015.
Hindson et al, High-Throughput Droplet Digital PCR System for Absolute Quantitation of DNA Copy Number, Analytical Chemistry, 2011, 83, p. 8604-8610.
Slightom, et al., "Cloning and molecular characterization of the gene encoding the aureobasidin A biosynthesis complex in Aureobasidium pullulans BP-1938", Gene Elsevier, vol. 431, No. 1-2, Feb. 15, 2009.
Jacobs, "Making mitochondrial mutants", Trends in genetics, Elsevier Science Publ., vol. 17, No. 11, Nov. 1, 2001, p. 653-660.
Jiang et al., Structures of a CRISPR-Cas9 R-loop complex primed for DNA cleavage, Science, vol. 351, Issue 6275, 2016.
Brunden et al., "Planning the purification process of active cDNA in expression cloning strategies", Journal of Theoretical Biology, vol. 144, No. 2, May 22, 1990.
Miyaoka et al, "Isolation of single-base genome-edited human iPS cells without antibiotic selection", Nature Methods, vol. 11, No. 3, Mar. 2014, p. 291-298.
Pleasance et al, A comprehensive catalogue of somatic mutations from a human cancer genome, Nature; 463(7278): 191-196, 2010.
Rigola et al, High-Throughput Detection of Induced Mutations and Natural Vairation Using KeyPoint Technology, Plos One, Mar. 2009, vol. 4, Issue 3, p. 1-9.
Grimm, "The art and design of genetic screens: Mammalian culture cells", Nature Review Genetics, vol. 5, No. 3, Mar. 1, 2004 (Mar. 1, 2004), p. 179-189.
Schuster-Böchler et al. (2012), Chromatin organization is a major influence on regional mutation rates in uman cancer cells. Nature 488: 504-507.
Yamaya et al., Evidence supporting distinct functions of three cytosolic glutamine synthetases and two NADH-glutamate synthases in rice, Journal of Experimental Botany, vol. 65, No. 19, pp. 5519-5525, 2014.
Goldman, Jason J., "High-Throughput DNA Extraction and Allele Specific PCR Primers Enables Efficient Screening for Mutant (gsf) and Wild-Type (GSF) Alleles in Eastern Gamagrass", Crop Science, 2006, vol. 46, pp. 362-364.
He, Y. L., et al., "Multiplex polymerase chain reaction with DNA pooling: a cost-effective strategy of genotyping rare blood types", Transfusion Medicine, 2013, vol. 23, pp. 42-47.
Zhang, J., et al., "An optimal pooling strategy applied to high-throughput screening for rare marker-free transformants", Biotechnology Letters, 2006, vol. 28, pp. 1537-1544.
Chi, X., et al. "Discovery of rare mutations in extensively pooled DNA samples using multiple target enrichment," Plant Biotechnology Journal, vol. 12, pp. 709-717 (2014).
Hohjog, H., "Digital PCR Revolution," Experimental Medicine, vol. 34, No. 8, 2016.
https://www.thermofisher.com/blog/learning-at-the-bench/digitalpcr1/.
A capture of a webpage available at https://www.carlsbergfondet.dk/en/News/News-from-the-Foundation/News/FIND-IT_Carlsberg-Research-Laboratory-develops-ultrafast-crop-improvement-technology published Aug. 26, 2022, retrieved Aug. 30, 2022.
A capture of a webpage available at https://www.science.org/toc/sciadv/8/34 retrieved Aug. 30, 2022.
A capture of relevant portions of a website of Traitomic (https://traitomic.com) retrieved Aug. 30, 2022.

(56) References Cited

OTHER PUBLICATIONS

A statement of Dr. Brande Wulff obtained from his Twitter post of May 23, 2021, available at https://twitter.com/BrandeWulff/status/1396533000616169481?s=20&t=tWr8IDTbrRhccZZz7OKA, retrieved on Jul. 27, 2022.

Knudsen et al., "FIND-IT: Accelerated trait development for a green evolution," Sci. Adv. 8, eabq2266 (2022), pp. 1-16 and Supplementary Materials (https://doi.org/10.1126/sciadv.abq2266).

Knudsen, S., et al., "FIND-IT: Ultrafast mining of genome diversity," bioRxiv, May 20, 2021.

Lopez-Marques, R., et al. "Prospects for the accelerated improvement of the resilient crop quinoa," Journal of Experimental Botany, vol. 71, No. 18, pp. 5333-5347 (2020).

Luo, G., et al., "Accelerated Domestication of New Crops: Yield is Key," Plant and Cell Physiology, pp. 1-17 (2022).

Kysan, P.J., et al., "Identification of transferred DNA insertions within *Arabidopsis* genes involved in signal transduction and ion transport," PNAS, vol. 93, pp. 8145-8150 (1996).

\* cited by examiner

SEQUENCE LISTING

```
<160> NUMBER OF SEQ ID NOS: 26

<210> SEQ ID NO 1
<211> LENGTH: 1089
<212> TYPE: DNA
<213> ORGANISM: Hordeum vulgare

<400> SEQUENCE: 1
atgtctcggc tcgccgacct tctcagcctc gacctgtccg gctgcaccgg caagatcatc      60
gccgagtaca tatgggtcgg cggcaccggg atggacgtca ggagcaaagc caggacgctt     120
cccggacccg tggacgaccc cagcaagctt ccaaagtgga atttcgacgg ctccagcacc     180
ggccaagcca cgggcgacga cagcgaagtc atcctccgac cccaagccat cttcagggac     240
ccgttcagga aagggaacaa catcctggtc atctgtgact gctatgcgcc taccggagag     300
ccgattccga gcaacaagcg gtacaacgcg gcgaggatat tcggccatcc tgatgtcaag     360
tctgaagaac catggtatgg gattgagcag gagtacaccc ttctccagaa ggacaccaac     420
tggcccattg gctggccact aggggttac cctggccctc aggggcctta ctactgcgcc      480
gcgggtgcgg agaaatctta cggcgcgac atcgtcgacg cccactacaa ggcctgcctc     540
tacgccggca tcaacatcgg cggcatcaat gcagaagtca tgccagggca gtgggagttc     600
caagtcggcc cttccgtcgg yatctccgcc ggcgacgagc tctgggcggc tcgctacatt     660
ctcgagagga tcactgagat cgccggcgtc gtcgtctcct tcgaccccaa accgatcccg     720
ggagagtgga acggtgccgg tgcccacaca aactacagca ccaagtcgat gaggagcgag     780
ggcgggtacg aggtgatcaa gagggcgatc aagaagctcg aggcgcggca cacggagcac     840
```

-continued

```
atagccgcct acggggaagg caacgagcgc cggctcaccg gccgccacga gaccgccgac      900
atcaacacct tcgtatgggg cgtggcaaac cgcggcgcgt cggtgcgggt ggggcgcgac      960
accgagaagg aaggcagggg ctacttcgag gaccggaggc cggcgtccaa catggatccc     1020
tacgtcgtca cctccatgat cgccgagacc accatcctct ggaaggccgg tctctccaat     1080
ggcaagtag                                                             1089
```

```
<210> SEQ ID NO 2
<211> LENGTH: 362
<212> TYPE: PRT
<213> ORGANISM: Hordeum vulgare

<400> SEQUENCE: 2
```

Met Ser Arg Leu Ala Asp Leu Leu Ser Leu Asp Leu Ser Gly Cys Thr
1               5                   10                  15

Gly Lys Ile Ile Ala Glu Tyr Ile Trp Val Gly Gly Thr Gly Met Asp
            20                  25                  30

Val Arg Ser Lys Ala Arg Thr Leu Pro Gly Pro Val Asp Asp Pro Ser
        35                  40                  45

Lys Leu Pro Lys Trp Asn Phe Asp Gly Ser Ser Thr Gly Gln Ala Thr
    50                  55                  60

Gly Asp Asp Ser Glu Val Ile Leu Arg Pro Gln Ala Ile Phe Arg Asp
65                  70                  75                  80

Pro Phe Arg Lys Gly Asn Asn Ile Leu Val Ile Cys Asp Cys Tyr Ala
                85                  90                  95

Pro Thr Gly Glu Pro Ile Pro Ser Asn Lys Arg Tyr Asn Ala Ala Arg
            100                 105                 110

Ile Phe Gly His Pro Asp Val Lys Ser Glu Glu Pro Trp Tyr Gly Ile
        115                 120                 125

Glu Gln Glu Tyr Thr Leu Leu Gln Lys Asp Thr Asn Trp Pro Ile Gly
    130                 135                 140

Trp Pro Leu Gly Gly Tyr Pro Gly Pro Gln Gly Pro Tyr Tyr Cys Ala
145                 150                 155                 160

Ala Gly Ala Glu Lys Ser Tyr Gly Arg Asp Ile Val Asp Ala His Tyr
                165                 170                 175

Lys Ala Cys Leu Tyr Ala Gly Ile Asn Ile Gly Gly Ile Asn Ala Glu
            180                 185                 190

Val Met Pro Gly Gln Trp Glu Phe Gln Val Gly Pro Ser Val Gly Ile
        195                 200                 205

Ser Ala Gly Asp Glu Leu Trp Ala Ala Arg Tyr Ile Leu Glu Arg Ile
    210                 215                 220

Thr Glu Ile Ala Gly Val Val Val Ser Phe Asp Pro Lys Pro Ile Pro
225                 230                 235                 240

Gly Glu Trp Asn Gly Ala Gly Ala His Thr Asn Tyr Ser Thr Lys Ser
                245                 250                 255

Met Arg Ser Glu Gly Gly Tyr Glu Val Ile Lys Arg Ala Ile Lys Lys
            260                 265                 270

Leu Glu Ala Arg His Thr Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Val Trp Gly Val Ala Asn Arg Gly Ala Ser Val Arg Val Gly Arg Asp
305                 310                 315                 320

Thr Glu Lys Glu Gly Arg Gly Tyr Phe Glu Asp Arg Arg Pro Ala Ser

```
                    325                 330                 335
Asn Met Asp Pro Tyr Val Val Thr Ser Met Ile Ala Glu Thr Thr Ile
            340                 345                 350

Leu Trp Lys Ala Gly Leu Ser Asn Gly Lys
            355                 360

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
gtgatcaaga gggcgatcaa                                                   20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
caagtctcaa ctcgccgtat                                                   20

<210> SEQ ID NO 5
<211> LENGTH: 14
<212> TYPE: DNA
<213> ORGANISM: Artificial sequence
<220> FEATURE:
<223> OTHER INFORMATION: Probe

<400> SEQUENCE: 5
aagacaacga gcgc                                                         14

<210> SEQ ID NO 6
<211> LENGTH: 14
<212> TYPE: DNA
<213> ORGANISM: Artificial sequence
<220> FEATURE:
<223> OTHER INFORMATION: Probe

<400> SEQUENCE: 6
aaggcaacga gcgc                                                         14

<210> SEQ ID NO 7
<211> LENGTH: 503
<212> TYPE: PRT
<213> ORGANISM: Saccharomyces cerevisiae

<400> SEQUENCE: 7

Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
            35                  40                  45

Pro Ala Pro Leu Phe Lys Asn Leu Lys Gly Ala Ser Lys Asp Leu Phe
        50                  55                  60

Ser Ile Leu Gly Cys Pro Ala Gly Leu Arg Ser Lys Glu Lys Gly Asp
65                  70                  75                  80
```

```
His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
            115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
            195                 200                 205

Glu Ile Pro Phe Ala Leu Cys Phe Gly Val Pro Ala Ala Ile Leu
210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
            245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
            275                 280                 285

Tyr Val Phe Lys Ser Gln Gly His Pro Cys Pro Leu Tyr Thr Val Lys
290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
            325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
            370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
            435                 440                 445

Ser Ser Arg Ser Lys Thr Met Lys Gly Gly Lys Cys Val Thr Asn Cys
450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
```

-continued

```
                500

<210> SEQ ID NO 8
<211> LENGTH: 101
<212> TYPE: PRT
<213> ORGANISM: Triticum aestivum

<400> SEQUENCE: 8

Met Ala Lys Ile Ser Phe Leu Leu Val Ala Leu Val Leu Ala Val
1               5                   10                  15

Gly Phe Pro Val Glu Val Met Gly Gly Gly Gly Gly Gly Gly
                20                  25                  30

Gly Gly Gly Gly Asn Leu Lys Pro Trp Glu Cys Ser Lys Cys Ser
                35                  40                  45

Ser Arg Cys Ser Gly Thr Gln Tyr Lys Lys Ala Cys Leu Thr Tyr Cys
    50                  55                  60

Asn Lys Cys Cys Ala Thr Cys Leu Cys Val Pro Pro Gly Thr Tyr Gly
65              70                  75                  80

Asn Lys Gly Ala Cys Pro Cys Tyr Asn Asn Trp Lys Thr Lys Glu Gly
                85                  90                  95

Gly Pro Lys Cys Pro
            100

<210> SEQ ID NO 9
<211> LENGTH: 15
<212> TYPE: DNA
<213> ORGANISM: Artificial sequence
<220> FEATURE:
<223> OTHER INFORMATION: Primer

<400> SEQUENCE: 9
cgcctgcccc tgcta                                                   15

<210> SEQ ID NO 10
<211> LENGTH: 31
<212> TYPE: DNA
<213> ORGANISM: Artificial sequence
<220> FEATURE:
<223> OTHER INFORMATION: Primer

<400> SEQUENCE: 10
agaagaagaa gaagaagaag aaaaccaaga a                                 31

<210> SEQ ID NO 11
<211> LENGTH: 17
<212> TYPE: DNA
<213> ORGANISM: Artificial sequence
<220> FEATURE:
<223> OTHER INFORMATION: Probe

<400> SEQUENCE: 11
caacaactga aagacca                                                 17

<210> SEQ ID NO 12
<211> LENGTH: 17
<212> TYPE: DNA
<213> ORGANISM: Artificial sequence
<220> FEATURE:
<223> OTHER INFORMATION: Probe

<400> SEQUENCE: 12
caacaactgg aagacca                                                 17
```

-continued

<210> SEQ ID NO 13
<211> LENGTH: 17
<212> TYPE: DNA
<213> ORGANISM: Artificial sequence
<220> FEATURE:
<223> OTHER INFORMATION: Primer

<400> SEQUENCE: 13
catgtttcag acggtgg                                                          17

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
catacctcta gcaattgacc                                                       20

<210> SEQ ID NO 15
<211> LENGTH: 20
<212> TYPE: DNA
<213> ORGANISM: Artificial sequence
<220> FEATURE:
<223> OTHER INFORMATION: Probe

<400> SEQUENCE: 15
acgtacggaa tgtagattct                                                       20

<210> SEQ ID NO 16
<211> LENGTH: 18
<212> TYPE: DNA
<213> ORGANISM: Artificial sequence
<220> FEATURE:
<223> OTHER INFORMATION: Probe

<400> SEQUENCE: 16
acgtacggaa tgtggatt                                                         18

<210> SEQ ID NO 17
<211> LENGTH: 1260
<212> TYPE: DNA
<213> ORGANISM: Hordeum vulgare

<400> SEQUENCE: 17
atggcgtcgt cgagcttcaa ggtgacgcgg atctcggagg gcgcggtgaa gccggcgtcg           60
gagacgcccg accacacgct gccgctggcg tgggtggacc ggtacccgac ccaccgcggc          120
ctggtggagt cgatgcacat cttccggtcc ggcgccgacg cggccccggg cgtgatccgc          180
gaggcgctgg gcaaggcgct ggccttcttc tacccgctgg cggggcgcat cgtggagcag          240
ccggagaagg ggtgccccgc catccgctgc accgccgacg gcgtctactt cgcggaggcc          300
gtcgccgagt gcagcctgga ggacgtccgg ttcctggagc gcccccctgct gctccccaag          360 gaggacctcg tccctaccc cgccgccgat ctctgggccg tcgagcccca caacaccatc           420
atgatgatgc agatcacgaa attcacatgc ggcgggttcg tgatgggcct ccggttcaac          480
cacgcgtcgg cggacggcat gggcgcggcg cagttcatca aggcggtcgg cgacatggcc          540
cgggggctcc cggagccgac ggtgaagccg gtgtgggaca gggagaagtt ccccaacccg          600
agcatcaagc cggccctct cccggagctc ccggtgctgg cgctggacta catcgtgctc           660
gacttcccca cgggctacat cgacgggctc aagacgcagt acaaggcgca cagcggcaag          720

```
ttctgctccg gcttcgacgt gctgacggcc aagctgtggc agtgccgtac ccgggcgctg      780
aacctggagc cggacgccac ggtgaagctg tgcttcttcg ccagcgtgcg ccacctgctg      840
aagctggacg ccgggtacta cggcaactcc atcttccccg tgaagatgtc cgggacgagc      900
aagaaggtgc tggagtcgtc ggtgatggag gtgatcgaca tgatccggga ggccaagcag      960
cggatggcgg tggagttctt ccagttcgcc aaggaggaga cgcggcagga ccccttccag     1020
atgaccttcg actacgagtc catctacgtc tccgactgga gcaagctggg gttctccgac     1080
gtggactacg gcttcggccc gcccatgttc gccggaccgc tcgtcaacaa cgacttcatc     1140
gcctccgtcg tcatcctcaa ggcgccgctg ccgctggacg gcaccaggat gctcgccagc     1200
tgcgtcacca aggagcactc gcaggagttc gcccgcggca tgaaggagga cctgccatga     1260
```

<210> SEQ ID NO 18
<211> LENGTH: 1260
<212> TYPE: DNA
<213> ORGANISM: Artificial sequence
<220> FEATURE:
<223> OTHER INFORMATION: Mutant cDNA

<400> SEQUENCE: 18

```
atggcgtcgt cgagcttcaa ggtgacgcgg atctcggagg gcgcggtgaa gccggcgtcg       60
gagacgcccg accacacgct gccgctggcg tgagtggacc ggtacccgac ccaccgcggc      120
ctggtggagt cgatgcacat cttccggtcc ggcgccgacg cggcccccgg cgtgatccgc      180
gaggcgctgg gcaaggcgct ggccttcttc tacccgctgg cggggcgcat cgtggagcag      240
ccggagaagg ggtgccccgc catccgctgc accgccgacg gcgtctactt cgcggaggcc      300
gtcgccgagt gcagcctgga ggacgtccgg ttcctggagc gccccctgct gctccccaag      360
gaggacctcg tccctaccc cgccgccgat ctctgggccg tcgagcccca caacaccatc      420
atgatgatgc agatcacgaa attcacatgc ggcgggttcg tgatgggcct ccggttcaac      480
cacgcgtcgg cggacggcat gggcgcggcg cagttcatca aggcggtcgg cgacatggcc      540 cggggggctcc cggagccgac ggtgaagccg gtgtgggaca gggagaagtt ccccaacccg      600
agcatcaagc cgggccctct cccggagctc ccggtgctgg cgctggacta catcgtgctc      660
gacttcccca cgggctacat cgacgggctc aagacgcagt acaaggcgca cagcggcaag      720
ttctgctccg gcttcgacgt gctgacggcc aagctgtggc agtgccgtac ccgggcgctg      780
aacctggagc cggacgccac ggtgaagctg tgcttcttcg ccagcgtgcg ccacctgctg      840
aagctggacg ccgggtacta cggcaactcc atcttccccg tgaagatgtc cgggacgagc      900
aagaaggtgc tggagtcgtc ggtgatggag gtgatcgaca tgatccggga ggccaagcag      960
cggatggcgg tggagttctt ccagttcgcc aaggaggaga cgcggcagga ccccttccag     1020
atgaccttcg actacgagtc catctacgtc tccgactgga gcaagctggg gttctccgac     1080
gtggactacg gcttcggccc gcccatgttc gccggaccgc tcgtcaacaa cgacttcatc     1140
gcctccgtcg tcatcctcaa ggcgccgctg ccgctggacg gcaccaggat gctcgccagc     1200
tgcgtcacca aggagcactc gcaggagttc gcccgcggca tgaaggagga cctgccatga     1260
```

<210> SEQ ID NO 19
<211> LENGTH: 419
<212> TYPE: PRT
<213> ORGANISM: Hordeum vulgare

<400> SEQUENCE: 19

-continued

```
Met Ala Ser Ser Ser Phe Lys Val Thr Arg Ile Ser Glu Gly Ala Val
1               5                   10                  15

Lys Pro Ala Ser Glu Thr Pro Asp His Thr Leu Pro Leu Ala Trp Val
            20                  25                  30

Asp Arg Tyr Pro Thr His Arg Gly Leu Val Glu Ser Met His Ile Phe
        35                  40                  45

Arg Ser Gly Ala Asp Ala Ala Pro Gly Val Ile Arg Glu Ala Leu Gly
    50                  55                  60

Lys Ala Leu Ala Phe Phe Tyr Pro Leu Ala Gly Arg Ile Val Glu Gln
65                  70                  75                  80

Pro Glu Lys Gly Cys Pro Ala Ile Arg Cys Thr Ala Asp Gly Val Tyr
                85                  90                  95

Phe Ala Glu Ala Val Ala Glu Cys Ser Leu Glu Asp Val Arg Phe Leu
            100                 105                 110

Glu Arg Pro Leu Leu Leu Pro Lys Glu Asp Leu Val Pro Tyr Pro Ala
        115                 120                 125

Ala Asp Leu Trp Ala Val Glu Pro His Asn Thr Ile Met Met Met Gln
130                 135                 140

Ile Thr Lys Phe Thr Cys Gly Gly Phe Val Met Gly Leu Arg Phe Asn
145                 150                 155                 160

His Ala Ser Ala Asp Gly Met Gly Ala Ala Gln Phe Ile Lys Ala Val
                165                 170                 175

Gly Asp Met Ala Arg Gly Leu Pro Glu Pro Thr Val Lys Pro Val Trp
            180                 185                 190

Asp Arg Glu Lys Phe Pro Asn Pro Ser Ile Lys Pro Gly Pro Leu Pro
        195                 200                 205

Glu Leu Pro Val Leu Ala Leu Asp Tyr Ile Val Leu Asp Phe Pro Thr
    210                 215                 220

Gly Tyr Ile Asp Gly Leu Lys Thr Gln Tyr Lys Ala His Ser Gly Lys
225                 230                 235                 240

Phe Cys Ser Gly Phe Asp Val Leu Thr Ala Lys Leu Trp Gln Cys Arg
                245                 250                 255

Thr Arg Ala Leu Asn Leu Glu Pro Asp Ala Thr Val Lys Leu Cys Phe
            260                 265                 270

Phe Ala Ser Val Arg His Leu Leu Lys Leu Asp Ala Gly Tyr Tyr Gly
        275                 280                 285

Asn Ser Ile Phe Pro Val Lys Met Ser Gly Thr Ser Lys Lys Val Leu
    290                 295                 300

Glu Ser Ser Val Met Glu Val Ile Asp Met Ile Arg Glu Ala Lys Gln
305                 310                 315                 320

Arg Met Ala Val Glu Phe Phe Gln Phe Ala Lys Glu Glu Thr Arg Gln
                325                 330                 335

Asp Pro Phe Gln Met Thr Phe Asp Tyr Glu Ser Ile Tyr Val Ser Asp
            340                 345                 350

Trp Ser Lys Leu Gly Phe Ser Asp Val Asp Tyr Gly Phe Gly Pro Pro
        355                 360                 365

Met Phe Ala Gly Pro Leu Val Asn Asn Asp Phe Ile Ala Ser Val Val
    370                 375                 380

Ile Leu Lys Ala Pro Leu Pro Leu Asp Gly Thr Arg Met Leu Ala Ser
385                 390                 395                 400

Cys Val Thr Lys Glu His Ser Gln Glu Phe Ala Arg Gly Met Lys Glu
                405                 410                 415

Asp Leu Pro
```

```
<210> SEQ ID NO 20
<211> LENGTH: 13
<212> TYPE: DNA
<213> ORGANISM: Artificial sequence
<220> FEATURE:
<223> OTHER INFORMATION: Primer

<400> SEQUENCE: 20
cccgaccaca cgc                                                       13

<210> SEQ ID NO 21
<211> LENGTH: 14
<212> TYPE: DNA
<213> ORGANISM: Artificial sequence
<220> FEATURE:
<223> OTHER INFORMATION: Primer

<400> SEQUENCE: 21
actccaccag gccg                                                      14

<210> SEQ ID NO 22
<211> LENGTH: 15
<212> TYPE: DNA
<213> ORGANISM: Artificial sequence
<220> FEATURE:
<223> OTHER INFORMATION: Probe

<400> SEQUENCE: 22
ctggcgtgag tggac                                                     15

<210> SEQ ID NO 23
<211> LENGTH: 14
<212> TYPE: DNA
<213> ORGANISM: Artificial sequence
<220> FEATURE:
<223> OTHER INFORMATION: Probe

<400> SEQUENCE: 23
ctggcgtggg tgga                                                      14

<210> SEQ ID NO 24
<211> LENGTH: 14
<212> TYPE: DNA
<213> ORGANISM: Artificial sequence
<220> FEATURE:
<223> OTHER INFORMATION: Probe

<400> SEQUENCE: 24
ctggcgtggg tgga                                                      14

<210> SEQ ID NO 25
<211> LENGTH: 306
<212> TYPE: DNA
<213> ORGANISM: Triticum aestivum

<400> SEQUENCE: 25
atggccaaga tctccttcct cctcgtggcg ctcctcgtcc tcgccgtcgg gttccccgtg     60
gaggtgatgg gaggtggggg cggcggcggc ggtggcggtg gcggcggcaa cctcaagcca    120
tgggagtgct cgtccaagtg ctcgtcgcgg tgctcgggga cgcagtacaa gaaggcgtgc    180
ctgacctact gcaacaagtg ctgcgccacc tgctctctgcg tgccgccggg cacctacggc    240
aacaagggcg cctgccccctg ctacaacaac tggaagacca aggagggagg ccccaagtgc    300
```

```
ccctag                                                                  306

<210> SEQ ID NO 26
<211> LENGTH: 1512
<212> TYPE: DNA
<213> ORGANISM: Saccharomyces cerevisiae

<400> SEQUENCE: 26
atgaggaagc taaatccagc tttagaattt agagactttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga gaagtaagga gaaaggagat     240
catggtagaa ttgcccatca tctgggctc gacccaaaaa caactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct tgggtgagtc ggttccagta gtaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgcctta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa aagttggttt tatagtccat    1200 gaaataatttt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                         1512
```

METHOD TO SCREEN FOR A MUTANT WITHIN A POPULATION OF ORGANISMS BY APPLYING A POOLING AND SPLITTING APPROACH

CROSS-REFERENCE TO RELATED APPLICATIONS

This application is a national phase entry pursuant to 35 U.S.C. § 371 of International Application No. PCT/EP2017/065516, filed Jun. 23, 2017, which claims the benefit of priority of Denmark Application No. PA 2016 70485, filed Jul. 1, 2016, each of which is incorporated by reference herein in its entirety for any purpose.

SEQUENCE LISTING

The present application is filed with a Sequence Listing in electronic format. The Sequence Listing is provided as a file entitled "2018-12-19_01130-0012-00US_Sequence_Listing.txt" created on Dec. 19, 2018, which is 22,974 bytes in size. The information in the electronic format of the sequence listing is incorporated herein by reference in its entirety.

FIELD OF THE INVENTION

The present invention provides highly accelerated methods and processes that make it practically possible to expand and tackle the preparation, selection and/or propagation of an organism with specific, predetermined mutation(s) in one or more nucleotides of interest (NOI). The methods of the invention are, for example, useful to advance the tempo and capacity of preparing plants with specific, predetermined mutation(s) in one or more NOI(s).

BACKGROUND OF THE INVENTION

Genetic methods to generate genetically modified (GM) organisms (GMOs) are widely available. However, for many purposes, particularly in the food and beverage industries, use of GMOs is often less desirable. Thus, there remains an enduring need to provide improved and more precise methods for traditional breeding of crops, including cereals such as barley, simply to obtain better, bespoke raw materials for application in the development and manufacture of new products. Similar shortcomings exist in relation to other organisms, including microorganisms and animals. There has, unfortunately, been a nagging lack of methods in traditional breeding approaches to address the finding of mutations at predefined nucleotides of genomes, thus limiting the progress of raw material development.

Methods are available to allow genome editing and introduction of double-stranded DNA breaks at targeted sites in an organism's genome, e.g. by CRISPR-Cas9 technology (Jiang et al., 2016). Two distinct, major complications remain associated with the CRISPR-Cas9 technology:

Firstly, CRISPR-Cas9 technology may be regarded as GM-based. Thus, basic legislative information is missing on how authorities aim to regulate the new genetic tools on genome editing, including introduction of double-stranded DNA breaks at targeted sites in the genome;

Secondly, there are major complications related to off-target cleavages with CRISPR-Cas9 technology.

Germline mutations in a natural context, e.g. those leading to phenotypic consequences in organisms, represent both the principal cause of heritable trait variation and the ultimate source of evolutionary change by virtue of advantageous or disruptive effects at the molecular level. Mutations arise in response to a number of factors, including:

Replication errors;

DNA damage, either repaired incorrectly or left unrepaired;

DNA damage caused by exogenous factors—such as chemicals, ultraviolet light, and ionizing radiation;

Endogenous factors, e.g. reactive oxygen species, aldehydes, or mitotic errors;

Enzymes involved in DNA repair or genome editing;

Viruses and endogenous retrotransposons that insert DNA fragments.

In addition, the current understanding is that exposure to a mutagen may induce numerous somatic gene mutations, the majority of which without noticeable selective advantage, but some may alter key cellular functions. Further, some genome-related properties are likely to be non-mutational, for instance epigenetic changes and alterations in the cellular microenvironment.

Traditional breeding of crops has involved random mutagenesis followed by screening for a desired trait. Unfortunately, there is a lack of efficient screening methods to identify predetermined gene changes, i.e. specific nucleotide substitutions in genes or regulatory elements of mutagenized organisms, e.g. cereals without employment of GM-based methods. Indeed, GM plants have experienced a >10-year-long competitive advantage concerning directed approaches on trait development per se and adoption by the wider scientific community. However, as mentioned above, GM-based methods may be less preferable.

Results of the recently developed genome sequencing technology revolutionized the understanding of the genetic architecture of traits (and corresponding changes in response to mutagenesis). There is, for instance, widespread expectance that whole-genome sequencing and novel computational methods, aided by large high-throughput gDNA sequencing efforts, will help answer several basic biological questions and speed up mutant characterization, e.g. using the monocotyledonous cereal plant barley.

In eukaryotes, it seems that some mutation processes show considerable variation in genomic distribution (Pleasance et al., 2010; Schuster-Böchler and Lehner, 2012). The number of point mutations varies along the genome and are typically higher in sequence regions of low gene expression levels, repressed chromatin and late replication times. Some of this variation may be driven by reduced access of the mismatch repair machinery to closed chromatin regions.

Given the background information provided above, those skilled in the field of cereal research will know that the analytical advances have placed barley and cereal research on the threshold of new frontiers, specifically in the R&D interphase between deep molecular biology-based understanding and industrial application of plants with new characteristics. That said, despite advances in genome sequencing technologies for mutant identification, such methods still remain time-consuming and logistically challenging, and stand little useful for the identification of specific predetermined mutations.

Two additional properties remain of interest, not only with respect to the identification of plants with predetermined mutations, but also to harness improvements:

Delimitation of the extent of germline and somatic mutation rates in cereals.

Current approaches focus on the narrow-down of mutant-finding to gDNA fragments based on context-independent gDNA sequence analysis [e.g. the Tilling methodology, which is restricted to screening at the most 5,000 to 10,000 mutants, and melting point differences between mutant and wild-type-derived gDNA fragments (Botticella et al., 2011)].

Until now, it was considered unrealistic to find predetermined and complex mutations using non-GM methods. Also along this line, there were no hints on which sample sizes to work with in order to robustly identify specific nucleotide substitutions of interest. This is now made possible by following the guidance provided in the instant publication.

SUMMARY OF THE INVENTION

The present invention discloses methods to find individual, traditionally developed organisms having predetermined mutation(s) in nucleotides of interest in one or more target sequence(s). Said mutations may be mutations in genes conferring specific, useful traits.

In particular, based on surprising novel insights into the mutational structures, the invention provides a remarkable, yet relatively simple, new genome-wide method for application in mutant finding. The invention provides methods for identifying organisms with a predetermined mutation in one or more NOI(s). The predetermined mutation may be any desirable mutation. Thus, the invention provides non-GM methods, which enable the identification of organisms with particular mutations. This is made possible because of inventive exploitation of PCR techniques, particularly digital PCR. Accordingly, the invention discloses a novel approach that addresses the mutational DNA context to screen for, combined with a logistically inventive system that enables the analysis of gigantic collections of mutated organisms.

Novel time-reducing, processing-minimized actions are also disclosed to reach the challenging task of finding rare mutations, e.g. those expected to be localized in the aforementioned closed chromatin regions of cereal nuclei, including those of barley. Access to full genomic sequences may be utilised for the design of primers and/or probes for the methods. Thus, the full barley genome sequence (barley genome assembly in Ensembl Plants, version 082214v1), may be utilized for the design of primers and probes for specific genes, is very suitable to enhance the rate of finding a plant with a predetermined mutation.

In one embodiment, the instant invention provides methods to search—by ways of traditional or conventional breeding—for predetermined mutations that are, for instance, mutations resulting in a nucleotide substitution in a gene, or genes, related to a cereal trait. With the disclosed methods are presented ways to assist in elucidating the underlying molecular mechanisms related to endogenous and induced mutagenesis.

The invention is defined in the claims attached hereto.

The invention provides methods of identifying an organism of a predefined species that carries one or more predetermined mutation(s) in NOI(s) of a target sequence, said method comprising the steps of:
a) Providing a pool of organisms of said species, or reproductive parts thereof, representing a plurality of genotypes;
b) Dividing said pool into one or more sub-pools of organisms, or reproductive parts thereof;
c) Preparing gDNA samples, each comprising gDNA from each genotype within a sub-pool, while maintaining the potential for multiplication of organisms of each genotype within said sub-pool;
d) Performing a plurality of PCR amplifications, each comprising the gDNA sample from one sub-pool, wherein each PCR amplification comprises a plurality of compartmentalised PCR amplifications that each comprise part of said gDNA sample, a set of primers flanking the target sequence and PCR reagents, thereby amplifying the target sequence;
e) Detecting PCR amplification product(s) comprising one or more target sequences comprising the mutation(s) in the NOI(s) of interest, thereby identifying sub-pool(s) comprising said mutation;
f) Dividing the organisms, or reproductive parts thereof, of said identified sub-pool into secondary sub-pools;
g) Preparing gDNA samples, each comprising gDNA, from each genotype within a secondary sub-pool, while maintaining the potential for multiplication of organisms of each genotype within said secondary sub-pool;
h) Performing a plurality of PCR amplifications, each comprising the gDNA sample from one secondary sub-pool, a set of primers flanking the target sequence and PCR reagents, thereby amplifying the target sequence;
i) Detecting PCR amplification products comprising a target sequence comprising the predetermined mutation(s) in the NOI(s), thereby identifying secondary sub-pools under step h) comprising said mutation;
j) Identifying an organism, or reproductive part(s) thereof, within said secondary sub-pool carrying said mutation(s).

The invention also provides organisms identified by the methods of the invention. For example, the invention provides a barley plant carrying a mutation in the HvGS1-3 gene encoding glutamine synthase, wherein said mutated gene encodes mutated HvGS1-3 protein with reduced activity.

The invention is further illustrated herein in 5 work streams (WSs), which in a sequential way allows for the identification of a specific, predetermined nucleotide mutation in a collection of cereal mutant grains: WS1 particulars disclose procedures to establish collections of traditionally induced cereals plants; WS2-specifics detail how to structure complex grain samples; WS3 highlights how to identify those grain samples that comprise mutants; WS4-related analytics describe how to find individual, mutated cereal grains, and; WS5 focuses on how the combined use of two different digital PCR instruments facilitates screening of ultra-high numbers of gDNA samples derived from cereal grains.

DETAILED DESCRIPTION OF THE INVENTION

Definitions

Figure 1A:
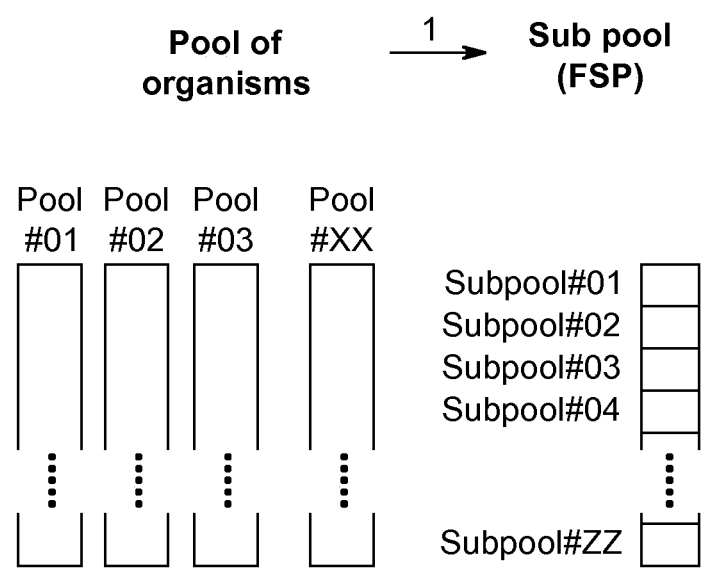
FIG. 1 illustrates an example on the overall experimental concept of the instant application.

The term "allele" refers to a specific version or state of a gene. The term "mutant allele" as used here refers to a gene carrying one or more predetermined mutation(s) in the NOI(s). When the mutation is a deletion of an entire gene, the mutant allele may also be an allele lacking said gene.

The term "approximately" as used herein in relation to numbers refers to ±10%, preferably ±5%, for example to ±1%.

The term "blocking probe" as used herein refers to an oligonucleotide, which cannot be extended at the 3' end by a DNA polymerase. The blocking probe will in general be an oligonucleotide, which is identical or complementary to the target sequence, including the reference NOI linked to a blocking agent, which inhibits extension of the blocking probe by a DNA polymerase.

The term "genotype" as used herein refers to an organism comprising a specific set of genes. Thus, two organism comprising identical genomes are of the same genotype. An organism's genotype in relation to a particular gene is determined by the alleles carried by said organism. In diploid organisms the genotype for a given gene may be AA (homozygous, dominant) or Aa (heterozygous) or aa (homzygous, recessive).

The term "mutant detection probe" as used herein refers to an oligonucleotide optionally linked to detectable means, wherein the oligonucleotide is identical to, or complementary to, the target sequence, including the predetermined mutation of the NOI.

The term "PCR" as used herein refers to a polymerase chain reaction. A PCR is a reaction for amplification of nucleic acids. The method relies on thermal cycling, and consists of cycles of repeated heating and cooling of the reaction to obtain sequential melting and enzymatic replication of said DNA. In the first step, the two strands forming the DNA double helix are physically separated at a high temperature in a process also known as DNA melting. In the second step, the temperature is lowered allowing enzymatic replication of DNA. PCR may also involve incubation at additional temperature in order to enhance annealing of primers and/or to optimise the temperature(s) for replication. In a PCR, the temperature generally cycles between the various temperatures for a number of cycles.

The term "PCR reagents" as used herein refers to reagents, which are added to a PCR in addition to a sample and a set of primers. The PCR reagents comprise at least nucleotides and a nucleic acid polymerase. In addition, the PCR reagents may comprise other compounds such as salt(s) and buffer(s).

The term "ddPCR" refers to droplet digital polymerase chain reaction. In ddPCR, one or more PCR amplifications are performed, wherein each reaction is separated into a plurality of water-oil emulsion droplets, so that PCR amplification of the target sequence may occur in each individual droplet.

The term "reproduction" as used herein refers to both sexual and asexual reproduction. Thus, reproduction may be multiplying an organism in a clonal manner (also known as "asexual reproduction"). Reproduction may also be generating progeny of an organism, wherein the progeny comprises allele(s) from the parent organism. Thus, reproduction of an organism comprising a mutant allele may refer to generating progeny of said organism, wherein the progeny comprises the mutant allele. Preferably, the mutant allele carries one or more of the mutation(s) in the NOI(s).

The term "reproductive parts of an organism" as used herein refers to any part of an organism which under the right conditions may grow into an entire organism. By way of example, in embodiments of the invention where the species is a plant, the reproductive part of said organism may, for example, be a seed, a grain or an embryo of said plant. In embodiments of the invention, wherein the species is a unicellular organism, then the reproductive parts is the entire organism, i.e. one cell.

The term "set of primers flanking a target sequence" as used herein refers to a set of two primers flanking a target sequence, so that one primer comprises a sequence identical to the 5' end of the target sequence (also referred to as "forward primer") and one primer comprises a sequence complementary to the 3' end of the target sequence (also referred to as "reverse primer"). The "set of primers" is capable to amplify the target sequence when added to a PCR together with a nucleic acid comprising the target sequence and PCR reagents under conditions allowing amplification of said target sequence.

The term "target sequence" as used herein refers to any nucleic acid sequence within which it is desirable to generate or identify a mutation. Furthermore, the target sequence is preferably a nucleic acid sequence, which can be amplified by PCR technology using primers flanking the target sequence. In addition, the target sequence generally comprises one or more NOI(s). The invention provides methods for producing and/or identifying organism(s) carrying a mutation in said NOI. The target sequence may, for example, be a nucleic acid sequence associated with a specific trait.

The term "reference detection probe" as used herein refers to an oligonucleotide optionally linked to detectable means, wherein the oligonucleotide is identical or complementary to the target sequence, including the reference NOI. In general, the target sequence, including the reference NOI, corresponds to the target sequence prior to mutagenesis. The "reference detection probe" may also be referred to as "wild-type probe".

The term "Work stream" (WS) as used herein relates to a series of one or more steps of a method.

Method of Identifying an Organism

The instant invention relates to methods for identifying an organism of a predefined species—e.g. any of the species described herein below in the section "Species", carrying a mutation in a NOI in a target sequence [for example any of the mutations described herein below in the section "Nucleotide(s) of interest"]—and said methods comprising the steps of:

a. Providing a pool of organisms of specified the predefined species, or reproductive parts thereof, representing a plurality of genotypes, e.g. any of the pools described herein below in the sections "Pool of organisms";

b. Dividing said pool into one or more sub-pools of organisms or reproductive parts thereof, e.g. as described herein below in the section "Dividing pool into sub-pools";

c. Preparing gDNA samples, each comprising gDNA from each genotype within a sub-pool, while maintaining the potential for multiplication of organisms of each genotype within said sub-pool, which—for instance—may be performed as described herein below in the section "Preparing DNA samples";

d. Performing a plurality of PCR amplifications, each comprising a gDNA sample from one sub-pool, wherein each PCR amplification comprises a plurality of compartmentalised PCR amplifications that each comprise part of said gDNA sample, a set of primers flanking the target sequence and PCR reagents, thereby amplifying the target sequence, which—for example—may be done as described herein below in the section "PCR amplification comprising a plurality of compartmentalised PCR amplifications";

e. Detecting PCR amplification product(s) comprising a target sequence comprising the mutation(s) in the NOI(s), thereby identifying sub-pool(s) comprising said mutation, which—for example—may be carried out as described herein below in the section "Detecting PCR amplification product(s)";

f. Dividing the organisms, or reproductive parts thereof, of said identified sub-pool into secondary sub-pools, e.g. as described herein below in the section "Dividing sub-pool into secondary sub-pools";

g. Preparing gDNA samples each comprising genomic DNA from each genotype within a secondary sub-pool, while maintaining the potential for multiplication of organisms of each genotype within said secondary sub-pool, which, for example, may be performed as described in the section "Preparing DNA sample";

h. Performing a plurality of PCR amplifications, each comprising a gDNA sample from one secondary sub-pool, a set of primers flanking the target sequence and PCR reagents, thereby amplifying the target sequence, which, for example, may be performed as described in the section "Identifying secondary sub-pools";

i. Detecting PCR amplification(s) comprising a target sequence comprising the mutation(s) in the NOI(s), thereby identifying secondary sub-pools comprising said mutation, which, for example, may be performed as described in the section "Identifying secondary sub-pools";

j. Identifying an organism within said secondary sub-pool carrying said mutation, which, for example, may be performed as described in the section "Identifying organism".

Step a. may for example comprise providing a pool of organisms prepared as described in WS1 herein.

Step b. may for example be performed as described in WS2 herein.

Steps c., d. and e. may for example be performed as described in WS3 herein.

Steps f., g., h., i. and j. may for example be performed as described in WS4 herein.

The PCR reagents, in general, comprise at least nucleotides and a nucleic acid polymerase. In addition, the PCR reagents may preferably also comprise one or more detection probes, e.g. a mutation detection probe and/or a reference detection probe as described herein above in the section "Detecting PCR product(s)".

In addition to the steps outlined above, the methods of the invention may comprise one or more additional steps. The methods may, for instance, comprise a step of preparing said pool of organisms, e.g. by mutagenesis. Methods for preparing the pool of organisms are described herein below in the section "Pool of organisms".

The methods may also comprise a step of reproduction of one or more of said organisms, or reproductive parts thereof, within the pool or within a sub-pool of organisms, or reproductive part(s) thereof. Said step of reproduction may in the case of simple organisms, e.g. unicellular organisms that reproduce asexually, comprise one or multiple cell division(s). In case of more complex organisms, e.g. organisms reproducing sexually, this step may include cultivating said organisms, or reproductive parts thereof, through one or more cycles.

In the following, reference is only made to "organism". However, the same considerations apply to methods using reproductive parts of organisms. Each step of cultivation of an organism may result in progeny, which is not identical to the original organism. For example, after random mutagenesis of polyploid organisms, most of the organisms will carry any random mutation only on one allele, and thus be genetically heterozygous with respect to that mutation. Generally, the progeny organisms comprise organisms without the mutation, progeny organisms genetically heterozygous for the mutation and progeny organisms genetically homozygous for the mutation. Thus, a pool of progeny of an original pool or organisms, or reproductive parts thereof, will not be identical to the original pool, but will, in general, at least represent any mutation in the NOI(s) present in the original pool—either heterozygotic and/or homozygotic organisms. Thus, at least some of said progeny will comprise the mutant allele. Similarly, progeny of a sub-pool, a super-pool or a secondary sub-pool may not be identical to the original sub-pool, super-pool or secondary sub-pool, but will, in general, at least represent any mutation in the NOI(s) present in the original sub-pool, super-pool or secondary sub-pool, either in the form of heterozygotes or homozygotes.

Step b) of dividing the pool into one more sub-pools may thus comprise a step of reproducing organisms, or reproductive parts thereof. This may, for example, be performed simultaneously with dividing the pool into sub-pools. Alternatively, this may be done after dividing the pool into sub-pools. Thus, the methods of the invention may subsequent to step b) comprise a step of reproduction of the organisms, or reproductive parts thereof, within said sub-pools.

Similarly, the methods of the invention may subsequent to step f) comprise a step of reproduction of the organisms, or reproductive parts thereof, within said secondary sub-pools. However, in some embodiments of the invention, and in particular in embodiments of the invention, wherein the species is a plant, such as a cereal, then it may be preferred that the methods do not comprise a step of reproduction of the organisms, or reproductive parts thereof, of the secondary sub-pools between steps f) and g).

In some embodiments of the invention, the methods comprise a step of reproduction of the organisms, or reproductive parts thereof, contained in the secondary sub-pool comprising the mutation in the NOI. Said step may be performed at any useful time, e.g. between steps i) and j) as outlined above.

The methods may also comprise a step of identifying a group of sub-pools comprising the mutation in the NOI. Said step may be performed at any useful time, but is frequently performed after step c) of the methods above—and may, for example, be performed as described in the section "Super-pools" herein below.

Figure 2A:
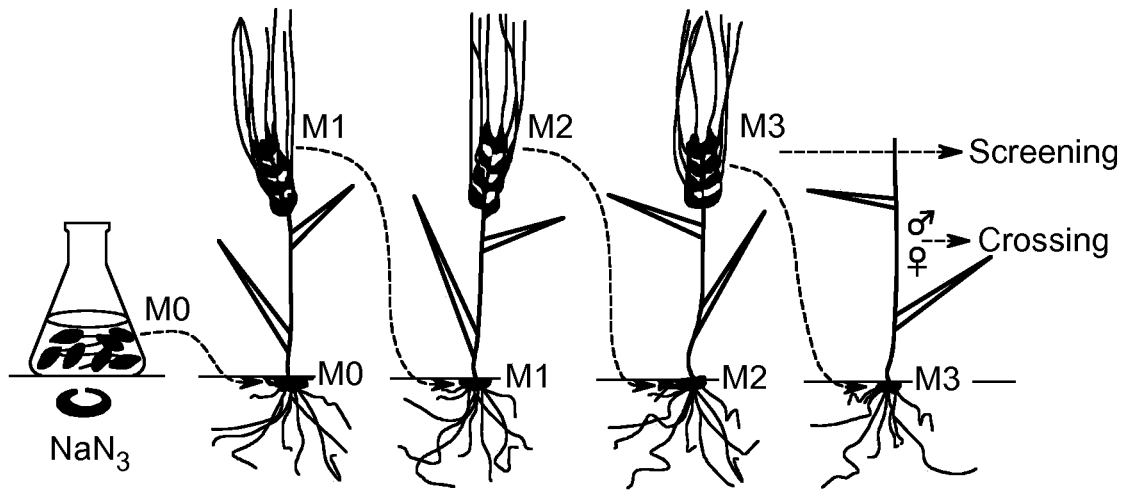
FIG. 2 illustrates an example of the overall experimental concept of the instant application, using the plant species barley as an example. A concerns the propagation of mutated barley grains (WS1 as explained in the detailed description of the invention); B shows aspects of making an ordered library of mutated grains (WS2 as explained in the detailed description of the invention); C provides a summary on how to determine whether a grain fraction contains individual grains of interest (WS3 as explained in the detailed description of the invention); D focuses on how to identify, in samples with grain mixtures, a grain with a specific mutation (WS4 as explained in the detailed description of the invention); E provides an illustration of the workflow involved in the detection of mutated DNA in samples of combined gDNA (WS5 as explained in the detailed description of the invention).

In one embodiment, the methods of the invention can be summarized in 4 to 5 individual work streams, e.g. WS1 to WS5, each divided into a number of individual "Steps" as described below. Whereas methods comprising, or even consisting, of WS1 to WS5 represent preferred embodiments of the invention, the invention is not limited to methods comprising these WSs. For example, the methods of the instant invention may comprise only WS2 to WS5, and lack WS1. Such a method is, for example, illustrated in FIG. 1. An example of a method comprising WS1 to WS5 is further illustrated in FIG. 2, divided into 5 parts, in which:

FIG. 2A concerns a specific example of WS1 in an embodiment of the invention, wherein the species is barley. The figure illustrates the propagation of mutated barley grains, as detailed in WS1 herein.

Figure 2B:
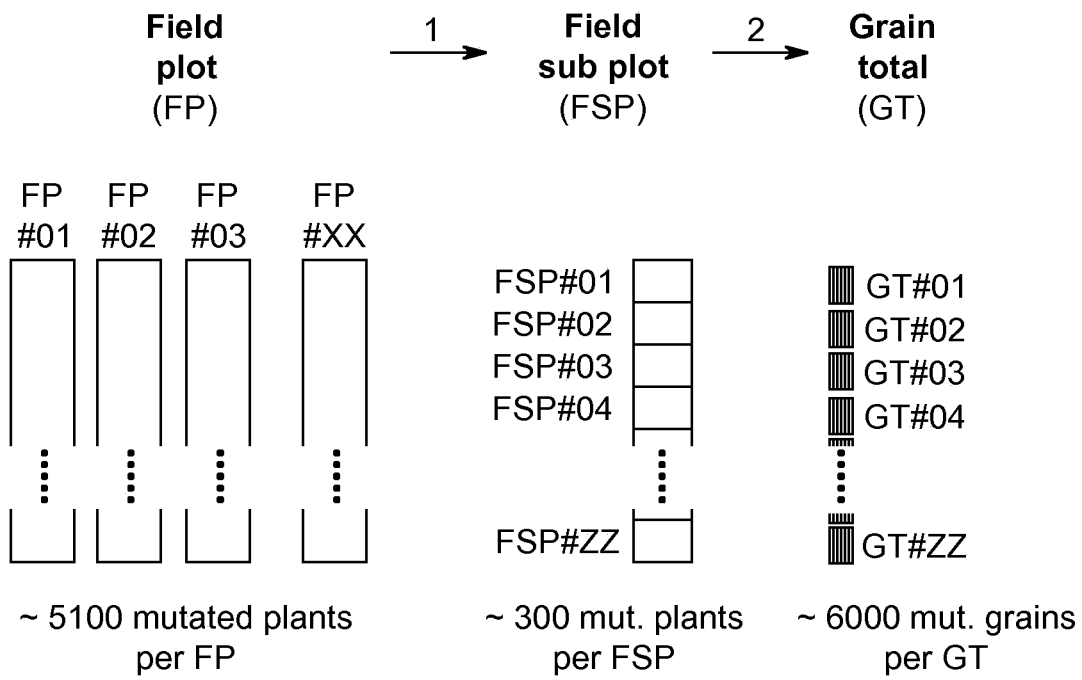

FIG. 2B shows an example of aspects of making an ordered library of mutated grains, as detailed in WS2 herein (cf. Example 1 and Example 2).

Figure 2C:
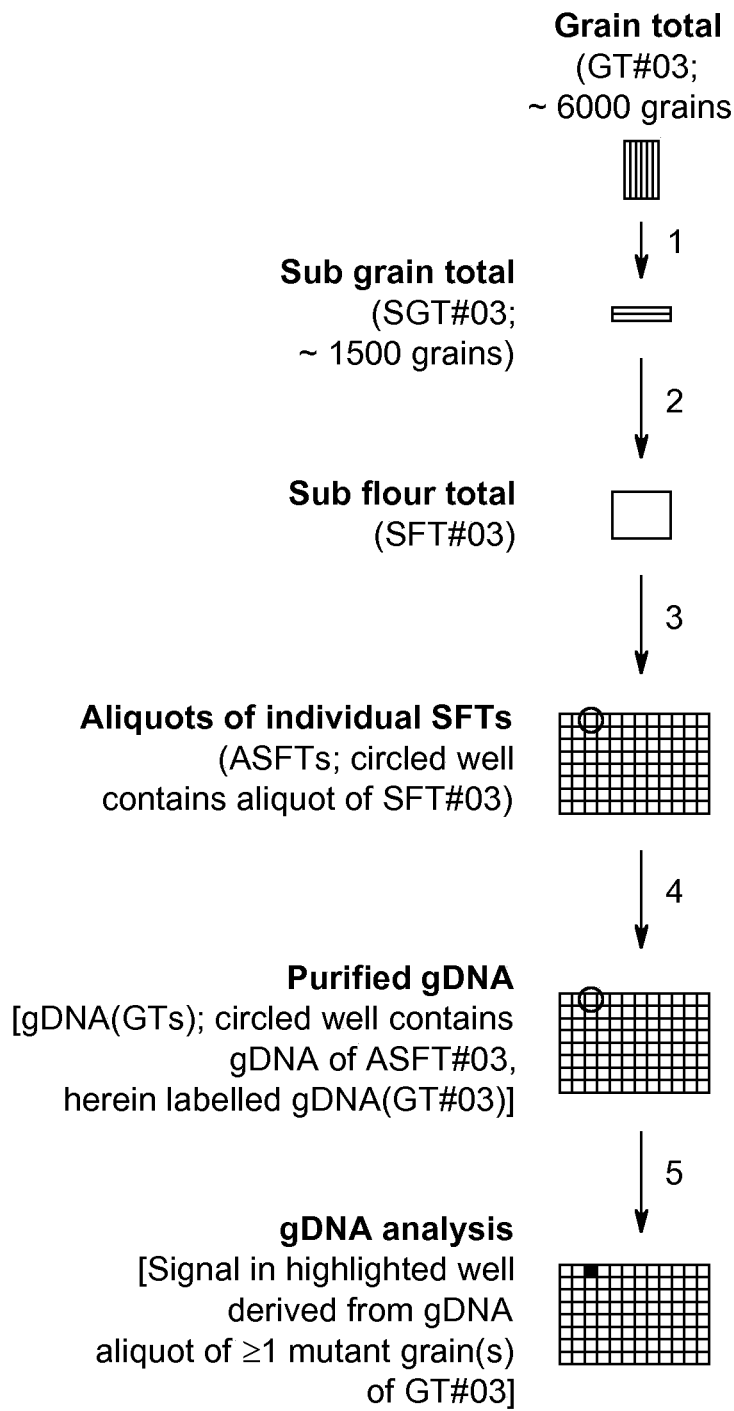

FIG. 2C provides an example of a summary on how to determine whether a "Grain total" fraction contains grain(s) characterized by a mutation in the NOI, as detailed in WS3 herein (cf. Example 3 to Example 7).

Figure 2D:
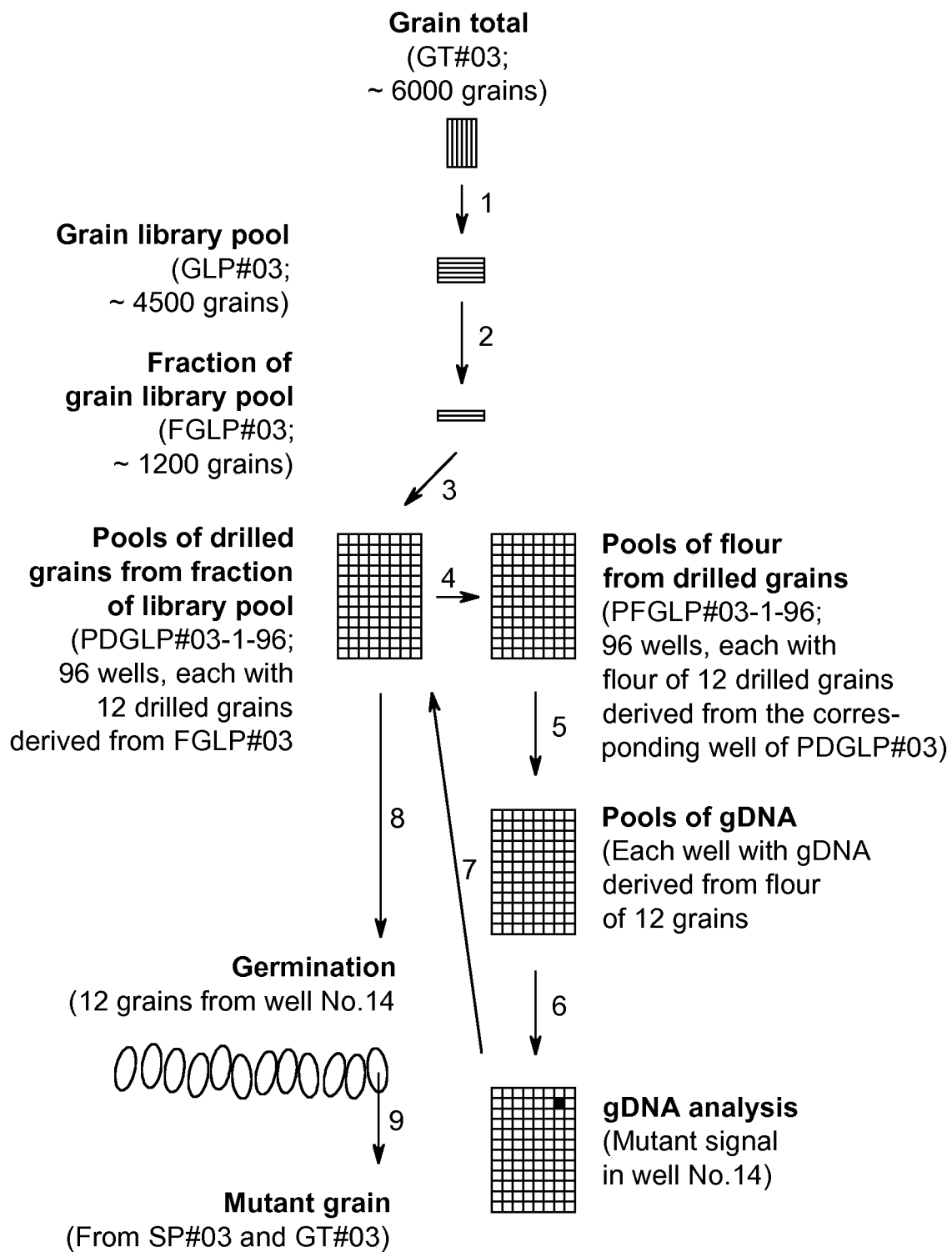

FIG. 2D highlights an example of WS4, i.e. procedures to determine which of the grain(s) in a "Grain total" fraction—with said fraction previously shown to contain grains containing the mutation(s) in NOI(s), cf. FIG. 2C—harbor the mutation in the NOI(s), as detailed in Step 4 herein (cf. Example 8 to Example 15).

Figure 2E:
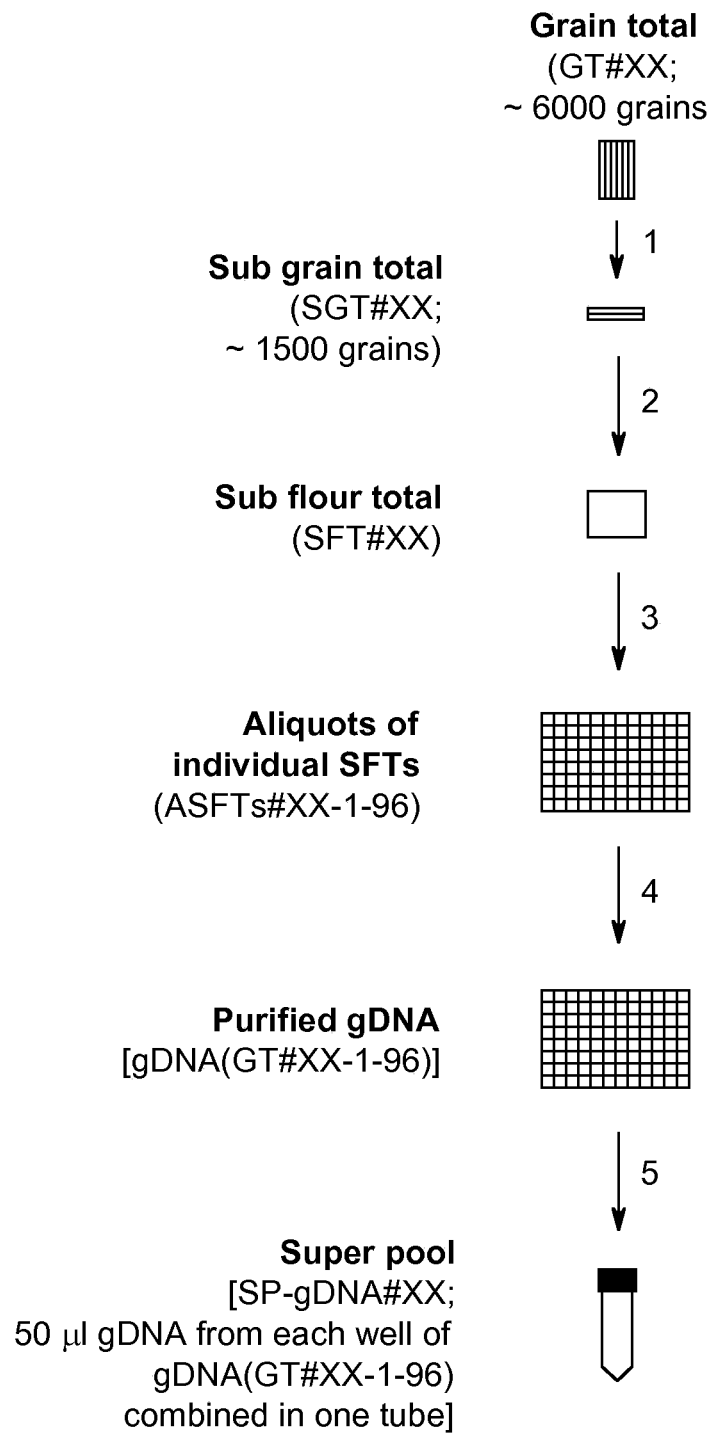

FIG. 2E presents an example of an overview of procedures in WS5 in which a compartmentalised PCR technology (e.g. ddPCR) is utilized to determine those "Super-pools" of gDNA, i.e. combined aliquots of gDNA samples (Example 17), that comprise the mutation corresponding to that in the NOI.

Nucleotide of Interest (NOI)

The invention relates to methods for the identification of one or more organism(s) carrying mutation(s) in one or more nucleotides of interest. In particular, the methods allow identification of organism(s) carrying one or more predetermined mutation(s) in NOI(s). Accordingly, the method allows identification of an organism carrying a specific mutation, while still relying on non-GM methods.

The mutation may be any mutation, wherein said one or more NOI(s) of interest differ from the corresponding NOI(s) in a reference sequence. Frequently, the reference sequence is a wild-type sequence. However, the reference sequence may also be any other sequence.

The mutation may be any kind of mutation, e.g. a deletion, an insertion, a substitution or a mixture of the aforementioned.

The NOI(s) may be a single nucleotide or several nucleotides, and thus the NOI(s) may consist of at least one, such as 1, for example 2, such as 3, for example 4, such as 5, for example 6, such as 7, for example 8, such as 9, for example 10, such as from 10 to 20, for example from 20 to 50, such as more than 50 nucleotides.

In preferred embodiments of the invention, the NOI consists of a single nucleotide—in which case the mutation, for example, may be a substitution of a single nucleotide. Such mutations are also known as point mutations.

In other embodiments of the invention, the mutation may be a deletion of said NOI. In other embodiments, the mutation may be an insertion of one or more nucleotides between two nucleotides of interest.

In one embodiment, the reference sequence is a wild-type sequence, i.e. the most frequently naturally occurring sequence, and the mutation is thus a mutation compared to said wild-type sequence.

In one embodiment, the mutation may be associated with a desirable trait within said species. Depending on the type of species, the desirable trait can be selected from a multitude of different traits. In embodiments of the invention, wherein the species is a domesticated plant, said trait could, for example, be enhanced viability, enhanced resistance to various environmental factors, enhanced growth or higher yield. In embodiments of the invention, wherein the species is a plant used for food, feed or beverage production, the trait could also relate to enhanced nutritional value, enhanced flavour properties, enhanced storage properties or enhanced usefulness for production of said food, feed or beverage.

The NOI may be positioned in any target sequence in any nucleic acid. Frequently, the target sequence is part of a gDNA sequence. More preferably, the target sequence is part of a gDNA sequence. Thus, the mutation may be a mutation of the gDNA of said organism. The NOI may be positioned in any part of the gDNA, in both coding and non-coding regions. Frequently, the NOI may be positioned in any part of a gene, e.g. within a coding region (e.g. within an exon), in an intron or in regulatory regions of a gene, e.g. in promoters, terminators and/or introns.

Species

The methods of the invention comprise identification of an organism of a predefined species. The species may be any species, including both multicellular and unicellular organisms. For example, the species may be a species contained in the Open Tree of Life, e.g. the The Open Tree of Life reference taxonomy version 2.9 draft 12 generated on 12 Oct. 2015.

The species may be a prokaryote, such as bacterium. Examples of bacteria include those used in production of food, e.g. bacteria of a genus selected from the group consisting of *Acetobacter, Arthrobacter, Alactobacillus, Bacillus, Bifidobacterium, Brachybacterium, Brevibacterium, Carnobacterium, Corynebacterium; enterococcus, Gluconacetobacter, Hafnia, Halomonas, Kocuria, Lactobacillus, Lactococcus, Leuconostoc, Macrococcus, Microbacterium, Micrococcus, Pediococcus, Propionibacterium, Proteus, Pseudimonas, Psychrobacter, Staphylococcus, Streptomyces, Tetragenococcus, Weissella* and *Zymomonas*.

The species may also be an eukaryote, e.g. selected from the group consisting of fungi, algae, plants and animals.

In one embodiment, the species is selected from the group consisting of fungi. Thus, the species may be a unicellular or a multicellular organism. For example, the species may be a fungus of a genus selected from the group consisting of *Aspergillus, Candida, Cystofilobasidium, Cyberlindnera, Debaryomyces, Fusarium, Geotrichum, Issatchenkia, Kazachstania, Kloeckera, Klyveromyces, Mucor, Neurospora, Penicillium, Pichia, Rhiozopus, Rhodosporidium, Rhodotorula, Saccharomyces, Torulaspora, Torulopsis, Thrichosporon, Verticillium, Yarrowia* and *Zygotorulaspora*.

In particular, the species may be yeast, such as yeast selected from the group consisting of *Saccharomyces cerevisiae, Saccharomyces pastorianus, Saccharomyces bayanus* and *Saccharomyces uvarum*. Other yeasts of interest include *Brettanomyces* species, and the like.

In one preferred embodiment of the invention, the species is a plant. Said plant may be a green plant, e.g. a plant selected from the group consisting of flowering plants, conifers, gymnosperms, ferns, clubmosses, hornworts, liverworts, mosses and green algae. The plant may, for example, be a monocot or a dicot.

In particular, the plant may be a domesticated plant. Said domesticated plant may be any plant cultivated by humans, e.g. as a source of food, feed or as a raw material for production of goods or for aesthetic purposes.

In one preferred embodiment of the invention, the species is a cereal. A "cereal", as defined herein, is a member of the Graminae plant family, cultivated primarily for their starch-containing seeds or grains. Cereals include, but are not limited to, barley (*Hordeum*), wheat (*Triticum*), rice (*Oryza*), maize (*Zea*), rye (*Secale*), oat (*Avena*), sorghum (Sorghum) and the wheat-rye hybrid Triticale.

The plant may also be other domesticated plants, including tomato.

As mentioned above, the species may also be an animal, e.g. a domesticated animal, such as an animal selected from the group consisting of cow, chicken, pig, sheep, goat, camel, horse turkey, duck and rabbit.

Pool of Organisms

The methods of the invention comprise providing a pool of organisms of a given species representing a plurality of genotypes. Said species may, for example, be any of the species described herein above in the section "Species".

Thus, the pool of organisms comprises a plurality of organisms, which all belong to the same species, but which represent different genotypes of said species. The pool may comprise more than one organism of each genotype. However, the pool must comprise a plurality of organisms of different genotypes. Preferably, the pool comprises at least 100, more preferably at least 1000, even more preferably at least 5000, yet more preferably at least 10,000, even more preferably at least 50,000, yet more preferably at least 100,000, e.g. at least 500,000, such as at least 1,000,000 organisms, or reproductive parts thereof, with different genotypes.

It is preferred that the pool of organisms comprises a sufficient number of organisms, or reproductive parts thereof, with different genotypes, such that the pool theoretically may comprise all possible mutations in all genes of said organism. For example, in embodiments of the invention, wherein the species is barley, it is believed that a pool comprising 500,000 randomly mutagenized barley grains will theoretically comprise all possible mutations in all genes of said barley (based on the assumption of 10,000 single-base mutations in one grain mutagenized with 1 mM $NaN_3$). To improve the efficiency of the methods of the invention, the pool may comprise at least 2×, such as at least 3× as many organisms, or reproductive parts thereof, with different genotypes than theoretically expected to comprise all possible mutations. Thus, the pool of organisms may comprise at least 500,000, such as at least 1,000,000, e.g. at least 1,500,000 organisms, or reproductive parts thereof, with different genotypes. This may, for example, be the case in embodiments, wherein the species in question is barley.

In some embodiments the pool may comprise at least 30,000 organisms, or reproductive parts thereof, with different genotypes, such as in the range of 30,000 to 500,000.

In some embodiments, the pool of organisms may comprise at least 5,000,000, such as in the range of 1,000,000 to 100,000,000 organisms, or reproductive parts thereof, with different genotypes. This may, for example, be the case in embodiments of the invention, wherein the organism is a small organism, e.g. a unicellular organism.

In other embodiments, the pool may comprise in the range of 100,000 to 500,000 organisms, or reproductive parts thereof, with different genotypes. This may for example be the case in embodiments of the invention, wherein the organism is a unicellular organism.

One advantage of the methods of the present invention is that the methods allow screening a large number of organisms of different genotypes. Thus, the pool of organisms may comprise a very large number of organisms of different genotypes. Further, the methods of the invention may allow identifying an organism with a predetermined mutation in any NOI. In order to be able to identify an organism with a mutation in any NOI, this may require that the pool of organisms comprises a large number of different genotypes, such as the aforementioned numbers of different genotypes.

The pool of organisms may be obtained in any useful manner.

In one embodiment, the pool of organisms is obtained by collecting individual organisms. This may, for example, be done from seed banks (provided that the species is a plant), from cell collections (provided that the species is a unicellular organism) or from other organism collections. It may also be achieved by collecting individual organisms, or samples of said organisms, in any other manner.

In a preferred embodiment of the invention, the pool of organisms is prepared by mutagenesis, in particular, by random mutagenesis. Thus, a plurality of organisms may be subjected to mutagenesis in order to obtain the pool of organisms. Said mutagenesis may in particular be random mutagenesis, which—for example—may be performed as described below.

In embodiments of the invention, wherein the organism is a unicellular organism, then typically a plurality of intact organisms are subjected to random mutagenesis.

In embodiments of the invention, wherein the species is a multicellular organism, it may be sufficient to subject a reproductive part of the said multicellular organism to said random mutagenesis. In such embodiments, either a plurality of organisms—or a plurality of reproductive parts of organisms, or a mixture thereof—is subjected to random mutagenesis.

In embodiments of the invention, wherein the species is a plant, then said pool may comprise a plurality of seeds that represent a plurality of genotypes. Thus, the pool may comprise a plurality of seeds, which have been subjected to mutagenesis. However, the pool may also comprise progeny of seeds, which have been subjected to mutagenesis.

Herein, seeds (e.g. cereal grains), which have been subjected to mutagenesis may be referred to as generation M0. Said seeds, e.g. cereal grains, may be sown and allowed to develop into mature plants, the seeds (e.g. cereal grains) of which are considered generation M1. Generation M1 seeds may be sown and allowed to grow into mature plants the seeds of which are considered generation M2 and so forth. This principle is illustrated in FIG. 2A.

The pool of organisms may comprise seeds, e.g. cereal grains, of any of the aforementioned generations. Thus, the pool does not necessarily contain seeds previously submitted to direct mutagenesis. The pool of organisms may also comprise seeds, e.g. cereal grains, of generation M1, M2 or M3.

Said random mutagenesis may be performed in any useful manner, e.g. by irradiation or chemical treatment. Irradiation may be UV-irradiation, X-ray irradiation or radioactive irradiation. Chemical mutagenesis may be treatment with any mutagenizing chemical, for example a chemical selected from the group consisting of sodium azide ($NaN_3$), alkylating agents such as N-ethyl-N-nitrosourea (ENU), methylnitrosoguanidine (MNNG) and ethyl methanesulfonate (EMS) or the alkylating agents mentioned below. $NaN_3$, ENU and EMS are often used to generate mutants at random. MNNG and EMS are frequently used to prepare randomly mutagenized yeast cultures.

To induce random mutations in a plant's gDNA, kernels or regenerable vegetative plant tissues can be treated with a mutagen, or a mixture of mutagens—including, but not limited to, alkylating agents such as: sulfonates, e.g. ethylmethane sulfonate (EMS), diethyl sulfonate (DES); sulphur mustards, e.g. ethyl-2-chloroethyl sulphide; nitrogen mustards, e.g. 2-chloroethyl-dimethyl amine, and; epoxides, e.g. ethylene oxide. Others are ethyleneimine, hydroxylamine ($NH_2OH$), N-methyl-N'-nitro-N-nitrosoguanidine (MNNG), $NaN_3$ and diazomethane. The treated tissues or kernels can then be propagated to generate off-spring organisms. Such random mutagenesis may be used with plants, such as crop plants, including cereals—but not limited to wheat, maize, rice, sorghum and millet—and dicotyledonous crop plants, including—but not limited to—rape seed, cotton, soybean and beet.

The methods of the invention are not restricted to any particular type of mutagenesis. Thus, any mutagenesis type can be used, such as any form of random mutagenesis.

In one embodiment of the invention, then the pool of organisms may be prepared as described herein below in the section "WS1" of the Examples. In embodiments of the invention, wherein the species is barley, the pool of organisms may be prepared as described herein below in the section "WS1" of the Examples in relation to barley. The skilled person will be able to adapt the methods described in WS1 for use with other flowering plants, including other cereal plants. In embodiments of the invention, wherein the species is yeast, the pool of organisms may be prepared as described herein below in the section "WS1" of the Examples in relation to yeast. The skilled person will be able to adapt the methods described in WS1 for use with other unicellular organisms.

Dividing an Organism Pool into Sub-Pools

The methods of the invention comprise a step of dividing the pool of organisms into one or more sub-pools, wherein each sub-pool comprises a plurality of organisms, or reproductive parts thereof. Preferably, each sub-pool comprises a plurality of organisms, or reproductive parts thereof, representing a plurality of genotypes.

Usually, the pool is divided into a plurality of sub-pools, preferably into at least 5 sub-pools, more preferably into at least 10 sub-pools, even more preferably into at least 30 sub-pools, yet more preferably into at least 50 sub-pools, even more preferably into at least 70 sub-pools, yet more preferably into at least 90 sub-pools.

In some embodiments, the pool is divided into at least 500, such as at least 1000, for example at least 1500 sub-pools. This may, in particular, be the case in embodiments of the invention, wherein the pool comprises a large number of organisms of different genotype.

There is, in principle, no upper limit to the number of sub-pools. Typically, however, the pool is divided into at the most 50,000, such as at the most 25,000, e.g. at the most 10,000 sub-pools.

In some embodiments, the pool is divided into in the range of 90 to 500 subpools.

Each sub-pool preferably comprises a plurality of organisms, or reproductive parts thereof, representing a plurality of genotypes. Preferably, each sub-pool comprises at least 10, more preferably at least 100, even more preferably at least 500, yet more preferably at least 1000, even more preferably at least 5000, yet more preferably at least 10,000, for example at least 50,000, such as at least 100,000 organisms, or reproductive parts thereof, with different genotypes. In some embodiments, each sub-pool comprises in the range of 2000 to 10,000, such as in the range of 3000 to 5000 organisms, or reproductive parts thereof, with different genotypes.

In some embodiments each sub-pool comprises in the range of 1000 to 2000 organisms, or reproductive parts thereof, representing different genotypes.

The sub-pools may be ordered in any desirable manner. If a pool comprises a plurality of organism of the same genotype, it is preferred that the majority of organisms, or even all organisms of the same genotype, are contained within the same sub-pool. This may be ensured in a multitude of manners depending on the species, e.g. as described below. In embodiments of the invention, in which the pool of organisms, or reproductive parts thereof, is prepared by random mutagenesis, it may be preferred that said pool is divided in a manner such that all progeny of one organisms from said pool, or reproductive part thereof, is comprised within one sub-pool.

For example, the pool may be divided into sub-pools, and said sub-pools may be subjected to a step of reproduction. It is also possible that the step of reproduction is performed simultaneously with the step of dividing the pool into sub-pools in a manner allowing progeny of a single organism, or reproductive part thereof, to end up in the same sub-pool.

It is also preferred that each sub-pool comprises more than one organism, or reproductive part thereof, of each genotype. This may be ensured in different manners. For example, sub-pools may be subjected to a step of reproduction allowing formation of progeny of each organism, or reproductive part thereof, of said sub-pool. In particular, it is preferred that each sub-pool comprises sufficient organisms of each genotype in order to randomly divide the sub-pool into 2, 3, or 4 parts in a manner such that each part, theoretically, comprises organisms (or reproductive parts thereof), representing each genotype of the sub-pool. Thus, it is preferred that each sub-pool comprises at least 5, preferably at least 10, even more preferably at least 15 organisms representing each genotype. This may, in particular, be the case in embodiments of the invention, wherein the species is a plant, e.g. a cereal. In embodiments of the invention, wherein the species is a unicellular organism, then it may be preferred that each sub-pool comprises many more organisms of each genotype, for example at least 100, such as at least 1000, for example at least 10,000.

An example of a method for dividing the pool into sub-pools is provided in FIG. 1A.

In embodiments of the invention, wherein the species is a unicellular organism, and the pool is prepared by mutagenizing a plurality of unicellular organisms, the sub-pools may, for example, be prepared as follows:

After mutagenesis, each unicellular organism may be allowed to multiply in a separate manner such that each unicellular organism develops into a clonal culture. This may be done by cultivating colonies of each clone on a solid medium or by cultivating each clone in in separate spaces, e.g. in tubes or wells, with liquid medium. The sub-pool may be formed by combining unicellular organisms from a plurality of clones;

The unicellular organisms may be divided into sub-pools immediately after mutagenesis, and each sub-pool may be allowed to reproduce.

Thus, the methods may comprise the steps of:
Providing a plurality of unicellular organisms, e.g. yeast;
Subjecting said organisms to random mutagenesis;
Dividing the mutagenized organisms into sub-pools;
Subjecting each sub-pool to a step of reproduction.

Said step of reproduction may comprise incubating each sub-pool in cultivation medium under conditions that allow growth of said organism. For example, the step may involve incubating the sub-pools in cultivation medium for in the range of 1 to 5 days at a temperature allowing growth of said organism.

In embodiments of the invention, wherein the species is a plant, then the sub-pool may be prepared in a manner such that all seeds of one particular plant are contained within one sub-pool. Thus, in one embodiment of the invention, the methods comprise the steps of:

Providing a plurality of seeds of a plant, e.g. cereal grains;
Mutagenizing said seeds, thereby obtaining seeds of generation M0;
Growing said seeds of generation M0 into mature plants, and obtaining seeds from said mature plants, wherein said seeds are seeds of generation M1;
Optionally repeating the previous step X times to obtain plants comprising seeds of generation M(1+X);
Obtaining seeds of either generation M1 or M(1+X) from said mature plants, thereby obtaining a pool of seeds (e.g. a pool of cereal grains);
Dividing said pool into sub-pools, wherein all seeds (e.g. cereal grains) from a given mature plant are placed into the same sub-pool.

These steps are illustrated in FIGS. 2A and 2B using barley as an example. The method may comprise the steps illustrated in FIGS. 2A and 2B. The steps illustrated in FIGS. 2A and 2B may be performed using any flowering plant, and are thus not limited to barley. Also, the steps illustrated in FIGS. 2A and 2B may be performed using any number of mutated plants (the numbers provided in the figure are merely an example).

Accordingly, the method may comprise the steps of:
Providing a plurality of plant seeds, e.g. cereal grains;
Mutagenizing said seeds, thereby obtaining seeds of generation M0;
Optionally cultivating said seeds of generation M0 into mature plants, and obtaining seeds from said mature plants, wherein said seeds are seeds of generation M1;
Optionally repeating the previous step X times to obtain plants comprising seeds of generation M(1+X);
Cultivating seeds of generation M0, M1 or M(1+X) in discrete field plots into mature plants, wherein the seeds of said mature plants constitute the pool of seeds;
Dividing said areas into field sub-plots;
Harvesting all seeds of all plants within one field sub-plot, thereby obtaining a sub-pool of seeds (e.g. a sub-pool of cereal grains), which may be referred to as "Grain total" (cf. FIG. 2B).

Instead of cultivating seeds in field plots, these may be cultivated in any useful manner to allow dividing of the plants into sub-groups, thus obtaining sub-pools. For example, the seeds may be cultivated in separate containers, each comprising one or more plants. The seeds may also be cultivated in a greenhouse.

One example of a method for dividing a pool into a sub-pool is described herein below in WS2.

Identifying Sub-Pools

The methods of the invention comprise the steps of dividing a pool of organisms, or reproductive parts thereof, into sub-pools. This is followed by a step of identifying a sub-pool comprising an organism, or reproductive parts thereof, comprising the mutation(s) in the NOI(s).

Identification of said sub-pool may comprise the steps of:
a) Preparing gDNA samples, each comprising gDNA from each genotype within one sub-pool, which, for example, may be performed as described herein below in the section "Preparing DNA samples";
b) Performing a plurality of PCR amplifications each comprising a plurality of compartmentalised PCR amplifications, e.g. done as described herein below in the section "PCR amplification comprising a plurality of compartmentalised PCR amplifications";
c) Detecting PCR amplification product(s) comprising the mutation(s) in the NOI(s) of interest, thereby identifying said sub-pool(s), e.g. done as described herein below in the section "Detecting PCR amplification product(s)".

The sub-pool may, for example, be directly identified provided that the PCR amplification product(s), comprising the mutation(s) in the NOI(s) that can be directly detected after, or during the PCR amplification. This may, for example, be done if the PCR amplification product(s) comprise(s) detection means, which give rise to one or more detectable signal(s), provided that the PCR amplification product(s) comprise(s) the target sequence(s) comprising the mutation(s) in the NOI(s). Such detection means are described in more detail below in the section "Detecting PCR amplification product(s)", and may, for example, be mutation detection probes.

Figure 1B:
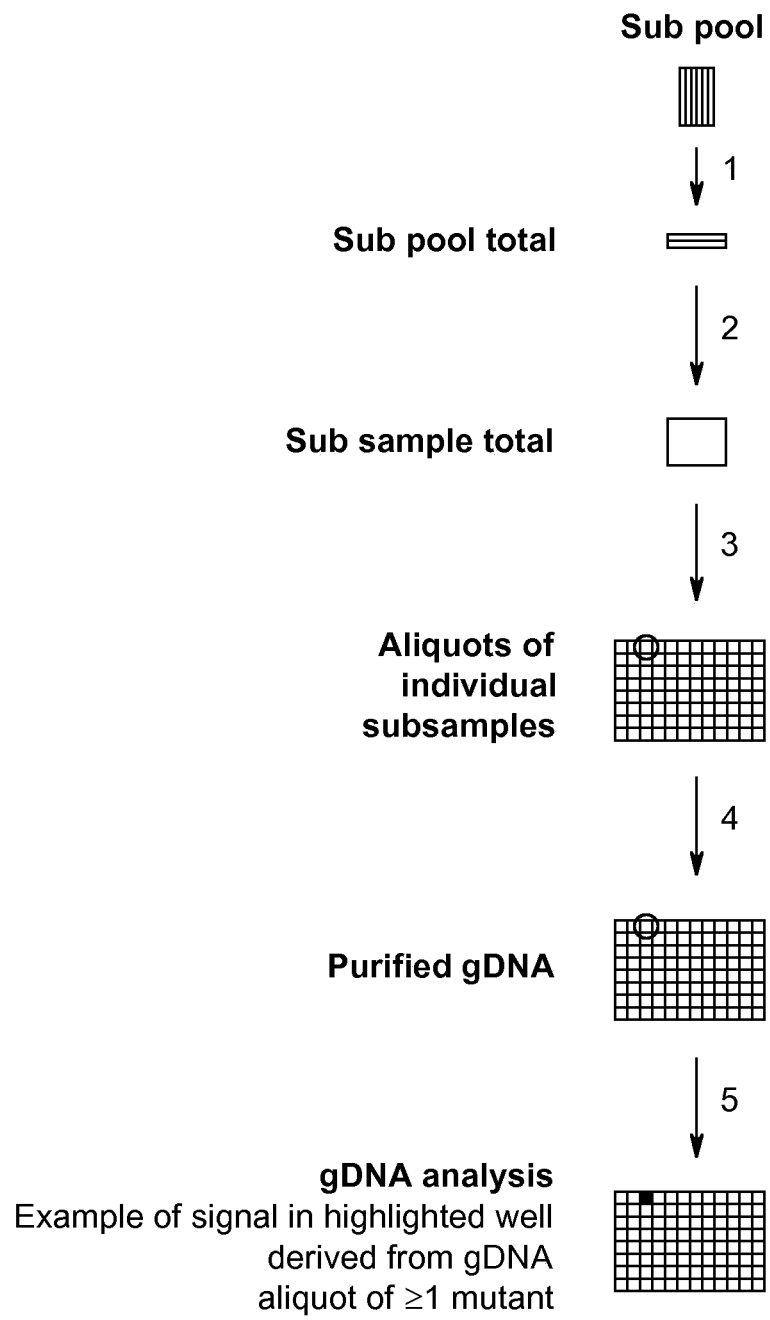

One example of a method for identification of a sub-pool comprising one or more specific mutation(s) is illustrated in FIG. 1B, highlighting the following steps:
Providing a sub-pool;
Preparing a sample from a part of said sub-pool;
Preparing a gDNA sample from said sample;
Preparing PCR amplifications with all of the individual gDNA samples from all of the sub-pools, e.g. in individual wells of a plate, e.g. in microtiter plates;
Selecting those samples which comprise the mutation(s) in the NOI(s).

A more specific example of a method to identify a sub-pool is shown in FIG. 2C. In this example, the species belongs to the group of a cereal plants. The specific numbers provided in FIG. 2C are examples only, and the skilled person will understand that the method can be performed using another amount of grains. For example, the identification of a sub-pool comprising the mutation in the NOI may be performed as outlined in WS3 herein below.

Preparing DNA Samples

The methods of the invention comprise one or more steps of preparing DNA samples, in particular gDNA samples. In particular, the methods may comprise one step of preparing gDNA samples from a sub-pool, and one step of preparing gDNA samples from a secondary sub-pool. The methods may also comprise a step of preparing gDNA samples from a super-pool.

In general, said gDNA samples are prepared in a manner so that the gDNA sample in theory comprises gDNA from each genotype within a sub-pool, secondary sub-pool or super-pool, while maintaining the potential for reproduction of organisms of each genotype within said sub-pool, secondary sub-pool or super-pool.

This may be ensured in different manners. For example, it may be preferred that each sub-pool and super-pool comprise more than one individual organism, or reproductive parts thereof, of each genotype. In particular, it may be preferred that each sub-pool or super-pool comprise sufficient organisms of each genotype in order to be able to randomly divide the sub-pool or the super-pool into 2, 3, or 4 parts in a manner such that each part in theory comprises organisms, or reproductive parts thereof, representing each genotype of the sub-pool or super-pool.

In that manner, a part of the organisms, or reproductive parts thereof, from the sub-pool or super-pool, e.g. in the range of 10 to 90%, preferably in the range 10 to 50%, such as in the range of 25 to 50% of the organisms, or reproductive parts thereof, of each sub-pool or each super-pool may be used for preparing the gDNA sample. Said part of the organisms, or reproductive parts thereof, is also referred to herein as "sample of organisms". The remainder of the organisms of the sub-pool may be stored under conditions maintaining the reproductive potential of said organisms, or reproductive parts thereof. In embodiments, wherein the organism is a plant, it may be sufficient to store seeds of said plants. Seeds, e.g. cereal grains, may frequently be stored in any dry and dark place. In embodiments of the invention where the organism is a unicellular organism, it may be preferred to freeze said organism—e.g. in the presence of a cryoprotectant, such as glycerol.

Similarly, each said secondary sub-pool may comprise more than one individual organism, or reproductive parts thereof, of each genotype. Thus, a part of the organisms—or reproductive parts thereof—from the secondary sub-pool, e.g. in the range of 10 to 90%, preferably in the range 40 to 60%, such as in the range of 25 to 50% of the organisms, or reproductive parts thereof, of each secondary sub-pool may be used for preparing the gDNA sample. However, in some embodiments, in particular when the species is a larger organism, then it may be preferred that the gDNA sample of the secondary sub-pool is prepared from a sample of a part of each organism, or reproductive part thereof, as described below.

It is also comprised within the invention that the gDNA sample may be prepared from a sample obtained from each organism, or reproductive part thereof, of a sub-pool, of a secondary sub-pool or of a super-pool. For example, it is comprised within the invention that each sub-pool, super-pool and secondary sub-pool may comprise only one or a few organism, or reproductive parts thereof, of each genotype. In such embodiments, the gDNA sample may be prepared from a sample obtained from each organism, or reproductive part thereof. In general, it is only possible to obtain a sample from each organism in embodiments of the invention, wherein the species is of a sufficient size to obtain such a sample. This may, in particular, be relevant in embodiments of the invention where the species is an animal or a plant, such as a flowering plant.

Whereas the sub-pool and the super-pool preferably comprise several individual organisms, or reproductive parts thereof, of each genotype as noted herein elsewhere, then the secondary sub-pool frequently may comprise only a few—sometimes even only one—individual organisms, or reproductive parts thereof, of each genotype. Thus, in embodiments of the invention, wherein the species is a plant (e.g. a cereal), it is preferred that the gDNA sample from the secondary sub-pool is prepared by obtaining a sample of each individual organism and preparing gDNA samples from said samples.

When samples are obtained from each organism, or reproductive parts thereof, it is preferred that the samples are obtained in a manner not significantly impairing said organisms, or reproductive part thereof, with respect to the potential for reproduction. Thus, preferably, the sample comprises or consists of a part of the organism, or reproductive part thereof, that is not essential for reproduction. The sample may be obtained in any useful manner depending on the species, e.g. by using biopsy, cutting, drilling, grating, tearing or by applying a syringe equipped with a needle.

By way of example, in embodiments where the species is a cereal and where the sub-pool, super-pool or secondary sub-pool comprises cereal grains, then said sample preferably comprises a part of the cereal grain, which is not essential for reproduction. The sample may be obtained in different manners, e.g. by cutting-off part(s) of the grain using any sharp instrument, such as a knife, scalpel or scissors, grating-off part of the grain, or it may be obtained by drilling a hole into the grain. In the latter case, the sample may be the flour obtained after drilling.

Once that either the sample of organisms, or the sample obtained from the organisms, or parts thereof, is available (herein also collectively referred to as "sample"), the gDNA sample may be prepared from said samples in any useful manner. If said samples contain large structures, e.g. entire seeds, the first step for preparing a gDNA sample will typically involve dividing said contents of said sample into smaller parts, for example, by physical means, e.g. by crushing or milling. Methods of preparing the gDNA sample typically comprise the steps of disrupting cells and/or tissues, e.g. by detergent, by enzymes (e.g. lyticase), by ultrasound or by combinations thereof—thereby creating a crude lysate. Said lysate may be separated from any remaining debris by any useful means. The crude lysate may constitute the gDNA sample. Alternatively, the gDNA may be further purified, e.g. by separating said gDNA from the remainder of the lysate, e.g. by binding to a selective matrix, centrifugation, gradient centrifugation and/or precipitation (e.g. using a precipitating agent, such as a salt, an alcohol or magnetic beads). Prior to such separation, other components of the lysate—including proteins and/or nucleoproteins—may be denatured or destroyed, e.g. by use of enzymes and/or denaturing agents. Other RNA-containing molecules may be removed, e.g. with the aid of enzymes. Useful methods for preparing gDNA samples are, for example, described in Sambrook et al., Molecular Cloning—Laboratory Manual, ISBN 978-1-936113-42-2.

PCR Amplification Comprising a Plurality of Compartmentalised PCR Amplifications The methods of the invention comprise a step of performing a plurality of PCR amplifications each comprising a gDNA sample from one sub-pool (for example prepared as described in the sections above) thereby amplifying the target sequence. Each PCR amplification may comprise a plurality of compartmentalised PCR amplifications each comprising part of said gDNA sample, one or more set(s) of primers flanking the target sequence and PCR reagents.

The entire PCR reaction comprising a plurality of compartmentalised PCR amplifications may be prepared in a number of different manners. In one embodiment, the PCR amplification comprising a plurality of compartmentalised PCR amplifications may be conducted as a digital PCR (dPCR) amplification. Any dPCR amplification known to the skilled person may be used with the invention. In general, at least one dPCR amplification comprising a plurality of compartmentalised PCR amplifications will be prepared for each gDNA sample prepared. Thus, at least one dPCR amplification comprising a plurality of compartmentalised dPCR amplifications will be prepared per sub-pool.

In general, the compartmentalised dPCR amplification is prepared in a method comprising the steps of:
  Preparing a dPCR amplification comprising the gDNA sample, a set of primers flanking the target sequence and PCR reagents;
  Partitioning said dPCR amplification so that nucleic acid molecules within the sample are localized and concentrated within a plurality of spatially separated compartments;
  Performing a dPCR amplification;
  Detecting dPCR-based amplification products.

Said separated compartments may be any separate compartments in which PCR amplifications can be performed.

For example, it may be well of a plate, e.g. a well of a micro well plate or a microtiter plate, it may be microfluidic chambers, it may be capillaries, it may be the dispersed phase of an emulsion, or it may be a droplet or miniaturized chambers of an array of miniaturized chambers. The separated compartments may also be discrete spots on a solid support, e.g. discrete nucleic acid binding surfaces.

It is generally preferred that the gDNA sample is distributed randomly into the samples for compartmentalised dPCR amplification. It is also preferred that each compartmentalised dPCR amplification only comprises a small number of nucleic acids comprising the target sequence. Due to the nature of random distribution, there may be some variation in the number of nucleic acid molecules comprised in each compartmentalised dPCR amplification. In one embodiment, each compartmentalised dPCR amplification comprises, in average, at the most 10, such as at the most 5 nucleic acid molecules comprising the target sequence.

In one preferred embodiment of the invention, the dPCR amplification comprising a plurality of compartmentalised PCR amplification is a droplet digital polymerase chain reaction (ddPCR). ddPCR is a method to perform dPCR that is based on water-oil emulsion droplet technology. The PCR amplification is fractionated into a plurality of micro-droplets, and PCR amplification of the target sequence occurs in each individual droplet. In general, ddPCR technology uses PCR reagents and work flows similar to those used for performing conventional PCRs. Thus, the partitioning of the PCR amplification is a key aspect of the ddPCR technique.

Accordingly, compartmentalised ddPCR amplifications may be contained in droplets, which may, for example, include emulsion compositions, or mixtures of two or more immiscible fluids (for example as described in U.S. Pat. No. 7,622,280 or as described in the examples herein below). The droplets can be generated by devices described in WO/2010/036352. In particular, the droplets can be prepared using a droplet generator, for example QX200 Droplet Generator available from Bio-Rad Laboratories, USA (hereinafter abbreviated Bio-Rad). The term emulsion, as used herein, can refer to a mixture of immiscible liquids (such as oil and water). The emulsions may, for example, be water in oil droplets, e.g. as described [Hindson, B J et al. (2011). High-throughput droplet digital PCR system for absolute quantitation of DNA copy number. Anal Chem 83: 8604-8610]. The emulsions can thus comprise aqueous droplets within a continuous oil phase. The emulsions can also be oil-in-water emulsions, wherein the droplets are oil droplets within a continuous aqueous phase. The droplets used herein are normally designed to prevent mixing between compartments, with the content of an individual compartment not only being protected from evaporation, but also from coalescing with the contents of other compartments. Thus, each droplet can be regarded as a spatially separated compartment.

Each droplet for ddPCR may have any useful volume. Preferably, however, the droplets have a volume in the nL-range. Accordingly, it is preferred that the droplet volume, on average, is in the range of 0.1 to 10 nL.

Microfluidic methods of producing emulsion droplets using microchannel cross-flow focusing or physical agitation are known to produce either monodisperse or polydisperse emulsions. The droplets can be monodisperse droplets. Also, the droplets can be generated such that their sizes do not vary by more than ±5% of the average size of the droplets. In some cases, the droplets are generated such that the droplet sizes only vary with ±2% of the average size of droplets.

Higher mechanical stability can be useful for microfluidic manipulations and higher-shear fluidic processing (e.g. in microfluidic capillaries or through 90° turns, such as valves in fluidic paths). Pre- and post-thermally treated droplets, or capsules, can be mechanically stable to standard pipet manipulations and centrifugation.

A droplet can be formed by flowing an oil phase through an aqueous sample. The aqueous phase can comprise, or consist, of components in a PCR amplification, e.g. a PCR amplification comprising the gDNA sample, a set of primers flanking the target sequence and PCR reagents, such as any of the PCR reagents described herein below in the section "PCR reagents".

The oil phase can comprise a fluorinated base oil, which can be additionally stabilized by combination with a fluorinated surfactant such as a perfluorinated polyether. In some cases, the base oil can be one or more of HFE 7500, FC-40, FC-43, FC-70, or other common fluorinated oil. In some cases, the anionic surfactant is Ammonium Krytox (Krytox-AM), the ammonium salt of Krytox FSH, or morpholino derivative of Krytox-FSH.

The oil phase can further comprise an additive for tuning the oil properties, such as vapor pressure, viscosity or surface tension. Non-limiting examples include perfluorooctanol and 1H,1H,2H,2H-Perfluorodecanol. The oil phase may also be a droplet generating oil, e.g. the Droplet Generation Oil available from Bio-Rad.

The emulsion can formulated to produce highly monodisperse droplets having a liquid-like interfacial film that can be converted by heating into micro-capsules having a solid-like interfacial film; such micro-capsules can behave as bioreactors that retain their contents through a reaction process, such as PCR amplification. The conversion to microcapsule form can occur upon heating. For example, such conversion can occur at a temperature of greater than 50, 60, 70, 80, 90, or 95° C. In some cases, this heating occurs using a thermocycler. During the heating process, a fluid or mineral oil overlay can be used to prevent evaporation.

In some cases, the droplet is generated using a commercially available droplet generator, such as Bio-Rad QX100™ Droplet Generator or Bio-Rad QX200™ Droplet Generator. The ddPCR and subsequent detection may be carried out using a commercially available droplet reader, such as Bio-Rad QX100 or QX200™ Droplet Reader.

Each PCR amplification can be compartmentalized into any suitable number of compartments. However, in one preferred embodiment, each PCR amplification is compartmentalized into in the range of 1000 to 100,000 compartments (e.g. droplets). For example, each PCR amplification may be compartmentalized into in the range of 10,000 to 50,000 compartments (e.g. droplets). For example, each PCR amplification may be compartmentalized into in the range of 15,000 to 25,000 compartments (e.g. droplets). Further, each PCR amplification may be compartmentalized into approximately 20,000 compartments (e.g. droplets).

PCR Reagents

The method encompasses performing several PCR amplifications, wherein at least some of these PCRs may comprise a plurality of compartmentalised PCR amplifications.

Regardless of whether said PCR comprises compartmentalised PCR amplifications or not, then the PCR amplifications will in general comprise a gDNA sample, a set of primers flanking the target sequence and PCR reagents. Said PCR reagents may be any of the PCR reagents described herein in this section.

The PCR reagents, in general, comprise at least nucleotides and a nucleic acid polymerase. The nucleotides may be deoxy-ribonucleotide triphosphate molecules, and preferably the PCR reagents comprise at least dATP, dCTP, dGTP and dTTP. In some cases, the PCR reagents also comprise dUTP.

The nucleic acid polymerase may be any enzyme capable of catalysing template-dependent polymerisation of nucleotides, i.e. replication. The nucleic acid polymerase should tolerate the temperatures used for the PCR amplification, and it should have catalytic activity at the elongation temperature. Several thermostable nucleic acid polymerases are known to the skilled person.

In some embodiments of the invention, the nucleic acid polymerase has 5'-3' nuclease activity and can thus be used in the amplification reaction with a TaqMan® probe.

The nucleic acid polymerase may be *Escherichia coli* DNA polymerase I. The nucleic acid polymerase may also be Taq DNA polymerase, which has a DNA synthesis-dependent strand replacing 5'-3' exonuclease activity. Other polymerases having 5'-3' nuclease activity include, but are not limited to, rTth DNA polymerase. The Taq DNA polymerase, e.g. obtained from New England Biolabs, can include Crimon LongAmp® Taq DNA polymerase, Crimson Taq DNA Polymerase, Hemo KlenTaq™, or LongAmp® Taq.

In some cases, the nucleic acid polymerase can be, e.g. *E. coli* DNA polymerase, Klenow fragment of *E. coli* DNA polymerase I, T7 DNA polymerase, T4 DNA polymerase, Taq polymerase, Pfu DNA polymerase, Vent DNA polymerase, bacteriophage 29, REDTaq™, Genomic DNA polymerase, or Sequenase. DNA polymerases are described, e.g. in U.S. Patent Application Publication No. 20120258501.

In addition, the PCR reagents may comprise salts, buffers and detection means. The buffer may be any useful buffer, e.g. TRIS. The salt may be any useful salt, e.g. potassium chloride, magnesium chloride or magnesium acetate or magnesium sulfate.

The PCR reagents may comprise a non-specific blocking agent, such as BSA, gelatin from bovine skin, beta-lactoglobulin, casein, dry milk, salmon sperm DNA or other common blocking agents.

The PCR reagents may also comprise bio-preservatives (e.g. $NaN_3$), PCR enhancers (e.g. betaine, trehalose, etc.) and inhibitors (e.g. RNase inhibitors). Other additives can include dimethyl sulfoxide (DMSO), glycerol, betaine (mono)-hydrate, trehalose, 7-deaza-2'-deoxyguanosine triphosphate (7-deaza-2'-dGTP), bovine serum albumin (BSA), formamide (methanamide), tetramethylammonium chloride (TMAC), other tetraalkylammonium derivatives [e.g. tetraethyammonium chloride (TEA-Cl)]; tetrapropylammonium chloride (TPrA-Cl) or non-ionic detergent, e.g. Triton X-100, Tween 20, Nonidet P-40 (NP-40) or PREXCEL-Q.

Furthermore, the PCR reagents may also comprise one or more means for detection of PCR amplification product(s) comprising the mutation(s) in the NOI(s). Said means may be any detectable means, and they may be added as individual compounds or be associated with, or even covalently linked to, one of the primers. Detectable means include, but are not limited to, dyes, radioactive compounds, bioluminescent and fluorescent compounds. In a preferred embodiment, the means for detection is one or more probes. Thus, it is preferred that the PCR reagent comprises one or more detection probes, for example any of the probes described herein below in the section "Detecting PCR amplification product(s)".

Primers Flanking the Target Sequence

The methods of the invention involve the use of one or more primer set(s) that flank the target sequence. A discrete "set of primers" that flanks a target sequence includes one primer comprising a sequence identical to the 5' end of the target sequence (also referred to as "forward primer"), and one primer comprising a sequence complementary to the 3' end of the target sequence (also referred to as "reverse primer"). The primer set is capable of amplifying the target sequence when added to a PCR together with a nucleic acid comprising the target sequence and PCR reagents under conditions allowing amplification of said target sequence. The same primer set may be used for all PCR amplifications of the methods according to the invention, even though it is also possible that different sets of primers are used for the PCR amplifications of the different steps of the invention.

In addition to the sequence identical to the 5' end of the target sequence, the forward primer may comprise additional sequences. Similarly, in addition to the sequence complementary to the 3' end of the target sequence, the reverse primer may comprise additional sequences. For example, the primers can at the 5' end contain an additional nucleic acid sequence, which does not hybridize to a target nucleic acid, but which facilitates handling of the primer or the PCR amplification product, e.g. detection of said product.

The length of the forward primer and the reverse primer can depend on the sequence of the target sequence. For example, the length of the primers can be adjusted to achieve a desirable melting temperature, $T_m$, of the primers. Thus, the length of the forward primer and reverse primer can, individually, be in the range of 10 to 100 nucleotides, for example in the range of 10 to 50 nucleotides, such as in the range of 15 to 20 nucleotides, such as in the range of 15 to 25 nucleotides, such as in the range of 15 to 30 nucleotides, such as in the range of 15 to 40 nucleotides, such as in the range of 15 to 45 nucleotides, such as in the range of 15 to 50 nucleotides in length. $T_m$ of the forward primer and the reverse primer is typically adjusted to in the range of 40 to 70° C.

Primer concentration within the aqueous phase of the PCR amplifications can, for example, be in the range of 0.05 to 2.0 µM, such as in the range of 0.1 to 1.0 µM, such as in the range of 0.2 to 1.0 µM, such as in the range of 0.3 to 1.0 µM, such as in the range of 0.4 to 1.0 µM or in the range of 0.5 to 1.0 µM.

The forward primer and reverse primer in general, comprise—or even consist—of oligonucleotides. However, in some cases, the primers may comprise nucleotide analogues. Numerous nucleotide analogues are known to the skilled person and include derivatives, wherein a sugar is modified, as in 2'-O-methyl, 2'-deoxy-2'-fluoro, and 2',3'-dideoxynucleoside derivatives, nucleic acid analogs based on other sugar backbones, such as threose, locked nucleic acids (LNA), LNA derivatives, peptide nucleic acids (PNA), glycol nucleic acid (GNA), threose nucleic acid (TNA), bicyclo sugars, or hexose, glycerol and glycol sugars, nucleic acid analogs based on non-ionic backbones, or nucleic acids and their analogs in non-linear topologies, such as dendrimers, comb-structures, and nanostructures.

The primers may also be linked to various tags (e.g. fluorescent tags, functionalized tags or binding tags), which can optionally be bound to their ends, sugars, or nucleobases.

Primers can be prepared by a variety of methods, including—but not limited to—cloning of appropriate sequences and direct chemical synthesis using methods well known in the art [Narang et al., Methods Enzymol. 68:90 (1979); Brown et al., Methods Enzymol. 68:109 (1979)]. Primers can also be obtained from commercial sources.

The forward primer and reverse primer can have an identical melting temperature or a similar melting temperature, e.g. a melting temperature of ±5° C. The lengths of the primers can be extended or shortened at the 5' and/or 3' end(s) to produce a primer set with the desired melting temperatures. Accordingly, one of the primers of a primer pair can be longer than the other primer.

Primers may be designed based on melting temperature. An equation for determining the melting temperature of primers smaller than 25 bp is known as the Wallace Rule $[T_d=2\times(A+T)+4\times(G+C)]$. Here, $T_d$ is the temperature at a particular salt concentration at which 50% of an oligonucleotide and its perfect filter-bound complement are in duplex conformation. Typically, $T_d$ is determined in 0.9 M NaCl. However, other considerations are also relevant when designing a primer, e.g. its predicted secondary structure. Several computer programs and on-line services are available for the design of primers.

In one embodiment, the set of primers may be designed in a manner, wherein the primers specifically are capable of amplification of the target sequence comprising the mutation in the NOI, but are not capable of amplifying the target sequence comprising the reference NOI. This may, for example, be achieved by designing the forward primer to comprise a sequence identical to the NOI(s) comprising the mutation(s), and/or it may be done by designing the reverse primer so that it comprises one or more sequences complementary to the NOI comprising the mutation(s).

In other embodiments, the set of primers may be designed in manners, wherein the primers specifically are capable of amplification of the target sequence comprising the reference NOI, but are not capable of amplifying the target sequence comprising the mutation(s) in the NOI(s). This may, for example, be achieved by designing the forward primer such that it comprises a sequence identical to the reference NOI, and/or by designing the reverse primer that comprises a sequence complementary to the reference NOI.

However, in preferred embodiments of the invention, the sets of primers are capable of amplifying both the target sequence that comprise the mutation(s) in the NOI(s), and the target sequence comprising the reference NOI.

It is notable that the methods of the invention comprise PCR amplifications with more than one set of primers, e.g. 2 sets of primers, such as 3 sets of primers, for example in the range of 2 to 10 sets of primers. Thus, each PCR amplification may comprise several sets of primers flanking different target sequences. This allows detection of more than one different mutation during one PCR amplification.

Detecting PCR Product(s)

The methods of the invention comprise at least two steps of detecting PCR amplification product(s) comprising target sequence(s) that comprise mutation(s) in NOI(s) of interest. The PCR amplification product(s) may be detected by any useful means.

As described above, said mutation(s) may be substitution(s), deletion(s) and/or insertion(s), involving from only one or a few nucleotide(s) to a large number of nucleotide(s). Thus, the detection may be adapted to the particular mutation specified by the NOI.

In some embodiments, the set of primers are designed in a manner, wherein the primers specifically are capable of amplifying of the target sequence comprising the mutation(s) in the NOI(s), but are not capable of amplification of the target sequence comprising the reference NOI.

In other embodiments, the set of primers may be designed in a manner, wherein these specifically are capable of amplifying the target sequence comprising the reference NOI, but not the target sequence comprising the mutation(s) in the NOI(s). In such embodiments, the detection may simply be based on detecting the presence or absence of a PCR amplification product. This may, in particular, be the case in embodiments of the invention, wherein the mutation is a mutation of a larger number of NOIs.

In preferred embodiments, the PCR amplification products are detected with the aid of detection probe(s). This may, in particular, be the case when the mutation(s) is mutation of a smaller number of NOI(s), for example one or more point mutations.

The detection probe may be an oligonucleotide comprising a sequence that is identical to the NOI comprising the mutation. In addition, said probe usually also comprises sequences identical to the regions of the target sequence that flank the NOI. Similarly, the detection probe may be an oligonucleotide comprising a sequence that is complementary to the NOI comprising the mutation, and in addition said probe may also comprise sequences complementary to the regions of the target sequence flanking the NOI. Said regions flanking the NOI may be the sequence(s) immediately 5' and/or 3' of the NOI(s), respectively. Such probes will preferably anneal to PCR amplification products comprising the mutation in the NOI, but not to PCR amplification products comprising the reference NOI. Such detection probes are also referred to as "mutant detection probes" herein. The mutant detection probe typically comprises in the range of 10 to 30 nucleotides. In particular, the mutant detection probe may comprise a consecutive sequence of in the range of 10 to 30 nucleotides identical, or complementary, to the target sequence comprising the mutation in the NOI.

The detection probe may also be an oligonucleotide comprising a sequence that is identical to the reference NOI. In addition, said probe usually also comprises sequences identical to the regions of the target sequence flanking the NOI. Similarly, the detection probe may be an oligonucleotide comprising a sequence that is complementary to the reference NOI, and said probe may in addition also comprise sequences complementary to the regions of the target sequence flanking the NOI. Such probes will preferably anneal to PCR amplification products comprising the reference NOI, but not to these amplification products comprising the mutation in the NOI. Such detection probes are also referred to as "reference detection probes" herein. The reference detection probe typically comprises in the range of 10 to 30 nucleotides. In particular, the reference detection probe may comprise a consecutive sequence of in the range of 10 to 30 nucleotides identical to, or complementary to, the target sequence comprising the reference NOI.

In some embodiments, the PCR reagents comprise a set of probes consisting of a mutant detection probe and a reference detection probe. The "set of probes" is preferably capable of competing for the binding site(s) at the NOI(s) when added to a PCR amplification together with a nucleic acid comprising the target sequence, PCR reagents and the set of primers under conditions allowing amplification of said target sequence. As noted above, the detection probes are typically oligonucleotides. In particular, they may be short nucleotide stretches of single-stranded DNA. The detection probes may be associated with, or even covalently linked to detectable means—including, but not limited to, reporters, dyes, radioactive compounds, bioluminescent compounds, fluorescent compounds and fluorophore/quencher pairs.

In some embodiments the most 5' nucleotide of the detection probe is not a G. Thus, the mutation detection probe may comprise an oligonucleotide, wherein the most 5' nucleotide is not a G. Similarly, the reference detection probe may comprise an oligonucleotide, wherein the most 5' nucleotide is not a G.

The methods of the invention may comprise use of both a mutant detection probe and a reference detection probe. In such cases, preferably, the probes are differentially labelled, e.g. such that one of the probes is associated with, or covalently linked to, detectable means, whereas the other is not. It is also possible that both probes are associated with, or covalently linked to, detectable means, wherein said detectable means are different.

In one embodiment, the reference detection probe is labelled with a fluorophore at the 5' end and with a quencher at the 3' end. Said fluorophore and quencher may, for example, be HEX and Black-Hole Quencher, respectively. In one embodiment, the mutant detection probe is labelled with a fluorophore at the 5' end and with a quencher on the 3' end. Said fluorophore and quencher may, for example, be FAM and Black-Hole Quencher, respectively.

The PCR reactions may comprise a similar amount of the mutant detection probe and the wild-type detection probe. However in some embodiments it may be preferred that an excess of mutant detection probe is employed. This may in particular be the case for detecting PCR product(s) after PCR amplification on a super-pool. In such cases, the PCR may reactions comprise at least 2-fold, more preferably at least 4-fold excess of the mutant detection probe compared to the reference detection probe.

In some embodiments, the detection probe is a TaqMan® probe (Heid et. al, 1996), which takes advantage of the 5' exonuclease activity of a nucleic acid polymerase. This is why the PCR reagents preferably comprise a nucleic acid polymerase with 5' exonuclease activity (e.g. Taq polymerase). Typically, the TaqMan® probe may be either a mutant detection probe, as described above, or a reference detection probe, as described above, covalently linked to a fluorophore/quencher pair. Thus, the probe may contain a fluorophore, usually at or near the 5' base. In addition, the TaqMan® probes may contain a quencher, which can be at or near the 3' base, and capable of quenching the fluorescence of said fluorophore [cf. Tyagi et al., Nature Biotechnology 16:49-53 (1998)]. When irradiated, the excited fluorophore transfers energy to the nearby quencher rather than fluorescing [Forster or fluorescence resonance energy transfer (FRET)]. Thus, a close proximity of the fluorophore and quencher can prevent emission of any fluorescence, while the probe is intact. However, when the Taq Man® probe anneals to an internal region of the target sequence and the polymerase replicates a template on which a TaqMan® probe is bound, its 5' exo-nuclease activity can cleave the probe. This series of events abolish the functionality of quenching, i.e. no FRET, and the fluorophore starts to emit fluorescence, which can be measured by any useful means.

Notably, as emphasized above, it is also comprised within the invention that the methods may be used for identifying more than one different mutation. This may be achieved by using a plurality of sets of primers as described above. However, this may also be achieved by using several different detection probes. Thus, in one embodiment, the methods may be used for identifying more than one different mutation within NOIs in the target sequence. In such embodiments, the PCR reagents may comprise a reference detection probe and several mutation detection probes, wherein each mutation detection probe comprises an oligonucleotide having a sequence identical to or complementary to one of the mutations. Preferably, the reference detection probe and the mutation detection probes are linked to different detection means. All the mutation detection probes may be linked to the same detection means, or to similar detection means or to different detection means.

In some cases, the detection probe is a molecular beacon (MB), i.e. a probe comprising complementary sequences capable of self-hybridisation (also referred to as "stem"), resulting in a "hairpin loop" structure. The loop of the MB can contain sequences complementary to, or identical to, the NOI(s), either mutant or reference NOI(s). Furthermore, the MB typically comprises a fluorophore and a quencher positioned at either end of the MB, so that they are proximal to one another, when the probe is hybridised to itself. The MB may be either a mutant detection probe as described above or a reference detection probe as described above covalently linked to a fluorophore/quencher pair, and to stem sequence(s) providing the complementary regions of the MB. Further details regarding standard methods of making and using MBs are well established in the literature and MBs are available from a number of commercial reagent sources.

In some cases, a primer/probe is used; in some cases, the primer/probe is a Scorpions™ probe, which can provide a FRET-based stem-loop detection mechanism similar to MB, except that the probe also has a segment attached that serves as either forward or reverse primer (cf. Whitcombe et al. Nature Biotechnol. 1999, August 17(8): 804-7; U.S. Pat. No. 6,326,145). A Scorpions™ probe can maintain a stem-loop configuration in the unhybridized state, with the fluorophore quenched. A Scorpions™ probe can have a longer multi-component structure, e.g. a 5' fluorophore, then a target-specific stem-loop section, then a quencher, then a blocker [e.g. hexethelene glycol (HEG)], and finally a 3' primer sequence. The blocker can prevent reverse extension of the product onto the probe.

In some cases, a primer/probe is a Sunrise™ probe, which comprises a primer attached to a hairpin probe that is extended during amplification. This arrangement can separate an internal quencher from a 5' terminal fluorophore (Nazarenko et al., Nucl. Acids Res. 1997, 25: 2516-2521).

The detection probe can be of any useful length, for example in the range of 10 to 60 nucleotides in length. The oligonucleotide probe can also be in the range of 10 to 30 nucleotides in length. The precise sequence and length of an oligonucleotide probe can depend in part on the nature of the target polynucleotide to which it binds. The binding location and length can be varied to achieve appropriate annealing and melting properties for a particular situation. For example, the detection probe may be designed to have a melting temperature in the same range as the forward primer and/or the reverse primer, e.g. within ±10° C., such as within ±5° C.

The 3' terminal nucleotide of the detection probe(s) can be blocked or rendered incapable of extension by a nucleic acid polymerase. Such blocking can be conveniently carried out by the attachment of detectable means, either through a fluorophore or quencher to the terminal 3' base of the oligonucleotide probe by a linking moiety.

There is a great deal of practical guidance available in the literature describing useful fluorophore-quencher pairs, including methods for selecting fluorophore-quencher pairs, as exemplified herein below:

Clegg, Meth. Enzymol., 211: 353-388 (1992); Wo et al., Anal. Biochem., 218: 1-13 (1994); Pesce et al., editors, Fluorescence Spectroscopy (Marcel Dekker, New York, 1971); White et al., Fluorescence Analysis: A Practical Approach (Marcel Dekker, New York, 1970); and the like;

The literature also includes references providing exhaustive lists of fluorescent and chromogenic molecules and their relevant optical properties for choosing reporter-quencher pairs, e.g. Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like.

Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760; and the like.

Fluorophores and quenchers can, for example, be selected from fluorescein and rhodamine dyes. These dyes, combined with appropriate linking methodologies for attachment to oligonucleotides are described in many references, e.g. Khanna et al. (cited above); Marshall, Histochemical J., 7:299-303 (1975); Menchen et al., U.S. Pat. No. 5,188,934; Menchen et al., European Patent Application 87310256.0; and Bergot et al., International Application PCT/US90/05565. The latter four documents are hereby incorporated by reference.

A fluorophore/quencher pair can use a fluorophore, such as EDANS or fluorescein, e.g. on the 5'-end and a quencher such as Dabcyl, e.g. at the 3'-end.

Detection of PCR amplification product(s) may involve a step of comparing the signal obtained in a PCR amplification comprising a given gDNA sample with the signal obtained in a control PCR amplification. The signal may typically relate to the detectable means associated with a mutant detection probe and/or a wild-type detection probe. Thus, if said probes are associated with a fluorophore, the signal may be fluorescence. The control PCR amplification may be a PCR amplification performed under the same conditions, but lacking a gDNA sample—i.e. said control PCR amplification may lack a gDNA template, or it may contain only a control DNA comprising only the reference target sequence, e.g. wild-type gDNA. In some embodiments, any signal which is stronger than the signal from the control PCR amplification may be considered a positive signal, i.e. a signal indicating the presence of a target sequence comprising one or more mutations in the NOI.

In one embodiment any signal which is above a given threshold may be considered a positive signal. The threshold can be determined by any useful manner, typically by using a suitable software, e.g. the QX200™ Droplet Reader and Quantasoft™ Software available from Biorad.

In embodiments of the invention, wherein mutation detection reference detection probes are employed, the fractional abundance between the signal obtained from the mutation detection probe and that of the reference detection probe may be determined, and used to assess the presence of a PCR product. The fractional abundance may be determined as: [Signal of ("mutant detection probe")] divided by [Signals of ("reference detection probe"+"mutant detection probe")].

A sample may, for example, be assumed to contain target DNA comprising the mutation in the NOI, provided that it in a comparison with a control PCR amplification is characterized by:
 1) An increased fractional abundance, and/or;
 2) Increased concentration of mutant droplets, and/or;
 3) Increased number of mutant events at a scale of 50% or higher above average.

Mutant droplets may be droplets giving a positive signal from the mutant detection probe. Herein, "mutant event" equals the number of mutant droplets.

Dividing a Sub-Pool into Secondary Sub-Pools

Once a sub-pool comprising an organism, or reproductive parts thereof, carrying the mutation in the NOI has been identified, then the methods of the invention comprise a step of dividing said sub-pool into a plurality of secondary sub-pools.

As described above, part of the sub-pool may have been used for preparing a gDNA sample. Thus, only the remaining part of the sub-pool is available for division into secondary sub-pools. It is also comprised within the invention that the sub-pool is divided into several fractions, and that only one fraction is used for preparing the secondary sub-pool.

Each secondary sub-pool may comprise only one organism or reproductive part(s) thereof. Alternatively, each secondary sub-pool may comprise a plurality of organisms or reproductive parts thereof. For example, each secondary sub-pool may comprise a plurality of organisms, or reproductive parts thereof, representing a plurality of genotypes.

Usually, the sub-pool, or a fraction thereof, is divided into a plurality of secondary sub-pools, preferably into at least 5 secondary sub-pools, more preferably into at least 10 secondary sub-pools, even more preferably into at least 30 secondary sub-pools, yet more preferably into at least 50 secondary sub-pools, even more preferably into at least 70 secondary sub-pools, yet more preferably into at least 90 secondary sub-pools. There is, in principle, no upper limit to the number of secondary sub-pools.

However the pool is typically divided into at the most 50,000, such as at the most 25,000, for example at the most 10,000 secondary sub-pools.

Each secondary sub-pool may comprise one or a plurality of organisms, or reproductive parts thereof, representing a plurality of genotypes. Preferably, each secondary sub-pool comprises in the range of 1 to 100, preferably in the range of 1 to 50, even more preferably in the range of 1 to 20 organisms, or reproductive parts thereof, with different genotypes.

The secondary sub-pools may be ordered in any desirable manner. In some embodiments, a secondary sub-pool comprises only a limited number of organisms or reproductive parts thereof.

In other embodiments, the secondary sub-pool comprises a plurality of organisms of the same genotype. This may be ensured by subjecting the secondary sub-pool to a step of reproduction. It is also possible that the step of reproduction is performed simultaneous with the step of dividing the sub-pool into secondary sub-pools, in a manner allowing progeny of a single organism, or reproductive part thereof, to end up in the same secondary sub-pool.

The methods of the invention comprise preparation of one or more gDNA sample(s) from the secondary sub-pool. In embodiments of the invention, wherein the secondary sub-pool only comprises one or a few organisms of each genotype, or reproductive parts thereof, then the gDNA sample is typically prepared from a sample of each organism, or reproductive part thereof, e.g. as described herein above in the section "Preparing DNA samples".

In embodiments where the secondary sub-pool comprises a plurality of organisms of individual genotypes, or reproductive parts thereof, of each genotype, then the gDNA sample may be prepared from a fraction of the secondary sub-pool.

An example of a method for dividing the sub-pool into secondary sub-pools is provided in FIG. 10, wherein the first steps of said figure illustrates dividing the sub-pool, and obtaining a gDNA sample.

In embodiments of the invention, wherein the species is a unicellular organism, then the secondary sub-pools may, for example, be prepared as follows:

After identification of a sub-pool comprising the mutation in the NOI, each unicellular organism of said sub-pool may be allowed to multiply in a separate manner, so that each unicellular organism gives rise to a clonal culture. This may be done by cultivating colonies of each clone on a solid medium or by cultivating each clone in separate spaces with liquid medium, e.g. in microtubes or in wells of microtitre plates. The secondary sub-pool may be formed by combining unicellular organisms from a plurality of clones;

The unicellular organisms may be divided into secondary sub-pools immediately after identification of the sub-pool of interest, and each secondary sub-pool may be allowed to reproduce.

In one embodiment, the secondary sub-pools are prepared by the following steps:

i) Providing a sub-pool comprising the mutation(s) in the NOI(s);
ii) Propagating some, or all of the organisms, of said sub-pool in a clonal manner to obtain clonal cultures;
iii) Combining a fraction of organisms from a plurality of said clonal cultures to obtain secondary sub-pools.

As described above, gDNA samples may be prepared from a part of the organism of a sub-pool, whereas the rest of the organisms of a sub-pool may be stored. When the organisms are unicellular, then said organisms may be frozen for storage. In such embodiments, step i) above may comprise a step of reviving the organisms by incubation in culture medium at a temperature adequate for growth of said organism.

Preferably, said step of reviving comprises only minimal reproduction.

Step ii) mentioned above may, for example, be performed by plating the organisms on a solid medium at a titre low enough to spatially separate the organisms from each other on said medium.

Step iii) mentioned above may comprise combining a fraction of in the range of 10 to 1000, preferably in the range of 10 to 500, more preferably in the range of 10 to 100, e.g. in the range of 30 to 70 individual clonal cultures. It may be preferred to obtain two copies of each secondary sub-pool. This may be done by combining said fractions as mentioned above, and then dividing each secondary sub-pool in at least 2 parts. Alternatively, two copies of each secondary sub-pool may be prepared from the start by combining fractions of the same clonal cultures in two different containers. Typically, one part of the sub-pool is used for preparing a gDNA sample, whereas the other is stored (e.g. frozen in the presence of a cryoprotectant). Before preparing a gDNA sample and/or before storage, the secondary sub-pools may be subjected to a step of reproduction, e.g. to incubation in cultivation medium at a temperature useful for growth of the organism.

In embodiments of the invention, wherein the species is a plant, the secondary sub-pool may be prepared by obtaining a sample of each seed within a sub-pool, and combining samples from a predetermined number of seeds. In such embodiments, it is important to order the secondary sub-pools, such that the seeds of one secondary sub-pool and the samples of said secondary sub-pool can be identified. Thus, in one embodiment of the invention, the methods comprise the steps of:

Providing a sub-pool comprising a plurality of seeds of a plant, e.g. cereal grains, wherein said sub-pool comprises the mutation of the NOI.
Dividing the seeds of said sub-pool into secondary sub-pools, each comprising at least one seed, e.g. in the range of 1 to 100 seeds.
Obtaining a sample from each seed of the secondary sub-pools in a manner that leaves these sufficiently intact to develop into a plant, and combining all samples from all seeds of each secondary sub-pool.
Preparing a gDNA sample from said combined samples.

The steps outlined above are illustrated in the upper part of FIG. 2D, using cereal grains as an example. Thus, the method may comprise the steps illustrated in FIG. 2D. Also, the steps illustrated in FIG. 2D may be performed using any flowering plant, accordingly not limited to cereals. Further, the steps illustrated in FIG. 2D may be performed using any number of mutated plants (the numbers provided in FIG. 2D merely represent one example).

One example of a method for dividing a sub-pool into secondary sub-pools is described herein below in the WS4.

Identifying Secondary Sub-Pools

The methods of the invention comprise the steps of dividing a sub-pool of organisms, or reproductive parts thereof, comprising one or more mutation(s) in the NOI(s), into secondary sub-pools—followed by a step of identifying a secondary sub-pool comprising an organism, or reproductive parts thereof, comprising the mutation(s) specified by the NOI(s).

Identification of said secondary sub-pool may comprise the steps of:

a) Preparing gDNA samples, each comprising gDNA from each genotype within one secondary sub-pool, which—for example—may be performed as described herein above in the section "Preparing DNA samples";
b) Performing a plurality of PCR amplifications to amplify the target sequence;
c) Detecting PCR amplification product(s) comprising the mutation(s) in the NOI(s), thereby identifying said secondary sub-pool(s), which—for example—may be done as described herein below in the section "Detecting PCR amplification product(s)".

The PCR amplification described hereinabove may be any PCR amplification of the target sequence. Thus, said PCR amplification may be a conventional PCR amplification, or it may be a PCR amplification comprising a plurality of compartmentalised PCR amplifications as described herein above.

Each of said PCR amplifications, in general, comprises the gDNA sample of one secondary sub-pool, a set of primers flanking the target sequence and PCR reagents. The primers may be any of the primers described herein above in the section "Primers flanking the target sequence". The PCR reagents may be any of the PCR reagents described herein above in the section "PCR reagents". In particular, the PCR reagents comprise nucleotides and a nucleic acid polymerase. Preferably, the PCR reagents also comprise one or more detection probes, e.g. a mutation detection probe and/or a reference detection probe, as described herein above in the section "Detecting PCR product(s)".

The secondary sub-pool may, for example, be directly identified provided that the PCR amplification product(s) comprising the mutation in the NOI(s) can be directly detected after, or during, the process of PCR amplification. This may, for example, be done if the PCR amplification comprises detection means, which give rise to a detectable signal provided that the PCR amplification product(s) comprise the target sequence comprising the mutation(s) in the NOI(s). Such detection means are described in more detail above in the section "Detecting PCR amplification product(s)", and may, for example, include probes for mutation detection.

Figure 1C:
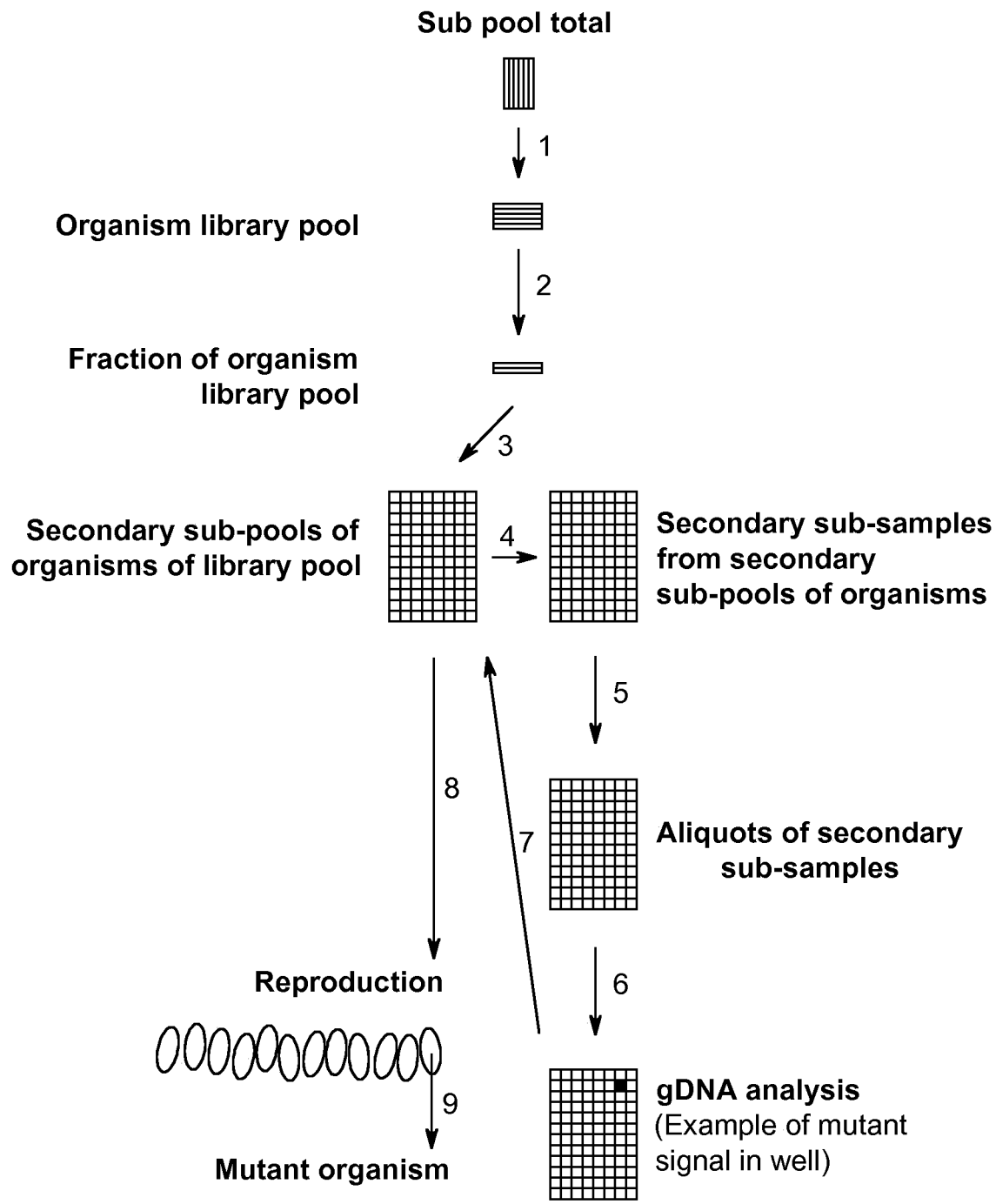

One example of a method to identify a secondary sub-pool comprising said mutation(s) is illustrated in the lower part of FIG. 1C, showing the following steps:

Providing a secondary sub-pool;
Preparing a sample from a part of said secondary sub-pool;
Preparing a gDNA sample from said sample;
Preparing PCR amplifications with all the individual gDNA samples from all the secondary sub-pools, for example in individual wells of a plate, e.g. in microtiter plates;
Detecting presence of the target sequence comprising the mutation in the NOI(s).

A more specific example on a method for the identification of a secondary sub-pool is shown in FIG. 2D. In this example, the species in question is a cereal plant. The specific numbers provided in FIG. 2D are examples only, and the skilled person will understand that the method can be performed using another number of grains.

It is notable that the identification of a secondary sub-pool comprising the NOI-specific mutation(s) may be performed as outlined in WS4 herein below.

Identifying Organism

Once a secondary sub-pool comprising an organism, or a reproductive part thereof, has been identified, the method comprises identification of an organism comprising the mutation(s) of the NOI(s).

This may be done in a number of ways, depending on the species and on the secondary sub-pools.

In embodiments of the invention, wherein the secondary sub-pool only comprises one organism, or reproductive parts thereof, then the organism, or reproductive part(s) thereof, is identified as soon as the relevant secondary sub-pool is identified.

In embodiments of the invention, wherein the secondary sub-pool comprises more than one organism, or reproductive part(s) thereof, then the methods typically comprise a step of identifying the organism(s). Prior to that, simultaneous with, or subsequent to the identification of the organisms, or reproductive parts thereof, the secondary sub-pool comprising the mutation(s) of the NOI(s) may be subjected to a step of reproduction.

In embodiments of the invention, wherein the species is a unicellular organism, said step of reproduction may be a clonal expansion of the organisms, e.g. by cloning each of the organisms of the secondary sub-pool in a spatially separated manner. Thus, the method may comprise the steps of:

i) Providing a secondary sub-pool comprising the mutation in the NOI;
ii) Reproducing some or all of the organisms of said sub-pool in a clonal manner;
iii) Determining which clones comprise organisms comprising the mutation in the NOI.

Step ii) mentioned above may, for example, be performed by plating the organisms on a solid medium at a titre low enough to spatially separate each organisms on said solid medium.

Step iii) above may involve preparing a gDNA sample from a fraction of each clone and performing a PCR amplification, e.g. a PCR amplification essentially as described in the section "Identifying secondary sub-pool" herein above.

In embodiments of the invention, wherein the species is a plant, and the secondary sub-pool comprises seeds of said plant, the methods may comprise the steps of:

A. Identifying a secondary sub-pool comprising an organism, or reproductive parts thereof, comprising the mutation(s) in the NO(s);
B. Cultivating all seed within said secondary sub-pool to allow germination, and optionally, growth of plants from each seed;
C. Obtaining a sample from each germinated seed;
D. Testing said sample for the presence of said mutation(s) in the NOI(s), wherein said testing may be performed by any method, e.g. by preparing a gDNA sample from said sample and performing a PCR amplification as described herein above, thereby identifying one plant carrying the mutation(s) in the NOI(s).

In step B. above, said seeds may, for example, be germinated and allowed to develop into plantlets comprising roots, stems and leaves. In such embodiments, the sample obtained in step C. may, for example, be a leaf, a root or parts thereof of said plantlet, such as sections of the first leaves. After the sample has been obtained, the germinated seed, or the plantlet, may be grown to maturity. It is also comprised within the invention that the plants are grown to maturity, in which case the sample obtained in step C., for example, may be a leaf, a flower, a root, a seed, a stem or parts thereof.

Subsequent to the identification of a single organism, or reproductive parts thereof, comprising one or more mutations in the NOI(s), said organism, or reproductive parts thereof, will—in general—be subjected to one or more steps of reproduction in order to obtain a plurality of organisms comprising the mutation.

In embodiments of the invention, wherein the identified organism is heterozygous with respect to the mutation in question, the method may then comprise steps of breeding said organism to homozygosity with respect to said mutation.

After identification of an organism comprising the mutation(s) in the NOI(s), the methods of the invention may comprise a step of further breeding said organism in a manner preserving the mutation(s) in the NOI(s). Such breeding may be performed with the aim of combining the trait conferred by the mutation(s) in the NOI(s) with traits of other organisms of the same species.

The methods may also comprise additional steps of verifying the presence of the mutation(s) in the NOI(s). For example, the target sequence—or a gene comprising the target sequence—may be sequenced in its entirety.

Super-Pools

In one embodiment of the invention, the methods comprise a step of identifying a group of sub-pools, herein also referred to as super-pools, comprising the mutation(s) in the NOI(s). In that manner, a very large number of potential organisms, or reproductive parts thereof, may be screened for the presence of the mutation(s) in the NOI(s). Said step is preferably performed after dividing the pool into sub-pools, and preparing gDNA samples from the sub-pools, e.g. after step c) of the methods of the invention.

Thus, the methods may comprise the following steps performed after step c):

Preparing a fraction of each gDNA sample from each sub-pool;

Combining a plurality of sub-pool fractions into super-pools, thereby obtaining gDNA samples of super-pools comprising gDNA of a plurality of sub-pools;

Performing a plurality of PCR amplifications each comprising a gDNA sample of a super-pool, wherein each PCR amplification comprises a plurality of compartmentalised PCR amplifications, each comprising part of said gDNA sample, a set of primers flanking the target sequence and PCR reagents, thereby amplifying the target sequence, wherein said PCR, for example, may be performed as described herein below in the section "PCR amplification on super-pool";

Detecting PCR amplification product(s) comprising target sequence(s) comprising the mutation(s) in the NOI(s), thereby identifying super-pool(s) comprising said mutation(s), wherein said step of detection for example may be performed as described herein above in the section "Detecting PCR products".

In some embodiments it may be preferred to enrich the gDNA samples of super-pools. This may aid in specifically detecting target sequence(s) comprising the mutation(s) in the NOI(s). The step of enriching may comprise the steps of providing gDNA samples of super-pools comprising gDNA of a plurality of sub-pools as described above;

Performing PCR amplifications each comprising a gDNA sample of a super-pool, wherein each PCR amplification comprises a set of primers flanking the target sequence, a blocking probe and PCR reagents.

The PCR amplification performed during the step of enrichment is typically a conventional PCR amplification and may for example be performed as described herein below in the section "PCR". Frequently, this PCR comprises a relatively low number of cycles, e.g. in the range of 10 to 30, such as in the range of 15 to 25 PCR cycles.

The blocking probe is typically a probe designed to inhibit amplification of the target sequence comprising the reference NOI. Thus, the blocking probe may for example be an oligonucleotide, which:

cannot be extended at the 3' end by a DNA polymerase;
preferentially binds the target sequence comprising the reference NOI or its complementary sequence over the target sequence comprising the predetermined mutation of the NOI The blocking probe typically comprises in the range of 10 to 30 nucleotides. In particular, the blocking probe may comprise a consecutive sequence of in the range of 10 to 30 nucleotides identical to, or complementary to, the target sequence comprising the reference NOI. Furthermore, the blocking probe typically is linked to a blocking agent, which inhibits extension of the probe by DNA polymerase.

Said blocking agent may for example be a moiety covalently linked to the most 3' nucleotide of the blocking probe. In fact, most 3' modifications will block extension. For example said blocking agent may be selected from the group consisting of 2',3'-dideoxyC spacer, 3'ddC and 3' Inverted dT. The blocking agent may also be a modification of the terminal 3' hydroxyl group e.g. with an amino group (e.g. a 3' amino) or an alkyl, e.g. a 3' C3 spacer. The blocking agent may also be a phosphorylation of the 3' nucleotide.

Once a super-pool is identified that comprises one or more mutations in the NOI(s), then step d) and the subsequent steps may be performed. However, step d) may be restricted to preparing PCR amplifications with gDNA samples of the sub-pools contained in the super-pool.

The identification of a super-pool may also be performed directly after preparing the sub-pools in step b). In this case, the methods may comprise the following steps after step b):

If the sub-pools comprise only a few e.g. only one organism, or a reproductive part thereof,) of each genotype, then said sub-pools may be subjected to a step of reproduction;

Preparing a fraction of each sub-pool, which represents each genotype within the sub-pool, wherein the remaining part of the sub-pool also represents each genotype within the sub-pool;

Combining a plurality of fractions into super-pools, thereby obtaining super-pools comprising organisms, or reproductive parts thereof, from a plurality of sub-pools, wherein organisms, or reproductive parts thereof, are only present in one super-pool;

Preparing gDNA samples, each comprising gDNA from each genotype within a super-pool, which—for example—may be performed as described herein above in the section "Preparing DNA samples";

Performing a plurality of PCR amplifications, each comprising a gDNA sample of a super-pool, wherein each PCR amplification comprises a plurality of compartmentalised PCR amplifications each comprising part of said gDNA sample, a set of primers flanking the target sequence and PCR reagents, thereby amplifying the target sequence—wherein said PCR, for example, may be performed as described herein below in the section "PCR amplification on super-pool".

Detecting PCR amplification product(s) comprising target sequence(s) comprising the mutation(s) in the NOI(s), thereby identifying super-pool(s) comprising said mutation(s).

In such embodiments, it is not important that the gDNA samples of the super-pools are prepared in a manner that maintains the potential for reproduction of organisms of each genotype within said super-pool. This is typically achieved because each super-pool contains DNA from a number of sub-pool, and each sub-pool comprises organisms (or reproductive parts thereof) representing each genotype within the sub-pool.

Once a super-pool is identified comprising the mutation(s) in the NOI(s), then step c) and the subsequent steps may be performed. However, step c) may be restricted to preparing gDNA samples of the sub-pools contained in the super-pool.

Any desirable number of super-pools may be prepared, e.g. in the range of 5 to 100, such as in the range of 5 to 50, e.g. in the range of 5 to 20.

Figure 1D:
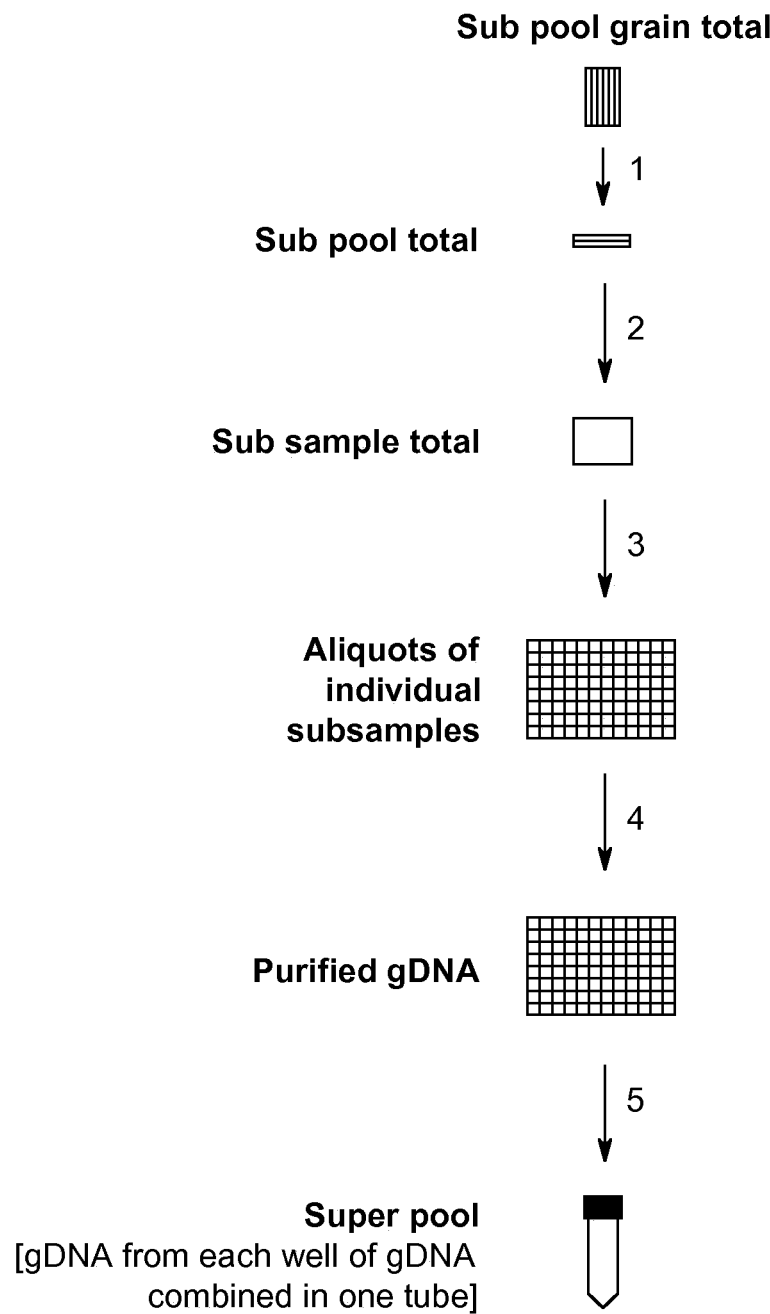

An example of a method for identifying a super-pool is illustrated in FIG. 1D. Another example, wherein the species is a cereal as illustrated in FIG. 2E. It is understood that the numbers provided in FIG. 2E are examples only, and that the method may be performed with another number of grains etc.

A non-limiting example of preparing and identifying a super-pool is also described herein below in WS5.

PCR Amplification on Super-Pool

The methods of the invention comprise a step of performing a plurality of PCR amplifications, each comprising a gDNA sample from one super-pool, for example prepared as described in the sections above, wherein each PCR amplification comprises a plurality of compartmentalised PCR amplifications each comprise part of said gDNA sample, a set of primers flanking the target sequence and PCR reagents, thereby amplifying the target sequence.

In general, said PCR may be performed as described herein above in the section "PCR amplification comprising a plurality of compartmentalised PCR amplifications"—preferably, however, with the exceptions as described below:

Compartmentalised PCR amplifications may be contained in droplets, as described above. For PCR amplifications on the super-pools, high sensitivity is of importance, whereas the PCR amplifications on sub-pools require lower sensitivity. Whereas a large quantity of reagents are typically required for the PCR amplifications with high sensitivity, the PCR amplifications with lower sensitivity require a smaller quantity of reagents. Thus, it is preferred that the PCR amplifications on the super-pools have a sensitivity for detecting one or several mutant NOI(s) within at least 200,000, more preferably within at least 250,000 reference NOIs.

For PCR amplifications on a super-pool, it may be preferred that each droplet has a very small volume, e.g. a volume in the pL-size. Accordingly, it is preferred that the droplets in average have a volume in the range of 0.1 to 10 pL.

Each PCR amplification can be compartmentalized into any suitable number of compartments. However, in one preferred embodiment, each PCR amplification is compartmentalized into in the range of 200,000 to 100,000,000 compartments (e.g. droplets). For example, each PCR amplification may be compartmentalized into in the range of 500,000 to 50,000,000 compartments (e.g. droplets), for example, each PCR amplification may be compartmentalized into in the range of 1,000,000 to 10,000,000 compartments (e.g. droplets). It may be preferred that each PCR amplification is compartmentalized into at least 1,000,000, preferably at least 3,000,000, even more preferably at least 5,000,000, such as at least 7,000,000 compartments (e.g. droplets).

In some cases, the droplets are generated using a commercially available droplet generator, such as the Rain-Drop Digital PCR System from Raindance Technologies, a system that also may be used for detecting PCR amplification product(s).

Once the compartmentalised PCR reactions have been prepared, the amplification may be performed as described herein below in the section "PCR" Detection of the presence of the target sequence comprising the mutant NOI(s) may be performed as described herein above in the section "Detecting PCR product(s)".

In one embodiment it may be preferred that the detection is performed using a reference detection probe and a mutant detection probe essentially described in the section "Detecting PCR product(s)", wherein an excess of mutant detection probe is employed. Preferably, the PCR reactions comprise at least 2-fold, more preferably at least 4-fold excess of the mutant detection probe compared to the reference detection probe. It is also possible that no reference detection probe is used and only mutant detection probe is used.

PCR

The methods described herein comprise multiple steps of performing PCR amplifications, including compartmentalised PCR amplifications, e.g. PCR amplifications as described in the section "PCR amplification comprising a plurality of compartmentalised PCR amplifications", or in the section "PCR amplification on super-pool".

Herein, in general, a PCR amplification comprises the steps of:
1) Preparing a PCR amplification comprising the gDNA sample, a set of primers flanking the target sequence and PCR reagents;
2) Performing a PCR amplification, which typically comprises the steps of:
   Incubating the PCR amplification at a denaturing temperature, e.g. in the range of 85 to 100° C., for example, in the range of 90 to 98° C. for a time sufficient to denature double-stranded DNA, e.g. for in the range of 15 to 30 min, such as in the range of 30 sec to 5 min;
   Performing a plurality of cycles, for example, in the range of 10 to 60 cycles, such as in the range of 20 to 40 cycles, comprising the following steps:
   Incubation at an annealing temperature to allow annealing between primers and target DNA, e.g. in the range of 15 sec to 2 min, such as in the range of 30 sec to 1 min. Typically, the annealing temperature will be a similar to, or lower than, the melting temperature of the primers, e.g. a temperature in the range of 45 to 75° C. Incubation at the annealing temperature may also allow elongation of the primers;
   Optionally, incubation at an elongation temperature at which the nucleic acid polymerase has activity, e.g. at a temperature in the range of 55 to 75° C. for in the range of 15 sec to 2 min, e.g. in the range of 30 sec to 1 min;
   Incubation at a denaturation temperature, e.g. at a temperature in the range of 85 to 100° C., or in the range of 90 to 98° C. in the range of 15 sec to 2 min, for example in the range of 30 sec to 1 min;
   Incubation at an elongation temperature of a DNA polymerase, e.g. in the range of 55 to 98° C., such as in the range of 15 sec to 20 min, such as in the range of 1 to 15 min.

Before the step of amplification, e.g. before step 2) of the previous list, the PCR may be partitioned into a plurality of spatially separated compartments in order to obtain compartmentalised PCR amplifications. This may, for example, be achieved by generating droplets, e.g. by adding a droplet-generating oil, and preparing droplets in a droplet generator.

Barley Plant Carrying a Mutation in the GS1-3 Gene

In one embodiment, the invention relates to a barley plant carrying a mutation in the gene encoding glutamine synthethase 1, specifically isoform 3 (GS1-3). Said gene may also be referred to as the HvGS1-3 gene, the protein-encoding sequence of which is provided herein as SEQ ID NO:1, whereas the amino acid sequence of the encoded HvGS1-3 enzymes is provided as SEQ ID NO:2.

Preferably, said mutation is a mutation which in said gene confers a sequence that encodes a mutated HvGS1-3 enzyme with reduced activity. The activity of HvGS1-3 is one or more of the following:
  i. Catalysing condensation of ammonium;
  ii. Catalysing condensation of ammonia and glutamate into glutamine;
  iii. Catalysing synthesis of glutamyl hydroxamate from glutamate, hydroxylamine, and ATP.

In particular, the activity of HvGS1-3 may be as described in iii. Here, the activity may, for example, may be determined as described in Example 19 herein below in the section "In vitro activity assay of recombinant HvGS1-3".

It is preferred that the mutated HvGS1-3 protein has an activity, which is lower than the activity of the wild-type protein. However, the enzyme should preferably retain at least some activity. In particular, said mutated HvGS1-3 protein may have a $k_{cat}$ (min$^{-1}$), which is in the range of 1 to 20%, such as in the range of 2 to 10% of the $k_{cat}$ (min$^{-1}$) of wild-type HvGS1-3 protein, when determined as described in the legend to Example 19.

The wild-type HvGS1-3 enzyme is believed to be a decamer consisting of two rings composed of 5 subunits. In one embodiment, the mutated HvGS1-3 protein contains a mutation in an amino acid residues lining the interphase between the two rings. In particular, the mutation may be a mutation in an amino acid residue selected from the group consisting of amino acid residues 141, 235, 285, 287 and 290 of SEQ ID NO:2.

Thus, the barley plant may comprise a mutation in the gene encoding HvGS1-3, wherein said gene encodes a mutated HvGS1-3 protein carrying a mutation of one of the aforementioned amino acid residues.

In particular, the mutated HvGS1-3 protein may be a protein with a mutation in amino acid residue no. 287 of SEQ ID NO:2, e.g. a mutation from Gly to any other amino acid residue, such as any other naturally occurring amino acid residue. The mutation may also be a mutation of amino acid residue 287 of SEQ ID NO:2, i.e. from Gly to a polar or charged amino acid residue, e.g. to an amino acid residue selected from the group consisting of Arg, Lys, Asp, Glu, Gln, Asn, His, Ser, Thr, Tyr, Cys, Met and Trp—or, for example, to an amino acid residue selected from the group consisting of Arg, Lys, Asp, Glu, Tyr, Phe, Met and Trp. The mutation may also be a mutation of amino acid residue 287 of SEQ ID NO:2 from Gly to a charged residue, e.g. to an amino acid residue selected from the group consisting of Arg, Lys, Asp and Glu. In particular, the mutation may also be a mutation of amino acid residue 287 of SEQ ID NO:2 from Gly to Asp.

The mutation in the HvGS1-3 gene may thus be any mutation resulting in a HvGS1-3 gene encoding one or more of the aforementioned mutations. In one embodiment, the gene mutation may be a mutation of one or more of nucleotides 859, 860 and 861 to obtain a codon encoding one of the aforementioned amino acid residues. In one example, the mutation is a gene mutation of nucleotide 860 from G to A.

In one embodiment, the mutated HvGS1-3 protein may be a protein carrying a mutation in amino acid residue no. 235 of SEQ ID NO:2, for example a mutation from Asp to any other amino acid residue. The mutation may also be a mutation of amino acid residue 235 of SEQ ID NO:2 from Asp to a positively charged residue, e.g. to an amino acid residue selected from the group consisting of Arg and Lys. The mutation in the HvGS1-3 gene may thus be any mutation resulting in a HvGS1-3 gene encoding any of the aforementioned, mutated HvGS1-3 proteins.

In one embodiment, the mutated HvGS1-3 protein may be a protein carrying a mutation in amino acid residue 285 of SEQ ID NO:2—for example a mutation from Gly into any other amino acid, such as any other naturally occurring amino acid. The mutation may also be a mutation of amino acid 285 of SEQ ID NO:2 from Gly to a polar or charged amino acid, e.g. to an amino acid residue selected from the group consisting of Arg, Lys, Asp, Glu, Gln, Asn, His, Ser, Thr, Tyr, Cys, Met and Trp. The mutation in the HvGS1-3 gene may thus be any mutation resulting in a HvGS1-3 gene encoding aforementioned, mutated HvGS1-3 proteins.

In one embodiment the mutated HvGS1-3 protein may be a protein carrying a mutation in amino acid residue 290 of SEQ ID NO:2, for example a mutation from Arg to any other amino acid residue. The mutation may also be a mutation of amino acid residue 290 of SEQ ID NO:2 from Arg to a negatively charged amino acid residue, e.g. to an amino acid selected from the group consisting of Asp and Glu. The mutation in the HvGS1-3 gene may thus be any mutation resulting in a HvGS1-3 gene encoding the aforementioned, mutated HvGS1-3 proteins.

In one embodiment, the mutated HvGS1-3 protein may be a protein carrying a mutation in amino acid residue 141 of SEQ ID NO:2, for example a mutation from Trp to any other amino acid residue. The mutation may also be a mutation of amino acid residue 141 of SEQ ID NO:2 from Trp to any other naturally occurring amino acid, except Tyr or Trp. The mutation in the HvGS1-3 gene may thus be any mutation resulting in a HvGS1-3 gene encoding any of the aforementioned mutated HvGS1-3 proteins.

The application also relates to the following embodiments:

1. A barley plant with a mutation in the gene encoding HvGS1-3, wherein said mutated gene encodes a mutated HvGS1-3 protein with reduced enzymatic activity.
2. The barley plant according to embodiment 1, wherein the mutated HvGS1-3 protein has a $k_{cat}$ value with respect to synthesis of glutamyl hydroxamate from glutamate, hydroxylamine and ATP of in the range of 1 to 20% of the $k_{cat}$ of wild-type HvGS1-3.
3. The barley plant according to any one of embodiments 1 to 2, wherein a HvGS1-3 form carries a mutation in amino acid residue 287 of SEQ ID NO:2.
4. Malt prepared from a barley plant according to any one of embodiments 1 to 3.
5. A beverage prepared from a barley plant according to any one of embodiments 1 to 3.
6. A method of producing a beverage, said method comprising the steps of: i. Providing kernels of a barley plant according to any one of embodiments 1 to 3;
   ii. Optionally, malting at least part of said kernels, thereby obtaining malt;
   iii. Preparing an extract of said barley and/or said barley malt;
   iv. Processing said extract into a beverage.
7. The method according to embodiment 6, wherein the beverage is beer.

Wheat Plant Carrying a Mutation in the GASR7 Gene

In one embodiment, the invention relates to a wheat plant carrying a mutation in the gene encoding GASR7 on the A genome. Said gene may also be referred to as the TaGASR7-A1 and the sequence is available at GenBank under number NCBI: KJ000052 and the coding sequence is provided herein as SEQ ID NO:25. The amino acid sequence of GASR7 is provided as SEQ ID NO:8.

Preferably, said mutation is a mutation which in said gene confers a sequence that encodes a mutated GASR7 enzyme with reduced activity. More preferably, the mutation is a mutation leading to a total loss of GASR7 function. Total loss of GASR7 function may for example be absence of GASR7 polypeptide. Loss of GASR7 function may also lead to increased grain length.

In particular it is preferred that the mutation is a mutation leading to GASR7 gene encoding a truncated form of GASR7, wherein said truncated form of GASR7 comprises at the most 91 amino acids, such as at the most 91 consecutive amino acids of SEQ ID NO:8. For example, the wheat plant may comprise a mutation in the GASR7 gene leading to a premature stop codon, for example a mutation resulting in formation of a stop codon at a codon encoding a Trp. In one embodiment, the wheat plant may comprise a mutation in the GASR7 gene leading to a premature stop codon at codon 91 (nucleotides 271-273) of SEQ ID NO:25 or at any codon positioned more 5'.

In one embodiment, the wheat plant may comprise a mutation in the GASR7 gene leading to a premature stop codon at the position encoding amino acid residue no. 91 of SEQ ID NO:8.

The application also relates to the following embodiments:

8. A wheat plant carrying a mutation in the gene encoding GASR7.
9. The wheat plant according to embodiment 8, wherein the wheat plant carries a mutation in the gene encoding GASR7 leading to a premature stop-codon.

Plant Products and Methods of Production Thereof

In one embodiment, the invention relates to plant products of a barley plant carrying a mutation in the HvGS1-3 gene, e.g. any of the barley plants described herein above in the section "Barley plant carrying a mutation in the GS1-3 gene". The plant product may be the plant per se or parts thereof. For example, the plant product may be barley kernels.

In one embodiment, the plant product is a malt composition. The malt composition may comprise or consist of malted barley plants or parts thereof—for example of malted barley kernels, i.e. barley kernels from a barley plant carrying a mutation in the HvGS1-3 gene, e.g. any of the barley plants described herein above in the section "Barley plant carrying a mutation in the GS1-3 gene".

Malted barley kernels are barley kernels, which have been subjected to a step of germination, following by a step of drying. The malt composition may comprise or consist of processed malt, for example, it may be "milled malt" or "flour". Thus, said malt composition may be prepared by a method comprising the steps of:
- Steeping cereal kernels, e.g. barley kernels;
- Germinating cereal kernels;
- Drying said germinated cereal kernels, e.g. by kiln drying at elevated temperatures.

The invention also relates to wort prepared from a barley plant carrying a mutation in the HvGS1-3 gene, e.g. any one of the barley plants described herein above in the section "Barley plant carrying a mutation in the GS1-3 gene". Wort is an aqueous barley extract that for example may be prepared by mashing malt, unmalted barley kernels and/or adjuncts. "Adjuncts" is understood to comprise any carbohydrate source other than malt, such as, but not limited to, cereals (e.g. barley, wheat, maize or rice)—either as whole kernels or processed products like grits, syrups or starch. All of the aforementioned adjuncts may be principally used as additional sources of extract (syrups are typically dosed after mashing). Before mashing, the malt is typically milled. Adjuncts, which are in larger pieces, e.g. whole kernels, are typically also milled.

Unmalted barley kernels lack, or contain only a limited amount of, enzymes beneficial for wort production, such as enzymes capable of degrading cell walls or depolymerising starch into sugars. Thus, in embodiments of the invention where unmalted barley is used for mashing, it is preferred that one or more suitable, external brewing enzymes are added to the mash. Even in embodiments of the invention, where cereal malt is used for wort production, external enzymes may be added during mashing. Suitable enzymes may be lipases, starch degrading enzymes (e.g. amylases), glucanases [preferably (1-4)- and/or (1-3,1-4)-β-glucanase], and/or xylanases (such as arabinoxylanases), and/or proteases, or enzyme mixtures comprising one or more of the aforementioned enzymes, e.g. Cereflo, Ultraflo or Ondea Pro (Novozymes).

Mashing is typically performed by incubating said milled malt and/or barley kernels, and optionally, adjuncts with water at elevated, predetermined temperatures. Typically, the mashing is performed at temperatures in the range of 40 to 80° C. The incubation temperature is, in general, either kept constant (isothermal mashing), or gradually increased. This may, for example, be practiced in a sequential manner. If the gelatinization temperature is above that normally observed for normal malt saccharification, then starch may be gelatinized and liquefied before addition to the mash. In either case, soluble substances in the malt/barley/adjuncts are liberated into said liquid fraction. A subsequent filtration confers separation of wort and residual solid particles, the latter also denoted "spent grain". The wort thus obtained may also be denoted "first wort". Additional liquid, such as water, may be added to the spent grains during a process "denoted sparging". After sparging and filtration, a "second wort" may be obtained. Further worts may be prepared by repeating the procedure. Non-limiting examples of suitable procedures for preparation of wort are described by Briggs et al. (supra) and Hough et al. (supra).

After mashing and/or sparging, the wort may be subjected to a step of boiling—optionally in the presence of additional compounds, e.g. hops, to obtain boiled wort.

Wort according to the invention may be first wort, second wort, further worts or combinations of the aforementioned, as well as boiled versions of any of the aforementioned.

In one preferred embodiment of the invention, the plant product is a beverage prepared from a barley plant carrying a mutation in the gene encoding HvGS1-3, e.g. a barley-based beverage, such as alcoholic barley-based beverages and non-alcoholic barley-based beverages. Alcoholic cereal-based beverages may, for example, be beer or a distilled alcohol.

Said beer may be any kind of beer, for example lager or ale. Thus, the beer may for example be selected from the group consisting of Altbier, Amber ale, Barley wine, Berliner weisse, Bière de Garde, Bitter, Blonde Ale, Bock, Brown ale, California Common, Cream Ale, Dortmunder Export, Doppelbock, Dunkel, Dunkelweizen, Eisbock, Fruit lambic, Golden Ale, Gose, Gueuze, Hefeweizen, Helles, India pale ale, Kölsch, Lambic, Light ale, Maibock, Malt liquor, Mild, Märzenbier, Old ale, Oud bruin, Pale ale, Pilsener, Porter, Red ale, Roggenbier, Saison, Scotch ale, Steam beer, Stout, Schwarzbier, lager, Witbier, Weissbier and Weizenbock.

Said distilled alcohol may be any kind of distilled alcohol. In particular, the distilled alcohol may be based on a barley plant carrying a mutation in the HvGS1-3 gene, e.g. a malted cereal, such as a barley malt. Non-limiting examples of such distilled alcohol include whiskey and vodka.

The beverage may be a non-alcoholic beverage, such as a non-alcoholic barley-based beverage, e.g. non-alcoholic beer or non-alcoholic malt beverages, such as maltina.

The beverages may, for example, be prepared by any of the methods described herein below.

Method of Producing a Beverage

In one embodiment, the invention relates to methods of producing a beverage. Such methods may comprise the steps of:

Providing a barley plant carrying a mutation in the HvGS1-3 gene, e.g. any of the mutations described herein above in the section "Barley plant carrying a mutation in the GS1-3 gene";

Preparing an aqueous extract of said plant or parts thereof;

Optionally further processing said aqueous extract into a beverage.

Thus, the invention provides in one embodiment methods for producing a beverage, said method comprising the steps of:
- a) Providing kernels of a barley plant carrying a mutation in the gene encoding HvGS1-3, e.g. any of the mutations described herein above in the section "Barley plant carrying a mutation in the GS1-3 gene";
- b) Optionally preparing a malt composition of at least part of said kernels, thereby obtaining a malt composition;
- c) Preparing an aqueous extract of said barley and/or malt composition;
- d) Processing said extract into a beverage.

Step b) may be performed as described herein above in the section "Plant products and methods of production thereof". And Step c) may, for example, be a step of preparing wort, i.e. the aqueous extract may be wort. Said wort may be any of the worts described herein above in the section "Plant products and methods of production thereof"; it may also be prepared as described in that section.

Step d) may comprise the step of fermenting said aqueous extract, e.g. fermenting said wort with yeast. Step d) may comprise the steps of:
- d-i) Heating the extract (e.g. in the presence of additional ingredient(s), such as hops);
- d-ii) Fermenting the heated extract, or the heated wort, in the presence of yeast;
- d-iii) Optionally adding one or more additional ingredient(s), thereby producing a beer.

Said additional ingredients may, for example, be $CO_2$ or aroma compounds.

Methods for producing beer are well known in the art, and thus the methods for producing a beverage may be any conventional method for producing beer involving use of the barley plant of the invention as starting material. For example, detailed descriptions of examples of suitable methods for malting and brewing can be found, including publications by Briggs et al. (1981) and Hough et al. (1982). Numerous, regularly updated methods for analyses of barley, malt and beer products are available, for example, but not limited to, American Association of Cereal Chemists (1995), American Society of Brewing Chemists (1992), European Brewery Convention (1998), and Institute of Brewing (1997). It is recognized that many specific procedures are employed for a given brewery, with the most significant variations relating to local consumer preferences. Any such method of producing beer may be used with the present invention.

The application also relates to the following embodiments:

10. A yeast carrying a mutation in the FDC1 gene resulting in a total loss of function of fdc1 activity, wherein the mutation results in formation of a stop codon at a codon encoding a Trp.

11. The yeast according to embodiment 10, wherein the yeast is *S. cerevisiae* and said *S. cerevisiae* carries a mutation resulting in formation of a stop codon at the codon encoding Trp159 of *S. cerevisiae* ScFDC1.

12. A method of producing a beverage, said method comprising the steps of:
- i. Providing wort;
- ii. Fermenting said wort with a yeast according to any one of embodiments 10 to 11;
- iii. Optionally further processing the fermented wort into a beverage.

SEQUENCE LISTING

| | |
|---|---|
| SEQ ID NO: 1 | NCBI: AFX60877.1 (HvGS1-3) |
| SEQ ID NO: 2 | GenBank accession number NCBI: JX878491.1 - CDS - HvGS1-3 |
| SEQ ID NO: 3-6 | Primers and probes distinguishing between the mutant allele and wild-type allele of HvGS1-3 at nucleotide position 860 |
| SEQ ID NO: 7 | Amino acid sequence of fdc1 of *S. cerevisae* (GenBank number NCBI: NM_001180847) |
| SEQ ID NO: 8 | Amino acid sequence of GASR7-A1 of *T. aestivum* (GenBank number NCBI: KJ000052). |
| SEQ ID NO: 9-12 | Primers and probes distinguishing between the mutant allele and wild-type allele of TaGASR7 at nucleotide position 273 |
| SEQ ID NO: 13-16 | Primers and probes distinguishing between the mutant allele and wild-type allele of ScFDC1 at nucleotide position 476 |
| SEQ ID NO: 17 | cDNA encoding BADH1 of *Hordeum vulgare* (HvBADH1) |
| SEQ ID NO: 18 | cDNA encoding mutant BADH1 of *Hordeum vulgare* (HvBADH1) |
| SEQ ID NO: 19 | Amino acid sequence of BADH1 of *Hordeum vulgare* (HvBADH1) |
| SEQ ID NO: 20-24 | Primers and probes distinguishing between the mutant allele and wild-type allele of TaGASR7 at nucleotide position 273 |
| SEQ ID NO: 25 | NCBI: KJ000052 - (TaGASR7 -A1) |
| SEQ ID NO: 26 | NCBI: NM_001180847 (ScFDC1) |

Unless otherwise stated, all GenBank accession numbers are given in relation to the GenBank database version as of 1 Jul. 2016.

EXAMPLES

The invention is illustrated by WS descriptions and examples, which should not be considered as limiting for the invention. Unless otherwise indicated, basic biochemical and molecular biological techniques were utilized for working with nucleic acids, proteins (including enzymes), and organisms.

All the work streams described below include e.g. specific numbers of grains used, specific concentration, and specific conditions for PCR etc. The skilled person will be able to adapt the specific examples provided to use of a different number of grains, different concentrations, different PCR conditions etc.

WS1: Preparing Randomly Mutagenized Cereal Grains

Step 1.1: Procedure of Mutagenesis

To induce mutations, kernels collected from barley plants were incubated in a solution of the $NaN_3$ mutagen, according to the details provided by both Kleinhofs et al. (1978) and those in U.S. Pat. No. 7,838,053 to K. Breddam et al. This procedure induces point mutations in the barley grains' gDNA, typically conferring randomly distributed codons for amino acid substitutions or translational stops of the protein-encoding DNA, i.e. leading to protein changes and truncations in proteins encoded by the mutagenized DNA. However, the methods of the invention also are useful for producing cereal plants with point mutations in the gDNA of non-protein coding regions, e.g. promoters, terminators and introns.

A total of 500 g of mutagenized grains, all of generation M0, were sown in a 7.5-m² plot in the field. The grains of generation M1 were, in some cases, multiplied in field plots—eventually yielding mutant plants of generation M2 or M3 (cf. FIG. 2A). Mutations in grains of generation M3 were expected to occur at a frequency corresponding to 0.9-2.3 per 10,000 grains (cf. Kleinhofs et al., supra).

WS2: Preparing an Ordered Library of Grains Derived from Mutated Cereal Plants

Step 2.1: Harvest of Cereal Plants, Threshing of Spikes

Every 7.5-m² "Field plot" (FP #01, FP #02, etc.; cf. FIG. 2B) in the field was divided into a number of "Field sub plots" (FSP #01, FSP #02, etc.; FIG. 2B, action labelled 1), each 0.45 m² large and containing ~300 individual plants. All spikes in one sub plot were manually harvested using a sickle, and subsequently collected in a single bag. The contents of individual bags were separately threshed, yielding bags labelled "Grain total", with each comprising ~6000 kernels (GT #01, GT #02, etc.; FIG. 2B, action labelled 2).

For purposes of clarity of description, and not by way of limitation, the following Step 2-relevant topics are detailed in the Examples below:

Example 1: Growing barley plants in "Field plots";
Example 2: Harvest of grains in individual "Field plots".

WS3: Determining Whether a Library Sample Contains Mutated Grains

Step 3.1: Splitting of Individual "Grain Total" Grain Pools into Two Fractions

Threshed grains in individual "Grain total" bags were each split into two fractions, of which "Sub grain total" samples consisted of ~1500 grains (labelled SGT #01, SGT #02, etc.; cf. FIG. 2C; action 1), the processing of which, detailed in Step 3.2 to Step 3.4 below. Processing of grains in "Sub grain total" fractions seeks, in broad terms, to determine which of said grain fraction(s) contain(s) the mutation(s) of interest. For reasons of clarity, but not of relevance for actions relating to Step 3, the remainder of a "Grain total" fraction, consisting of ~4500 grains, was processed as detailed in the description related to Step 4.

For purposes of clarity of description, and not by way of limitation, the following Step 3.1-relevant topic is detailed in the Examples below:

Example 3: Description of grains in "Sub grain total".

Step 3.2: Preparation of Flour Samples from Grains of "Sub Grain Total"

Each sub grain total sample containing 1500 grains—i.e. samples denoted SGT #01, SGT #02, etc.—was milled in a standard laboratory mill (cf. FIG. 2B, action 2), with thorough cleaning between applications, yielding the corresponding flour samples—denoted SFT #01, SFT #02, etc (cf. FIG. 2C).

For purposes of clarity of description, and not by way of limitation, the following Step 3.2-relevant topic is detailed in the Examples below:

Example 4: Making flour of grains derived from a sample of "Sub flour total".

Step 3.3: Preparation of gDNA from Flour Aliquots

Aliquots of individual "Sub flour total" samples, each 25 g and denoted "Aliquot of sub flour sample" (ASFT #01, ASFT #02, etc.), were dispensed into separate containers (cf. FIG. 2C, action 3).

gDNA was then extracted from each flour aliquot (cf. FIG. 2C, action 4), and each extracted gDNA was placed into one well of a microtiter plate with the samples denoted gDNA (GT #01), gDNA (GT #02), etc., denoting the specific "Grain total" origin of a sample. Alternatively, the extraction may be performed in wells of a microtiter plate.

For purposes of clarity of description, and not by way of limitation, the following topics related to Step 3.3 are detailed in the Examples below:

Example 5: Preparing 25-g flour aliquots (ASFTs);
Example 6: Preparing gDNA of ASFTs.

Step 3.4: Analysis of Samples Containing gDNA from GTs

Next, gDNA aliquots derived from individual samples of "Grain total" were transferred to a new 96-well microtitre plate (cf. FIG. 2C, action 5), occasionally including two negative control samples. Subsequent ddPCR analysis, e.g. as detailed in Example 7, may help identify samples containing gDNA of mutant plants.

For purposes of clarity of description, and not by way of limitation, the following topic related to Step 3.4 is detailed in the Examples section:

Example 7: ddPCR-based experiments with gDNA derived from ASFTs.

WS4: Finding Individual Grain(s) Characterized by a Mutation of Interest

Step 4.1: Specifics of a "Grain Library Pool" (GLP)

Given that an analysis, e.g. as detailed in Step 3.4 above, yielded a signal to indicate the presence of mutated gDNA in one or more of the 96 samples analyzed—i.e. those denoted gDNA (GT #01), gDNA (GT #02), etc. in FIG. 2C—it was considered highly likely that the 4500 grains of the "Grain total" fraction, labelled "Grain library pool" (GLP #01, GLP #02, etc.; FIG. 2D, action 2), comprised one or more grains with the identical mutation of interest. In the instant application, processing of said GLPs would relate to the ultimate efforts of finding a specific, mutated grain, which harbors the same mutation as that of a template molecule detected in a processed aliquot derived from a sample of "Grain total" (FIGS. 2B, 2C and 2D), and which further caused a mutant signal in the corresponding ddPCR analysis (as illustrated in FIG. 2C, action 5).

For purposes of clarity of description, and not by way of limitation, the following Step 4.1-relevant topic is detailed in the Examples section of the instant publication:

Example 8: Collecting grains for a "Grain library pool".

Step 4.2: Reducing a "Grain Library Pool" to a "Fraction of Grain Library Pool"

With an intact GLP sample containing 4500 grains derived from one specific GT (and given that the ddPCR-based analysis of gDNA, as illustrated in FIG. 2C, action 5, had indicated that said gDNA contained a mutation in the gDNA, it was normally sufficient to screen less than 12 individual grains for a specific gene mutation identical to that revealed by the analysis of Step 3.4. For that reason, a sample of 1200 grains of a GLP of interest was prepared (FIG. 2D, action 2), yielding a "Fraction of grain library pool", abbreviated FGLP. Eventually, a total of 96 samples were isolated, each consisting of 12 grains from a specific FGLP—each constituting a secondary sub-pool.

For purposes of clarity of description, and not by way of limitation, the following Step 4.2-topic is detailed in the following Examples of the instant publication:

Example 9: Obtaining a "Fraction of a grain library pool" from a "Grain library pool".

Step 4.3: Separating Grains and Corresponding Flour Samples

Each of the 12 grains in a sample prepared as described above in Step 4.2, were wounded by drilling a thin hole into the endosperms. While the wounded, but viable grains were transferred into one well of a deep-well microtitre plate (FIG. 2D, action 3), the flour liberated by drilling the same grains was pooled and transferred to a second microtitre plate (FIG. 2D, action 4). This procedure was carried out for the remaining 95 samples (keeping an identical numbering system of the two plates), yielding one microtitre plate with grain samples (denoted "Pools of drilled grains from fraction of library pool," abbreviated PDGLP; cf. FIG. 2D), and one microtitre plate with endosperm flour samples (denoted "Pools of flour from drilled grains," abbreviated PFGLP; FIG. 2D).

For purposes of clarity of description, and not by way of limitation, the following topics related to the instant Step 4.3 are detailed in the Examples below:

Example 10: Drilling of barley grains;
Example 11: Making "Pools of flour from drilled grains".

Step 4.4: Preparation of gDNA Derived from Endosperm Flour of Mutant Plants

Flour in each well of the microtitre plate, prepared as described above in Step 4.3, was separately subjected to extraction of gDNA (FIG. 2D, action 5). Said extraction employed a semi-automated procedure, based on the recommendations provided by the NucleoSpin 96 Plant II kit (Machery-Nagel), yielding "Pools of gDNA" in which an individual well of a microtitre plate contains gDNA derived from flour of 12 barley grains.

For purposes of clarity of description, and not by way of limitation, the following topics related to Step 4.4 are detailed in the Examples of the instant publication:

Example 12: Purification of gDNA from flour from drilled grains ("Pools of gDNA").

Step 4.5: Analysis of gDNA from Mutant Endosperms

Standard ddPCR analyses were performed with the samples of gDNA, prepared as described in Step 4.4 above, according to the recommendations provided by Bio-Rad for utilization of the QX200 droplet reader and droplet generator apparatus, using primer sets to test for specific mutations of interest. Provided that the analysis of gDNA derived from an individual well yielded signals to indicate the presence of mutated DNA in that sample (cf. FIG. 2D, action 6), there was a high likelihood that one or several of the grains from which the gDNA originated would contain the mutation of interest.

For purposes of clarity of description, and not by way of limitation, the following Step 4.5-related topic is detailed in the Examples section of the instant publication:

Example 13: ddPCR-based gDNA analysis of flour from drilled grains.

Step 4.6: Identification of the Mutant Kernel of Interest

While samples of the microtitre plate denoted PFGLP contained flour (cf. Step 4.3), the matching wells in the plates denoted PDGLP contained 12 corresponding, living grains. Accordingly, the next step was to isolate the sample consisting of the 12 grains of interest (FIG. 2D, action 7), and subsequently germinate these (FIG. 2D, action 8).

For purposes of clarity of description, and not by way of limitation, the following Step 4.6-topic is detailed in the Examples section of the instant publication:

Example 14: Germination of potential mutant plants.

Step 4.7: Trait Verification

A number of methods are available to the skilled researcher in order to determine whether a potential mutant possesses the expected features, i.e. traits of interest. In the instant case, gDNA was extracted from the germinated plantlets, identified and propagated as described in Step 4.6 above, and confirm by combined analyses utilizing ddPCR and DNA sequencing which of the 12 potential mutants actually harbor the mutation of interest (cf. FIG. 2D, action 9).

For purposes of description clarity, and not by way of limitation, the following topics related to Step 4.7 are detailed in the Examples section of the instant publication:

Example 15: Details of analyses, including ddPCR and DNA sequencing.

WS5: Generating and Using "Super-Pools" of gDNA

Step 5.1: Ultra High-Throughput Identification of Mutated Barley Grains

The instant invention also discloses the combined use of two different digital PCR analytical platforms, which improves the methods of identifying low-prevalence mutations. Herein, the RainDrop platform, commercialized by RainDance Technologies, was exploited to find DNA mutations in complex samples of gDNAs derived from mutant plants, while that of Bio-Rad provided ways to identify those grain extracts derived from individual barley mutants.

For purposes of description clarity, and not by way of limitation, the following topics related to Step 4.7 are detailed in the Examples section of the instant publication:

Example 16: Preparing "Super-pools" of gDNA;
Example 17: ddPCR with gDNA derived from "Super-pools".

In summary, simply to provide a short overview, WSs and corresponding examples are arranged the following way:

WS2:
Example 1: Growing barley plants in "Field plots";
Example 2: Harvest of grains in individual "Field plots".

WS3:
Example 3: Description of grains in "Sub grain total";
Example 4: Making flour of grains derived from a sample of "Sub flour total";
Example 5: Preparing 25-g flour aliquots (ASFTs);
Example 6: Preparing gDNA of ASFTs;
Example 7: ddPCR-based experiments with gDNA derived from ASFTs.

WS4:
Example 8: Collecting grains for a "Grain library pool";
Example 9: Obtaining a "Fraction of a grain library pool" from a "Grain library pool";
Example 10: Drilling of barley grains;
Example 11: Making "Pools of flour from drilled grains";
Example 12: Purification of gDNA from flour of drilled grains ("Pools of gDNA");
Example 13: ddPCR-based gDNA analysis of flour from drilled grains;
Example 14: Germination of potential mutant plants;
Example 15: Details of mutant plants identified through ddPCR-based screens.

WS5:
Example 16: Preparing "Super-pools" of gDNA;
Example 17: ddPCR with gDNA derived from "Super-pools".

EXAMPLES

Example 1: Growing Barley Plants in "Field Plots"

Barley grains were mutagenized with $NaN_3$ as described under WS1 herein above. Mutagenized barley grains were propagated in field plots of 7.5 $m^2$. In each plot, 250 g of grains were sown and grown to maturity.

Example 2: Harvest of Grains in Individual "Field Plots"

At harvest the field plots were divided into 15-17 subplots each containing approximately 300 plants. The plants were harvested by sickle and threshed and bagged—each subplot individually. Thus grains in one "Grain total" bag were derived from 300 plants.

Example 3: Description of Grains in "Sub Grain Total"

All grains of one "Grain total" sample were divided into 4 randomized fractions of equal size, using a grain riffle sample divider. Each fraction represents 25% of the total grain quantity of one "Grain total" sample. One of these fractions constitutes one "Sub grain total".

Example 4: Making Flour of Grains Derived from a Sample of "Sub Flour Total"

All grains of one "Sub grain total" sample were placed into a grain mill (Retsch, GrindoMix GM200). The grains were milled for 30 sec at 10.000 RPM. The resulting flour ("Sub flour total"; ~75 g) was placed into a paper bag and stored at 23° C.

Example 5: Preparing 25-g Flour Aliquots (ASFTs)

From one "Sub flour total" sample, an aliquot of 25 g of flour was weighed out. The 25 g flour aliquot (ASTF) was transferred into a paper bag and stored at 23° C.

Example 6: Preparing Purified gDNA of ASFTs

One 25-g flour aliquot (ASTF) was transferred into a 250-mL glass bottle and resuspended in 30 mL $H_2O$, followed by addition of 65° C.-heated, 70 mL 2% cetyltrimethyl ammonium bromide (CTAB) buffer containing 1.4 M NaCl, 20 mM $Na_2EDTA$, 100 mM Tris-HCl, adjusted to pH 8.0 with 1 M NaOH. After the solution was autoclaved, and subsequently supplemented with 250 µl of 10 mg/mL RNase A and 250 µl proteinase K, it was incubated with regular mixing to degrade RNA and protein. An aliquot of 50 mL was transferred to a 50-mL Falcon tube, followed by removal of insoluble precipitates by centrifugation at 4000 rpm for 10 min, where after 24 mL of the resulting supernatant was transferred to a new 50-mL tube.

After two consecutive extractions with chloroform (the first with 15 mL, the second with 12.5 mL), 15 mL of the aqueous phase containing nucleic acids, including gDNA, was transferred to a 50-mL tube containing 30 mL of a 0.5% CTAB buffer prepared with of 0.04 M NaCl, 50 mM Tris-HCl, adjusted to pH 8.0 with 1 M NaOH. The tube was inverted 6-8×, and incubated for 1 h at room temperature before centrifugation at 4000 rpm for 10 min. While the aqueous phase was discarded, the gDNA-containing precipitate was slowly dissolved in 10 mL of 1.2 M NaCl overnight at 8° C. Next, extraction was done with 10 mL chloroform before centrifugation at 4000 rpm for 15 min. Of the aqueous phase, 9.5 mL was combined with 5.5 mL isopropanol and the resulting sample gently inverted 6-8×, and then incubated at room temperature for 20 min, followed by precipitation of gDNA by centrifugation at 4000 rpm for 10 min.

The gDNA-containing precipitate was washed with 5 mL 70% ethanol in advance of centrifugation at 4000 rpm for 10 min—with the resulting supernatant discarded, while the gDNA precipitate was dried ~40 min at room temperature. After addition of 5 mL $H_2O$ and incubation for 30 min at 65° C. to resuspend gDNA, 500 µl of the gDNA derived from "Sub flour total" was transferred to a specific 2-mL deep-well of a corresponding microtitre plate. Said plate with samples of different gDNA samples derived from "Aliquots of individual SFTs" was denoted "Purified gDNA" and either utilized for long-term storage or experimental analysis.

Example 7: ddPCR-Based Experiments with gDNA Derived from ASFTs ddPCR was performed using a Droplet Digital PCR QX200 system (Bio-Rad), according to the instructions provided by the manufacturer. Sequence-specific primers and probes for wild-type and mutant alleles were purchased from Bio-Rad.

For analytical purposes, 5 µL of purified gDNA of separate ASFTs, cf. FIG. 2C, or of gDNA from yeast (prepared as described in Yeast WS3) was added to a 17-µL PCR mixture containing 11 µL 2×ddPCR Supermix for probes (No. dUTP; Bio-Rad), 900 nM target-specific PCR primer, 250 nM mutant detection and reference probes labelled with 6-carboxy-fluorescein—FAM and hexachlorofluorescein—HEX probes, respectively. The mutant detection probe specifically binds the target sequence comprising the mutation, whereas the reference detection probe specifically binds the wild-type sequence. The reaction mixture was loaded onto the AutoDG Droplet Generator (Bio-Rad), and droplet generation carried out according to the manufacturer's manual. The droplet emulsion was thermally cycled using standard PCR conditions: denaturation at 95° C. for 10 min, 40 cycles of PCR at 94° C. for 30 sec and 55° C. for 1 min, and a final extension at 98° C. for 10 min before storage of the microtitre plate at 8° C. PCR amplification in droplets was confirmed using the QX200 Droplet Reader (Bio-Rad). The analytical threshold was determined by comparing wild-type and no-template ddPCR results. All data were evaluated above threshold.

The data was analysed using the software QuantaSoft, version v1.7 (Bio-Rad).

Example 8: Collecting Grains for a "Grain Library Pool"

All grains of one "Grain total" sample were divided into 4 randomized fractions of equal size, using a grain riffle sample divider. Each fraction represents 25% of the total grain quantity of one "Grain total" sample. One "Grain library pool" contained the pooled grains of 3 of the fractions.

Example 9: Obtaining a "Fraction of a Grain Library Pool" from a "Grain Library Pool"

The "Fraction of a grain library pool" was established by sequentially removing 96 samples of 12 grains each from one "Grain library pool", wherein each sample of 12 grains constitutes a secondary sub-pool.

Example 10: Drilling Barley Grains

Grains from "Fraction of grain library pool" were separated in 96 aliquots, each consisting of 12 grains. Each 12-grain aliquot was placed on a piece of weighing paper, and then consecutively fixed with a pair of forceps while an engraving machine (Marathon-3, Saeyang Microtech) equipped with a 1.6-mm drill was used to drill a small, 2-3 mm deep hole into the endosperm. The rotating movement moved flour from the endosperm onto the top of the grain and the surrounding weighing paper. The 12-grain drilled samples were placed in separate 2-mL wells of a microtiter plate, yielding secondary sub-pools of drilled barley grains also denoted "Pools of drilled barley grains from fraction of library pool". (FIG. 2D, action 3). The drilled grains were stored at 20° C. until further analysis.

Example 11: Making "Pools of Flour from Drilled Grains"

The 96 flour samples, each with flour derived from 12 drilled barley grains (as detailed in Example 10), were transferred to separate wells of a 1.5-mL microtitre plate ("Pools of flour from drilled grains"; cf. FIG. 2D, action 4), keeping a sample numbering system matching that of the drilled grains.

Example 12: Purification of gDNA from Flour of Drilled Grains ("Pools of gDNA")

The flour pools of drilled barley grains, prepared as detailed in Example 11, were subjected to extraction of gDNA using a semi-automated DNA extraction procedure as detailed in the instructions of the NucleoSpin 96 Plant II kit (Macherey-Nagel). Accordingly, each well of the microtitre plate contained gDNA from flour of 12 grains (FIG. 2D, action 5).

Example 13: ddPCR-Based gDNA Analysis of Flour from Drilled Grains

While WS3 trials, cf. FIG. 2C and Examples 3-7, were designed to identify which individual sample(s) of 96 gDNA aliquots, in total representing gDNA of 6000 mutated grains, contained a nucleotide mutation of interest, the subsequent WS4-specific efforts, cf. FIG. 2D, were designed to pinpoint specific mutant grains.

As illustrated in in FIG. 2D, action 6, a primary effort was to determine which sample of gDNA from 12 distinct grains would yield a positive test result in a ddPCR analysis. Hence, utilizing identical reaction conditions and analysis parameters as provided in Example 7, it was possible to distinguish which well in a microtitre plate contained the gDNA of interest. Samples comprising one heterozygote mutant grain were defined as having a fractional abundance of 5% (±2.5%), those with 10% (±2.5%) comprising a homozygous mutant grain.

Based on the analytical efforts described above, it was possible to identify and select potential flour-pools, and accordingly the corresponding grain-pools with a nucleotide mutation of interest. Homozygous and heterozygous mutants were transferred to soil in large pots and transferred to the greenhouse for propagation. All negative plantlets were discarded.

Example 14: Germination of Potential Mutant Plants

Provided that the analysis of gDNA from flour of 12 barley grains yielded a mutant signal (cf. FIG. 2D, action 6), the corresponding grains of the "Pools of drilled grains from fraction of library pool" were germinated (FIG. 2D, actions 7 and 8).

Example 15: Details of Mutant Plants Identified Through ddPCR-Based Screens

The content of one "Pool of drilled grains from fraction of library pool", consisting of 12 drilled grains, was placed in a 9-mm Petri dish (prepared with 2 sheets of filter paper (8.5 mm; Whatman) to which 2 mL of $H_2O$ was added). Following germination phase for 96 h in the dark at 16° C., the grains were placed into soil and further grown in controlled conditions for 7 days. Then, 2×5 mm tissue sections were removed from the first leaves and placed into 0.2-mL tubes. 50 μL extraction solution (Sigma) was pipetted onto each leaf and incubated at 95° C. for 10 min. The samples were cooled to room temperature and mixed with 50 μL dilution solution (Sigma). gDNA samples were finalized by combining 10 μL of the extraction-dilution-mixture with 30 μL of $H_2O$.

For analytical purposes, 5 μL of purified gDNA was added to a 17-μL PCR mixture containing 11 μL 2×ddPCR Supermix for probes (No. dUTP; Bio-Rad), 900 nM target-specific PCR primers, 250 nM mutant-specific (6-carboxy-fluorescein—FAM) and wild-type-specific (hexachlorofluorescein—HEX) probes. The reaction mixture was loaded onto the AutoDG Droplet Generator (Bio-Rad) and droplet generation carried out according to the manufacturer's manual. The droplet emulsion was thermally cycled using standard PCR conditions: denaturing at 95° C. for 10 min, 40 cycles of PCR at 94° C. for 30 sec and 55° C. for 1 min, and a final extension at 98° C. for 10 min before storage of the microtitre plate at 8° C. PCR amplification in droplets was confirmed using the QX200 Droplet Reader (Bio-Rad). Test threshold was determined by comparing wild-type and no-template ddPCR results. All of the data obtained was evaluated above threshold. The data was analysed using the software QuantaSoft (version v1.7, Bio-Rad). One individual plantlet was considered a heterozygous mutant, provided that 50% of the total number of positive ddPCR events derived from the mutant probe (FAM). One individual plantlet was considered a homozygous mutant, when 100% of the total number of positive ddPCR events were derived from the mutant probe (FAM). Individual mutant plants were grown to maturity (cf. FIG. 1D, action 9).

Example 16: Preparing "Super-Pools" of gDNA

Simply, an aliquot (e.g. 50 μL) of each gDNA extract of all 94 "Sub-pools" of one library plate, were pooled into one "Super-pool".

In some embodiments the super-pools of gDNA are further enriched prior to performing the ddPCR analysis.

Thus, e.g. 2 μl of gDNA from a super-pool may be amplified in a standard PCR reaction comprising e.g. 10 μl 5×Q5 Reaction Buffer (New England Biolabs), 200 μM dNTPs, 0.02 U/μl Q5 High-Fidelity DNA Polymerase, 100 nM of target-specific forward PCR primer, 100 nM of target-specific reverse PCR primer, 100 nM of a blocking probe and water. The PCR mixture may then thermally be cycled using standard PCR conditions for approx. 20 cycles of PCR. This leads to the generation of an enriched super-pool of gDNA.

Example 17: ddPCR Analysis of gDNA Derived from "Super-Pools"

To reduce the chemical usage in parallel with obtaining improved throughput rates in screening efforts with mutated barley grains, there was developed a combined usage of two technologies, of which one was provided by RainDance Technologies (superior in droplet making) and the other by Bio-Rad (outstanding in the number of samples to be processed simultaneously). In general terms, the RainDance technology was utilized to identify specific, yet complex samples that contain gDNA templates from numerous mutant grains (herein below detailed in section "Procedure A"), while subsequent Bio-Rad-based analyses helped to identify single grains characterized by the mutation of interest (herein below described in "Procedure B").

Procedure A: RainDance-Based ddPCR with 16 "Super-Pools" of gDNA.

First, droplets for individual "Super-pools" (e.g. for 4 to 8 super-pools) were generated using the RainDrop Source instrument. The gDNA used for the RainDance-based ddPCR may be the combined gDNA extract or it may be the enriched super-pool of gDNA prepared as described in Example 16. E.g. a 20-μL aliquot of gDNA from one "Super-pool" or a 10 μl aliquot of the enriched super-pool of gDNA were combined with 25 μL Supermix for Probes (Bio-Rad); Droplet Stabilizer (RainDance); 900 nM of the target-specific forward primer; 900 nM of the target specific reverse primer; 120-250 nM of the wild-type detection probe (VIC); 250-440 nM of the mutant detection probe (FAM), and; $H_2O$ for adjustment to a total reaction volume of 50 μL. A total of 4-8 individual reaction mixtures, representing 4-8 individual "Super-pools" of gDNAs, were added to the 8-channel source chip (RainDance), and processed on the Source Instrument (RainDance). The entire procedure described herein above may be repeated for additional "Super-pools," bringing the total number of samples for subsequent analysis to 8 to 16.

Two 8-well strips containing the droplets generated from the reaction mixtures, described herein above, were sealed and the contents amplified as detailed in Example 9 herein. Thereafter, the amplified mixtures were transferred to the Sense Instrument (RainDance), and analyzed using the RainDrop Analyst data analysis software.

Those "Super-pools" that revealed higher signals related to the mutation of interest—as compared with the average signal of mutant events across all of the 16 "Super-pools"—were defined as containing potential mutant-derived gDNA.

Procedure B: Bio-Rad-Based ddPCR Analysis of "Super-Pools".

ddPCR analysis was performed on aliquots of each of the 96 gDNA samples that constituted a "Super-pool" of interest, as detailed in Procedure A herein above, had indicated the presence of a mutant template. The analysis was carried out as that described herein above for WS3 and WS4.

Particularly, the data analysis aimed at selecting the grain pool comprising the predetermined mutation of interest. The datasets on threshold were individually defined with respect to the plots of all data points for the full plate. Analysis categories—including, but not limited to, plots of target concentration, fractional abundance, and identified mutation events—were individually assessed with respect to candidate selection.

The fractional abundance may be determined as: [Signal of ("mutant detection probe")] divided by [Signals of ("reference detection probe"+"mutant detection probe")].

Samples were assumed to contain mutant DNA provided that the following properties were observed:
An increased fractional abundance;
An increased level of mutant droplets, or;
An increased number of mutant events at a scale of 50%, or higher, above average.

Example 18: ddPCR-Based Screening for Barley Mutants with Specific Mutations in the Gene for Glutamine Synthetase GS1-3

A barley plant carrying a specific mutation was identified using the methods described in the Workstreams and Examples herein above. As described, the methods can be used for identification of any mutant. Identification of a specific mutation, G→A, leading to the substitution of a Gly to Asp acid residue at position 287 of sequence for barley glutamine synthetase 1 isoform 3 (HvGS1-3).

Glutamine Synthethase

Glutamine synthethase 1 (GS1) is a key enzyme involved in nitrogen assimilation in higher plants by catalysing the condensation of ammonium or ammonia and glutamate into glutamine. On nitrogen-rich soils, over-availability of nitrogen can lead to increased nitrogen accumulation during grain filling in barley, thus negatively impacting the quality of the malt. Knock-out mutations in GS1 can lead to severe growth deficiencies, highlighting the importance of the enzyme for overall plant fitness (Tomoyuki Yamaya and Miyako Kusano, 2014). Three isoforms of GS1 are known in barley (HvGS1-1, HvGS1-2, HvGS1-3). Of the three barley isoforms, HvGS1-3 is primarily active in the developing grain and upregulated under high ammonium conditions. A mutation strategy was designed with the aim of maintaining optimal plant development, yet reduced grain nitrogen accumulation ability. The mutation strategy focused on amino acid substitutions that reduce enzymatic activity of GS1-3. A suitable amino acid substitution was identified at position 287 in the protein sequence (Protein Seq ID, NCBI: AFX60877.1—provided herein as SEQ ID NO:2). Changing the codon GGC (nucleotide 859, 860, 861; CDS of GenBank number NCBI: JX878491.1—provided herein as SEQ ID NO:1) to GAC, leads to an amino acid exchange from glycine to aspartic acid at position 287 in the protein sequence (Protein Seq ID, NCBI: AFX60877.1). This amino acid change will introduce a negatively charged amino acid into the protein sequence. GS1-3 is a decamer consisting of two rings composed of 5 subunits, with amino acid residue 287 located at the interphase between the two rings and away from the active site. Thus, it is put forward that the introduction of a negatively charged amino acid would not impact the overall ability to catalyse its reaction, but instead may reduce enzymatic activity through structural changes in the assembly of the decamer.

ddPCR Assay

A unique ddPCR assay was designed, specifically to distinguish between the mutant allele and wild-type allele of HvGS1-3 at nucleotide position 860 in the wild-type coding sequence (GenBank number NCBI: JX878491.1). The mutant detection probe was complementary to the coding sequence, containing an A base at nucleotide position 860. The reference detection probe was complementary to the coding sequence, containing a G base at nucleotide position 860. Two flanking primers were designed to amplify the genomic sequence surrounding nucleotide 860 in the coding sequence.

The following primers and probes were designed specifically for the HvGS1-3 locus:

```
Target-specific forward primer (SEQ ID NO: 3):
5'-GTGATCAAGAGGGCGATCAA-3';

Target-specific reverse primer (SEQ ID NO: 4):
5'-CAAGTCTCAACTCGCCGTAT-3';

Mutant-specific detection probe (SEQ ID NO: 5):
5'-AAGACAACGAGCGC-3'-labelled with
6-carboxyfluorescein (FAM);
```

-continued

```
Reference-specific detection probe (SEQ ID NO: 6):
5'-AAGGCAACGAGCGC-3'-labelled with
hexachlorofluorescein (HEX).
```

A pool of randomly mutagenized barley grains was prepared as described in WS1 herein above, followed by preparation of an ordered library.

Determining Whether a Library Sample Contains Mutated Grains (WS3)

The next step, in general, was to determine whether the library contained mutated grains, essentially as described for WS3 and in Example 7 herein above with the following specifics:

- The screening was performed with a total of 376 GLPs (i.e. 376 sub pools), representing approximately 120,000 mutated barley plants. The ddPCR was performed essentially as described in Example 7;
- One 5-µL gDNA sample derived from gDNA (GT #377-GT #470) was added to each well containing 17 µl of the PCR reaction mixture and mixed thoroughly by pipetting up and down.
- The microtiter plate for PCR was loaded onto the QX200 Droplet Reader (Bio-Rad) for droplet analysis. The data obtained was analysed using the software QuantaSoft (version v1.7, Bio-Rad). The threshold was determined using the 2-D plot, set at 2700 and 1500 for amplification for Channel 1 and Channel 2 amplitude, respectively. Comparison of the individual values for fractional abundance showed that gDNA (GT #380) provided higher signals than any other sample with respect to mutant detection. The fractional abundance of gDNA (GT #380) was 0.089% compared to 0.0077%, the latter representing the average fractional abundance of all of the 94 tested gDNA samples.

Finding Individual Grain(s) Characterized by a Mutation of Interest (WS4)

Individual barley grains carrying a gene mutation were identified essentially as described herein above in WS4, including the following consecutively ordered specifics:

1. Based on the analysis of gDNA derived from GT #377-GT #470 with a HvGS1-3-specific ddPCR assay, it was considered highly likely that the 4500 grains of GLP #380 [corresponding to positive sample gDNA (GT #380)], would comprise one or more grains with the gene mutation of interest.
2. FGLP #380 was established by sequentially removing 96×12 grain samples from GLP #380. Each 12-grain aliquot was placed on a piece of weighing paper, and then consecutively fixed with a pair of forceps, at the same time using an engraving machine (Marathon-3, Saeyang Microtech) equipped with a 1.6-mm drill to drill a small, 2-3 mm deep hole into the endosperm. The rotating movement moved flour from the endosperm onto the top of the grain and the surrounding weighing paper. The 12-grain drilled samples were placed in separate 2-mL wells of a microtiter plate, yielding the secondary sub-pool of drilled barley grains PDGLP #380. The 96 flour samples, each with flour derived from 12 drilled barley grains, were transferred to separate wells of a 1.5-mL microtitre plate (PFGLP #380) keeping a sample numbering system matching that of the drilled grains.
3. Next, PFGLP #380 was subjected to extraction of gDNA using a semi-automated DNA extraction procedure as detailed in the instructions of the NucleoSpin 96 Plant II kit (Macherey-Nagel). Accordingly, each well of the microtitre plate contained gDNA from flour of 12 grains.
4. gDNA derived from PFGLP #380 was analysed as described above. The data was analysed using the software QuantaSoft (version v1.7, Bio-Rad). The threshold was determined using the 2-D plot and set at 2700 for Channel 1 amplitude and 1500 for Channel 2 amplitude. Comparison of the individual values for fractional abundance showed that none of the samples of PFGLP #380 contained a mutant grain. As it was considered highly likely that GLP #380 contained a mutant grain, it was decided to prepare and analyse additional samples by establishing a second FGLP (FGLP #380-2). This resulted in in the preparation of PDGLP #380-2 and PFGLP #380-2. gDNA from PFGLP #380-2 was analysed as described above. The data was analysed using the software QuantaSoft (version v1.7, Bio-Rad). The threshold was determined using the 2-D plot and set at 2700 for Channel 1 amplitude and 1500 for Channel 2 amplitude. Three individual wells in the microtitre plate (C02, F04, F05) were identified that showed a fractional abundance of 4.02%, 4.11% and 5.55%, all indicating the presence of three individual heterozygous mutants in 3 independent wells of PDGLP #380-2.
5. All 12 grains from well C02 and F04 of PDGLP #380-2 were germinated. Leaf material from all 24 plantlets was harvested and subjected to DNA extraction using REDExtract (Sigma Aldrich). The gDNA derived from leaf samples was analysed as described above. The data was analysed using the software QuantaSoft (version v1.7, Bio-Rad). The threshold was determined using the 2-D plot and set at 2700 for Channel 1 amplitude and 1500 for Channel 2 amplitude. One plantlet derived from well C02 of PDGLP #380-2 showed a fractional abundance of 41%, confirming the presence of a heterozygous mutant. One plantlet derived from well F04 of PDGLP #380-2 showed a fractional abundance of 39.6%, confirming the presence of a heterozygous mutant.
6. Additional trait verification was performed using direct sequencing on both identified mutants and a reference sample. DNA was extracted from leaf material using the REDExtract DNA extraction procedure (Sigma Aldrich). For the sequencing analysis a 50-µl PCR reaction was prepared that contained 1-µl of purified gDNA, 20-µl REDExtract (Sigma Aldrich), 500 nM of a target specific forward primer, 500 nM of a target specific reverse primer and water. The samples were thermally cycled using the following PCR conditions: denaturation at 94° C. for 2 min, 38 cycles of PCR at 94° C. for 45 sec, 58° C. for 45 sec and 72° C. for 45 sec, and a final extension at 72° C. for 5 min before storage of the PCR plate at 8° C. Individual PCR products were purified using the NucleoSpin Gel and PCR clean up kit. All samples were sequenced using a target specific forward primer and a target specific reverse primer.
7. Both plantlets that were identified positive for the mutation in the ddPCR analysis was heterozygous with respect to the genotype at the predetermined genomic location. The reference sample showed a homozygous wild-type genotype at the same location.

Example 19: Analyses of Recombinant Forms of Barley Glutamine Synthase

Synthesis of three recombinant HvGS1-3 variants utilized E. coli host cells, followed by enrichment of the enzyme to a high degree of purity by affinity purification. The following variants were expressed in E. coli:

Q: Wild-type reference—SEQ ID NO:1;
3864: SEQ ID NO:1 with an amino acid exchange G287D, i.e. corresponding to the mutant protein expressed by a mutant barley plant (identified as described in Example 18).
LR: SEQ ID NO:1 with an amino acid exchange D300N, i.e. an enzyme variant in which the change is expected to have little impact on enzymic activity.

Activities of the three HvGS1-3 variants were determined by following the synthesis of glutamyl hydroxamate from glutamate, hydroxylamine and ATP in presence of the enzyme. Enzyme kinetics were determined for all three HvGS1-3 variants at different concentrations of glutamate and hydroxylamine, with the results shown in Table 1 and Table 2, respectively.

Whilst $k_{cat}$ and $k_{cat}/K_M$ for HvGS1-3 Q and LR were similar, HvGS1-3 3864 consistently revealed values that were one or two orders of magnitude lower compared to the other two variants. The kinetic data indicated that the mutation identified in HvGS1-3 3864, Gly 287 to Asp, had severe impact on the binding and utilisation of either substrate in this variant. Kinetic values on ATP binding and utilization could not be determined due to a high degree of variability in absorbance at high substrate concentrations of the nucleotide.

TABLE 1

Enzyme kinetics of HvGS1-3 variants in the presence of distinct concentrations of glutamate. Concerning Q, LR and 3864, numbers in parentheses refer to the total amount of protein, in µg, of the reaction.

|  | Q (0.1) | LR (0.1) | 3864 (0.5) |
|---|---|---|---|
| $K_M$ (mM) | 8.68 | 13.93 | 63.41 |
| $v_{max}$ (mM min$^{-1}$ µg$^{-1}$) | 0.66 | 0.58 | 0.20 |
| $k_{cat}$ (min$^{-1}$) | 6.6 | 5.8 | 0.4 |
| $k_{cat}/K_M$ (mM min$^{-1}$) | 0.76 | 0.42 | 0.01 |

TABLE 2

Enzyme kinetics of HvGS1-3 variants in the presence of distinct concentrations of the substrate hydroxylamine Concerning Q, LR and 3864, numbers in parentheses refer to the total amount of protein, in µg, of the reaction.

|  | Q (0.1) | LR (0.1) | 3864 (0.5) |
|---|---|---|---|
| $K_M$ (mM) | 2.79 | 2.58 | 3.68 |
| $v_{max}$ (mM min$^{-1}$ µg$^{-1}$) | 0.64 | 0.53 | 0.11 |
| $k_{cat}$ (min$^{-1}$) | 6.4 | 5.3 | 0.22 |
| $k_{cat}/K_M$ (mM min$^{-1}$) | 2.29 | 2.05 | 0.06 |

In order to determine whether oligomerisation of the GS1-3 complex was affected in either of the two variants as compared to Q, an aliquot of purified HvGS1-3 was first run over a size-exclusion column. All three variants had a major peak at the same elution volume Below is described a detailed, 6-step account on the experiments that were utilized in order to obtain the results described in this example.

Step 1: Design of the HvGS1-3 Gene Sequence for Heterologous Gene Expression

The coding sequence of barley glutamine synthetase isoform GS1-3 (HvGS1-3), deposited at GenBank under the accession number JX878491.1, was used as a basis for synthesis of 3 corresponding gene sequences (GenScript, China), representing either wild-type HvGS1-3 (Q) and two forms containing mutations (3864 or LR). The wild-type GS1-3 gene and protein sequences are provided herein as SEQ ID NO:1 and SEQ ID NO:2, respectively. The protein-coding DNA sequences of all three variants were inserted into the E. coli expression plasmid pET-28a(+) purchased from MerckMillipore (Germany), followed by transformation of E. coli cells of strain BL21(DE3), using standard methods.

Step 2: Heterologous Expression of HvGS1-3

E. coli BL21(DE3) cells transformed with HvGS1-3 Q or its variants in pET-28a(+) were used. The bacteria were cultivated in LB medium containing 30 µg/mL kanamycin under standard conditions. Gene expression was induced with addition of 250 µM isopropyl β-D-1-thiogalactopyranoside (IPTG, Sigma-Aldrich). Expression was carried out at 37° C. for 4 h at 120 rpm. The cells were harvested by centrifugation at 4,000×g for 15 min at 8° C. While the supernatant was discarded, cell pellets were re-suspended in 10 mL of buffer A (20 mM Tris-HCl, pH 8.0, 500 mM NaCl, 1 mM MgCl$_2$). Re-suspended cells were frozen at −20° C. until further use.

Step 3: Cell Lysis of E. coli BL21(DE3) Cells after Recombinant Gene Expression

Transformed, frozen E. coli BL21(DE3) cells were first thawed, and then disrupted using a Vibra cell sonicator (Sonics & Materials Inc., USA) at 30% amplitude for 90 sec, with 5-sec pulses and 5-sec breaks, on wet ice. After sonication, DNA was digested for 10 min using 5 µg/mL DNaseI (Sigma-Aldrich). Lysed cells were removed by centrifugation for 10 min at 13,000×g and 4° C. The supernatant was passed through a 0.45-µm filter of a syringe into a new tube.

Step 4: Enrichment of HvGS1-3 by Immobilised Metal-Affinity Chromatography

A 1-mL immobilised metal-affinity chromatography (IMAC), charged with a nickel solution, was washed with five column volumes double-distilled water and equilibrated with the same volume of buffer A (the composition of which detailed above). The filtered, soluble fraction was injected manually into an equilibrated column using a syringe, with unbound material collected and kept at 4° C. Loosely bound column material was washed-off using buffer A, containing 50 mM imidazole (Sigma-Aldrich), over 10 column volumes (CV). HvGS1-3 was eluted and collected under similar conditions, using buffer A, containing 400 mM imidazole, over 10 CV. The eluted protein solutions were diafiltrated 4× on a centrifugal filter unit made of regenerated cellulose having a nominal molecular cut-off of 10,000 (Millipore, Ireland), against buffer A [by centrifugation at 3,000×g (SL-16R) at 8° C. for 20 min, to remove excess imidazole].

Step 5: In Vitro Activity Assay of Recombinant HvGS1-3

An adaptation of the activity assay described by Wellner and Meister (1966) was used to determine changes in the activity of the two HvGS1-3 variants (as compared to that of HvGS1-3 Q). A 50-µL reaction contained 100 mM Tris-HCl, pH 8.0, 50 mM MgCl$_2$, 20 mM ATP, different concentrations of γ-glutamate hydroxylamine (when L-glutamate was varying; otherwise 50 mM), different concentrations of L-glutamate (when glutamate hydroxylamine was varying; otherwise at 50 mM). Reactions were set-up in a half-area, flat-bottom 96-well microplate (Corning, USA), equilibrated to 37° C. The reaction was initiated by the addition of purified HvGS1-3 at a final concentration of 1 or 5 µg/mL. After 30 min, the reaction was stopped by addition of 50 µL 370 mM Fe(III)Cl$_3$, 200 mM TCA, 670 mM HCl. A$_{540}$ nm was then measured from the bottom on a SpectraMax 340PC384 microplate reader (Molecular Devices, USA), using path correction to account for minor differences in volume. The data was plotted using GraphPad Prism (version 4, GraphPad Software, USA).

Step 6: Size-Exclusion Chromatography

Equal amounts of the three HvGS1-3 variants were loaded individually onto a 10/300 size-exclusion column containing Superdex 200 (GE Life Sciences, USA), and equilibrated in buffer A on an ÅKTA FPLC (GE Life Sciences). Elution of bound protein was carried out at 0.5 mL/min and protein elution was followed by measuring $A_{280}$.

Example 20: ddPCR Analyses with gDNA Derived from Mutagenized Yeast Cells

For purposes of description clarity, and not by way of limitation, the following topics are detailed in the instant example:
Part 1: Preparing a randomly mutagenized yeast culture
Part 2: Preparing an ordered library
Part 3: Identification of the well containing gDNA with a predefined mutation
Part 4: Enriching yeast cells characterized by a predetermined mutation WS1: Preparing a Randomly Mutagenized Yeast Culture
Step 1.1: Procedure of Mutagenesis To induce mutations, yeast strain is subjected to treatment by MNNG (Methylnitronitrosoguanidine) according to the protocol described in Methods in Molecular Biology, Yeast Protocols, V. 313, 2006).

MNNG is a mutagen known to alkylate guanidine or thymine of the gDNA that is followed by G·C pair transition to A·T upon replication of gDNA. The method described in this section is aimed to identify the point mutation at the gene of interest that alters the defined amino acid codon to premature stop codon. The skilled person will be able to adapt the method to identification of other kinds of mutations. The point mutation thus leads to the truncated and correspondingly non-functional or defective protein. Desirable point mutations to create stop codon are defined based on the sequence of the targeted gene/protein. Other point mutations affecting regulatory regions of the gene of interest are identifiable by this method as well.

Mutagenesis is performed on the yeast culture e.g. with the total cell count $2\times10^7$. Mutator state of the yeast cells for mutagenesis is determined and adjusted to ensure the desirable mutation rate. The mutagenesis conditions are typically adjusted to give 60-70% survival rate. The mutagen concentration and time of the exposure vary depending on the yeast strain.

WS2: Preparing an Ordered Library
Step 2.1: Cell Viability

Viable cell titer is determined and all mutagenized yeast cells are inoculated in aliquots into 96 wells plates with YPD using Biomek FXp robot. 3000-5000 viable single cells are inoculated per well.

WS3: Identification of the Well Containing gDNA with a Predefined Mutation
Step 3.1: Making a Library of Mutagenized Yeast Cells Mutagenized yeast cells inoculated in 96-well plates from Step 1.1 are considered as a total library that contains targeted mutated yeast. Yeast cells are incubated for 3 d to allow growth saturation. The library is amplified by re-inoculation into minimal growth medium with Biomek FXp robot (copying step) to use for gDNA isolation after 3 days of growth. The rest of the yeast cell suspension in 96-well plates is preserved with glycerol (15% final concentration) at −80° C. for downstream application to isolate the desirable mutant yeast.

Step 3.2: Isolation of gDNA from Yeast

To prepare gDNA, yeast cells are transferred into a DNA isolation 96-well plate and subjected to the procedure of the DNA isolation using robotics (Biomek FXp, Agencourt DNAdvance kit and protocol from Beckman Coulter). The procedure follows the manufacturer's instructions, with an additional step using Lyticase enzyme to digest the yeast cell wall and break the cells. The protocol employs precipitation of gDNA with magnetic beads. gDNA in a 96-well plate is used for downstream application to identify the positive pool for the predetermined mutation. The DNA concentration is measured using the 96-well plate reader, with the concentration of the DNA adjusted to 25 ng/5 µL and used directly for the ddPCR. The original concentrated DNA in 96-well plates is stored for later use.

Step 3.3: Analysis of the Samples by ddPCR gDNA prepared at Step 2.2 in 96-well plate format is quantified and concentration is adjusted to 25 ng/5 µL. Positive and negative control DNA samples are included.

Subsequent ddPCR analysis is performed on each gDNA sample essentially as described in the Example 7. At this stage an array of probes recognizing different point mutations at several or all the possible positions in the gene sequence, which create a premature stop codon may be applied to enhance the chance of the mutant identification. The method allows identification of the wells positive for desirable mutation, i.e. wells comprising yeast carrying the desirable mutation.

WS4: Enriching Yeast Cells Characterized by a Predetermined Mutation
Step 4.1: Preparing a Pooled Yeast Library A 96-well plate comprising the well positive for the mutation is defrosted and yeast cells revived by inoculating of the content of the positive well into fresh YPD broth (1:10) and incubated for 4-6 h with rotation at room temperature. To ensure the absence of further proliferation of the yeast cells, the revived yeast culture is stored in a refrigerator until downstream plating and successful isolation of the pure mutant culture is complete. Before plating, viable yeast cells are counted and diluted with PBS containing 1 mM EDTA, and subsequently plated on Qpix square dishes with YPD agar to get 2000-3000 colonies per plate. The number of plates to prepare this way depends on the titer of viable yeast cells after revival from the frozen stock and on the progress of the mutant identification. For example 10-12 Qpix plates may be inoculated with up to 50,000 single cells that give rise to individual colonies. Identification of the positive pool described in Part 3 with the ratio of the wild-type:mutant being up to 1:5000 suggests that among 50,000 single cells at least 10 cells are the targeted mutant. Growth of the colonies is monitored to ensure the proper size and distance between colonies to be able to pick the individual colonies with Qpix robot. Once colonies are ready for picking, library of 96 well plates with YPD grown yeast cells are created in the following manner: colonies from all Qpix plates are collected randomly into ten 96-well plates, thus each well contains pool of 50 colonies with the minimal potential ratio of wild-type:mutant equivalent to 1:50. These plates are processed further to isolate gDNA and also to make frozen stock and stored at −80° C. for further downstream application, as described in Step 3.1 (WS3).

Step 4.2: Isolation of Yeast gDNA from Pooled Library

To prepare gDNA from pools of 50 isolated colonies, yeast cultures in a 96-well plate obtained in Step 3.1 are re-inoculated into fresh minimal growth medium. Once growth is sufficient, the yeast cultures are subjected to the procedure of the DNA isolation using robotics, as described in the Step 3.2 (WS3). The concentration of DNA is measured using the 96-well plate reader, and the concentration of the DNA is adjusted to 25 ng/5 µl, and an aliquot used directly for the ddPCR. The original concentrated gDNA in 96-well plates format is preserved. gDNA in a 96-well plate is used for downstream application to identify the positive pool/well with the predetermined mutation. A total of 10 96-well plates with gDNA are prepared.

Step 4.3: Analysis of the Samples by ddPCR gDNA prepared in Step 3.2 in 96-well plate format is quantified and the concentration is adjusted to 25 ng/5 µL. Positive and negative control DNA samples are included. Subsequent ddPCR analysis is performed on each gDNA sample, essentially as described in Example 7. If multiple probes are used in Step 3.3, then at this stage only probe(s) that gave positive identification of the positive pool at Step 3.3 are applied. The method allows identification of the positive sub-pool(s) with a predetermined mutation.

Step 4.4: Preparing a Single-Colony Yeast Library

A frozen 96-well plate with positive well(s), identified in Step 4.3, is used to plate out for single colonies growth. A yeast culture from a positive well is inoculated into fresh YPD broth and is grown overnight. 1000 cells are plated on YPD agar (Qpix square dish format) to yield single colonies. Grown colonies are picked by Qpix robot into ten 96-well plates with YPD broth as a growth medium. These plates are processed further to isolate gDNA and also to make frozen stock for further downstream application, as described in Step 3.1 (WS3).

Step 4.5: Isolation of gDNA from a Library of Single Colonies gDNA is prepared as described in Step 4.2.

Step 4.6: Analysis of the Samples by ddPCR gDNA prepared in Step 4.5, i.e. in 96-well plate format is quantified and the concentration adjusted to 25 ng/5 µL. Positive and negative control DNA samples are included. Subsequent ddPCR analysis is performed as described in Example 7. At this stage, only probe(s) that gave positive identification in Step 3.1 are applied. The method allows identification of the pure yeast culture with the predetermined mutation. The method allows determining the homozygous or heterozygous status of the isolate.

Step 4.7: Isolation of a Pure Culture of Mutant Yeast

To make the stock of the mutant yeast, a yeast suspension from the positive well(s) is plated out on the YPD agar to get growth of the isolated colonies. 3 colonies are picked manually and processed further as biological replicas.

Step 4.8: Sequencing of the Target Gene or a gDNA Stretch of Interest

Yeast mutant isolates with the identified mutation from Step 4.7 (WS4) are used for isolation of gDNA, followed by specific PCR, cloning of the obtained DNA fragment and performing DNA sequencing to confirm the identity of the mutation.

Step 4.9: Functionality of the Mutation

The yeast mutant with a homozygous mutation of interest is used directly to confirm that the mutation has the expected effect. If a heterozygous status is determined, and found insufficient to provide the expected effect, then mutagenesis is either repeated, or the yeast isolate undergoes sporulation followed by segregation of the mutation to confirm the homozygous status and mutant phenotype. The yeast isolate with the mutation of interest is used directly for the applied purpose, or it is used in the yeast breeding to control the desirable phenotype.

Example 21

In *Saccharomyces cerevisiae*, the ferulic acid decarboxylase Fdc1 is essential for the decarboxylation of aromatic carboxylic acids including cinnamic or coumaric acid. The decarboxylation reaction converts the substrates to their corresponding vinyl derivatives, some of which are known to be flavor active compounds. During beer fermentation for example, Fdc1 converts ferulic acid from the wort to 4-vinyl guaiacol, which becomes noticeable as clove-like notes in the final beer. While these notes are typical for certain beers, especially German wheat beers, they are considered phenolic off-flavours (POF) in others including lager beers. Here identification of *S. cerevisiae* carrying a nonsense mutation in the gene ScFDC1 is by non-GMO methods is described. The identified yeast is expected to be a POF negative yeast strain.

In food industry, the use of molecular genetic techniques to modify selected organisms is undesirable, and people rely on using classic random mutagenesis techniques and time-consuming screenings to identify strains of interest. The method described below depicts a less time-consuming technique to identify strains carrying a selected mutation of interest within a population of randomly mutagenized organisms, More specifically, in this example yeast strains carrying a specific nonsense mutation (W159*) resulting from a G to A transition at position +476 of the ScFDC1 gene in the *S. cerevisiae* var. *diastaticus* strain FS0105 is described. The sequence of the ScFDC1 gene is available at GenBank under number NCBI: NM_001180847, the cDNA sequence is provided herein as SEQ ID NO:26 and the amino acid sequence of fdc1 is provided as SEQ ID NO:7.

WS1: Preparing a Randomly Mutagenized Population of FS0105 Yeast Cells.

Step 1.1: EMS Mutagenesis on Strain FS0105.

To induce mutations, the yeast strain FS0105 was subjected to treatment by ethyl methanesulfonate (EMS) according to the protocol described in "Methods in Yeast Genetics" (CSHL Press, 2000). In brief, strain FS0105 was grown overnight in YPD medium into stationary phase. Cells were harvested by centrifugation and washed once with sterile distilled water and once with 0.1 M sodium phosphate buffer (pH 7). Cells were finally re-suspended in 0.1 M phosphate buffer to about $2 \times 10^8$ cells/ml. 30 µl EMS were added to 1 ml of cells in a 2 ml safe-lock reaction tube, and cells were incubated for approx. 75 minutes at 30° C. and 1000 rpm on an Eppendorf Thermomixer comfort (1.5 ml), which usually resulted in a killing rate of ~60-80% for strain FS0105. To stop the mutagenesis, cells were pelleted by brief centrifugation and washed three times with freshly prepared, sterile 5% sodium thiosulfate solution, and one time with sterile, distilled water. Cells were finally re-suspended in 1 ml YPD and incubated for 1 hour at 30° C. and 1000 rpm on an Eppendorf Thermomixer comfort (1.5 ml). At this step cells could be stored at 4° C., or were immediately used for downstream processes, e.g. determining killing rates by plating on complex medium.

Literature suggested that putting mutagenized yeast cells under selective pressure immediately after mutagenesis would result in a significant increased number of mutations per cell (Lada et al., 2013; Den Abt et al., 2016), which could significantly reduce the number of yeast cells to be screened in order to identify a mutation of interest. Therefore, approx. $2 \times 10^7$ live but mutagenized cells per plate were plated on SD medium plates containing 2 µg/ml of the herbicide metsulfuron methyl, and incubated the plates for several days at 30° C. until herbicide resistant colonies would show on the selective plates. We aimed for approx. 50,000 herbicide resistant colonies overall. To further increase the number of mutations per cell, we washed the herbicide resistant cells with sterile 0.1 M sodium phosphate buffer (pH 7) off the plates, diluted them to approx. $2 \times 10^8$ cells/ml and repeated the EMS mutagenesis as described above. This cycle of mutagenesis and selection was repeated four times in total.

WS2: Preparing a Random Library of Randomly Mutagenized FS0105 Yeast Cells.

Step 2.1: Creating a Total Random Library of Mutagenized FS0105 Yeast Cells.

After the fourth and final round of EMS mutagenesis (see Step 1.1), viable cell titer was determined by plating respective dilutions on complex medium plates. Subsequently, approx. 1,200-1,500 live cells/plate were spread onto YPD plates, and petri dishes were incubated at 30° C. for three days. From 96 separate plates, cells were washed off with 3 ml 0.1 M sodium phosphate buffer each, to form 96 "library pools". Approx. $5 \times 10^7$ cells from these library pools were subsequently used for DNA isolation (see below), while the remaining cells were spun down, re-suspended in 40% glycerol/10% YP, and frozen down at −80° C. to establish a "total random library" of 96 library pools containing approx. 120,000-150,000 EMS mutagenized FS0105 clones overall.

WS3: Identifying Library Pools Containing Clones with a Selected Scfdc1 Nonsense Mutation in the FS0105 Total Random Library.

Step 3.1: Yeast Genomic DNA Isolation from the FS0105 Total Random Library.

Genomic DNA from each pool of the total random library was isolated using the PureLink® Pro 96 genomic DNA Kit (invitrogen) and an EveryPrep™ Universal Vacuum Manifold (invitrogen) according to the manufacturer's instructions. The DNA concentration of each sample was determined using a NanoDrop 1000 3.8.1 and DNA solutions were adjusted to a final concentration of 5 ng DNA/µl with sterile DNAse free water. DNA samples were stored in a 96 well PCR plate at −20° C. until further use.

Step 3.2: Analysis of the Library Pool gDNA Samples by ddPCR.

A unique ddPCR assay was designed, specifically to distinguish between the mutant allele and wild-type allele of ScFDC1 at nucleotide position +476 in the wild-type coding sequence of strain FS0105. The corresponding TGG codon is identical to the ScFDC1 sequence of the common laboratory reference strain S288C at this position (GenBank number NCBI: NM_001180847). The mutant detection probe was complementary to the coding sequence, containing an A base at nucleotide position +476. The reference detection probe was complementary to the coding sequence, containing a G base at nucleotide position +476. Two flanking primers were designed to amplify the genomic sequence surrounding nucleotide +476 in the coding sequence. The assay was designed using BioRads Droplet Digital PCR Assays design tool for mutation detection. The following primers and probes were developed for the specific ScFDC1 locus:

```
target specific forward primer
                                   (SEQ ID NO: 13)
(5'-CATGTTTCAGACGGTGG-3')

target specific reverse primer
                                   (SEQ ID NO: 14)
(5'-CATACCTCTAGCAATTGACC-3')

mutant detection probe
                                   (SEQ ID NO: 15)
(5'-ACGTACGGAATGTAGATTCT-3')-labelled
with 6-carboxyfluorescein-FAM reference detection probe
                                   (SEQ ID NO: 16)
(5'-ACGTACGGAATGTGGATT-3')-labelled
with hexachlorofluorescein-HEX.
```

The next step, in general, was to determine whether the library contained mutated yeast strains. The screening was performed with a total of 96 yeast library pools, each comprising 1200-1500 mutagenized yeast colonies and representing a total of approximately 120,000-150,000 mutated yeast strains. The ddPCR was performed essentially as described in Example 7. 5-µL gDNA samples of gDNA of 96 pools of mutagenized yeast strains were added to each well of a microtiter plate containing 17 µl of the PCR reaction mixture and mixed thoroughly by pipetting up and down.

The microtiter plate for PCR was loaded onto the QX200 Droplet Reader (Bio-Rad) for droplet analysis. The data obtained was analyzed using the software QuantaSoft (version v1.7, Bio-Rad). The threshold was determined using the 2-D plot, set at 2700 and 1500 for amplification for Channel 1 and Channel 2 amplitude, respectively. Comparison of the individual values for fractional abundance showed that the gDNA with plate coordinates G01 provided a higher signal than any other sample with respect to mutant detection. The fractional abundance of gDNA pool G01 was 0.190% compared to 0.030%, the latter representing the average fractional abundance of all of the 96 tested gDNA samples.

WS4: Identifying Individual Yeast Clones Carrying a Selected Scfdc1 Mutation by Creating Subsequent Sub-Pools.

Step 4.1: Creating 100Er Sub-Pools from the FS0105 Total Random Library.

Based on the analysis of 96 gDNA library pool samples analyzed with a ScFDC1-specific ddPCR assay, it was considered highly likely that the 1,200-1,500 yeast strains in pool G01 would contain one or more individual clones carrying the gene mutation of interest.

The cell titer of the positive library pool G01 identified in Step 3.2 was determined by plating respective dilutions on YPD agar plates. Subsequently, 48 15 ml culture tubes containing 3 ml liquid YPD medium were inoculated with approx. 100 cells each from the library pool G01. Culture tubes were incubated for three days on a rotary incubator at 30° C. resulting in 48 100er sub-pools from the library G01 representing approx. 4800 individual clones from library pool G01.

Step 4.2: Yeast Genomic DNA Isolation from FS0105 100Er Sub-Pools.

Genomic DNA was isolated from each of the 48 100er sub-pools (see previous step) according to Step 3.1, and the final concentration was again adjusted to a of about 5 ng gDNA/µl.

Step 4.3: Analysis of the 100Er Sub-Pool gDNA Samples by ddPCR.

gDNA derived from the 48 100er sub-pools, containing approx. 100 colonies each from pool G01, were analyzed as described above (see Step 3.2). The data were analyzed using the software QuantaSoft (version v1.7, Bio-Rad). The threshold was determined using the 2-D plot and set at 2000 for Channel 1 amplitude and 2500 for Channel 2 amplitude. Four individual wells in the microtiter plate (G07, C08, C09, G10) were identified that showed a fractional abundance above 1%, indicating the presence of at least 1 mutated colony in a specific pool of 100 colonies.

Step 4.4: Creating 10Er Sub-Pools from the FS0105 Total Random Library.

100er sub-pool C09 showed the highest fractional abundance in the ddPCR analyses (2.99%) and was selected for further analyses.

Similar to Step 4.1, the cell titer of the positive 100er sub-pool C09 identified in Step 3.2 was determined by plating respective dilutions on YPD agar plates. Subsequently, 24 15 ml culture tubes containing 3 ml liquid YPD medium were inoculated with approx. 10 cells each from the 100er sub-pool 009. Culture tubes were incubated for three days on a rotary incubator at 30° C. resulting in 24 100er sub-pools from the library C09 representing approx. 240 individual clones from the 100er sub-pool G01.

Step 4.5: Yeast Genomic DNA Isolation from FS0105 100Er Sub-Pools.

Genomic DNA was isolated from each of the 24 10er sub-pools (see Step 4.4) according to Step 3.1, and the final concentration was again adjusted to a of about 5 ng gDNA/µl.

Step 4.6: Analysis of the 10Er Sub-Pool gDNA Samples by ddPCR.

The gDNA derived from 24 individual 10er sub-pools was analyzed as described above. The data was analyzed as described above (see Step 3.2) using the software QuantaSoft (version v1.7, Bio-Rad). The threshold was determined using the 2-D plot and set at 1500 for Channel 1 amplitude and 2000 for Channel 2 amplitude. Three individual pools (A02, C03 and D03) showed a fractional abundance above 10%, confirming the presence of at least one mutated colony in each of the three pools of 10 colonies.

Step 4.7: Identifying Individual Clones from the FS0105 10Er Sub-Pools Carrying the Introduced Mutation of Interest.

The 10er sub-pool D03 showing the highest fractional abundance in the ddPCR analysis (Step 4.6) was selected for further analysis. gDNA was isolated from 16 individual yeast colonies derived from 10er sub-pool D03 and subjected to the same analysis as described above (see Step 4.3 and 4.6). The data were analyzed using the software QuantaSoft (version v1.7, Bio-Rad). The threshold was determined using the 2-D plot and set at 2000 for Channel 1 amplitude and 2500 for Channel 2 amplitude. Two individual pools (C02 and D02) showed a fractional abundance above 99.9%, confirming the presence of two mutated yeast colonies among 16 tested individual colonies.

Step 4.8: Isolation of the Mutant Yeast Pure Culture.

Strain FS0105 shows the tendency to form larger cell aggregates. To assure that the future stock of the mutant yeast of interest was derived from a single cell and not a clump of cells, we used a Singer MSM 400 Dissecting Microscope to isolate single cells from the two individual pools C02 and D02. To this extent, the cell suspensions from the individual pools were diluted 1000 fold in TE buffer, which supports the release of certain cell clumps, and 10 µl of the dilution was spotted onto a complex medium agar plate. Single cells were then isolated according to the manufacturers recommendations/manual.

Step 4.9: Confirming the Selected Mutation of Interest by DNA Sequence Analyses.

Genomic DNA from the single cell isolates from Step 4.8 was isolated using a standard yeast genomic DNA preparation protocol, and the region covering the target gene ScFDC1 was amplified by standard PCR techniques using ScFDC1 specific oligonucleotides. The resulting DNA fragments were cleaned using the Wizard® SV Gel and PCR Clean-up System (Promega) and sequenced (LGC Genomics) for the area around the nucleotide of interest (+476 of ScFDC1). The analysis of the recovered DNA sequences showed that both single cell clones that derived from the individual pools C02 and D03 (see 4.7 and 4.8) contained the desired nonsense mutation W159* caused by a G to A transition at nucleotide +476 of the ScFDC1 gene.

Example 22

A wheat plant carrying a specific mutation was identified using the methods described in the Workstreams and Examples herein above. The naming of the various pools etc. was done using the naming shown in FIG. 2. Whereas barley is a self-pollinating, diploid species with 14 chromosomes, polyploidy is common in wheat. The present Example demonstrates that the methods of the invention can be used even with a polyploid organism, such as wheat. As described, the methods can be used for identification of any mutant. The present example describes identification of a specific mutation (guanine to adenine) leading to the exchange of amino acid tryptophan to a translational stop in the codon region of wheat gene GASR7 on the A-genome (TaGASR7-A1) at position 91. The sequence of the GASR7-A1 gene is available at GenBank under number NCBI: KJ000052, the cDNA sequence is provided herein as SEQ ID NO:25 and the amino acid sequence of GASR7 is provided as SEQ ID NO:8.

ddPCR Assay

A specific ddPCR assay was designed, which specifically distinguishes between the mutant allele and wild type allele of TaGASR7-A1 at nucleotide position 273 in the wild type coding sequence (GenBank number NCBI: KJ000052). The mutant detection probe was complement to the coding sequence containing an adenine at nucleotide position 273. The reference detection probe was complement to the coding sequence containing a guanine at nucleotide position 273. Two flanking primers were designed to amplify the genomic sequence surrounding nucleotide 273 in the coding sequence. The following primers and probes were developed for the specific TaGASR7-A1 locus:

```
target specific forward primer
                                    (SEQ ID NO: 9)
(5'-CGCCTGCCCCTGCTA-3')

target specific reverse primer
                                    (SEQ ID NO: 10)
(5'-AGAAGAAGAAGAAGAAGAAGAAAACCAAGAA-3')

mutant detection probe
                                    (SEQ ID NO: 11)
(5'-CAACAACTGAAAGACCA-3')-labelled
with 6-carboxyfluorescein-FAM reference detection probe
                                    (SEQ ID NO: 12)
(5'-CAACAACTGGAAGACCA-3')-labelled
with fluorophore VIC
```

A pool of randomly mutagenized wheat grains was prepared by soaking grains in 0.6% EMS for 17 hours. Afterwards grains were rinsed with water and dried on filter paper for 45 minutes. Mutagenized grains were planted immediately after the drying.

WS3: Determining Whether a Library Sample Contains Mutated Grains

It was then determined whether the library contained mutated grains, essentially as described in WS3 and Example 7 herein above with the following specifics:

The screening was performed on a total of 94 GLPs (94 sub pools), representing approximately 30.000 mutated wheat plants. The ddPCR was performed essentially as described in Example 7.

One 5-µl gDNA sample derived from gDNA (GT #10001-GT #10094) was added to each well containing 17-µl of the PCR reaction mixture and mixed thoroughly by pipetting up and down.

The PCR plate was loaded onto the QX200 Droplet Reader (Bio-Rad Laboratories) for droplet analysis. The data was analysed using the software QuantaSoft (version v1.7, Bio-Rad Laboratories). The threshold was determined using the 2-D plot and set at 3000 for Channel 1 amplitude and 2000 for Channel 2 amplitude. Comparison of the individual values for fractional abundance showed that gDNA (GT #10072) contained more signal derived from the mutant detection than any other sample. The fractional abundance of gDNA (GT #10072) was 0.130% compared to 0.024% which represents the average fractional abundance of all 94 tested gDNA samples.

WS4: Finding Individual Grain(s) Characterized by a Mutation of Interest

Individual wheat grains carrying the mutation were identified essentially as described herein above in WS4 with the following specifics:

Based on analysis of gDNA of subpools (GT #10001-GT #10094) with a TaGASR7-A1 specific ddPCR assay, it was considered highly likely that the 4500 grains of GLP #10072 (corresponding to positive sample gDNA (GT #10072)) would comprise one or more grains with the identical mutation of interest.

FGLP #10072 was established by sequentially removing 96 samples of 10 grains each from GLP #10072. Each 10-grain aliquot was placed on a piece of weighing paper, and then consecutively fixed with a pair of forceps while an engraving machine (Marathon-3, Saeyang Microtech) equipped with a 1.6-mm drill was used to drill a small, 2-3 mm deep hole into the endosperm. The rotating movement moved flour from the endosperm onto the top of the grain and the surrounding weighing paper. The 10-grain drilled samples were placed in separate 2-ml wells of a microtiter plate, yielding the secondary sub-pool of drilled wheat grains PDGLP #10072. The 96 flour samples, each with flour derived from 10 drilled wheat grains were transferred to separate wells of a 1.5-ml microtitre plate (PFGLP #10072) keeping a sample numbering system matching that of the drilled grains.

PFGLP #10072 was subjected to extraction of gDNA using a semi-automated DNA extraction procedure as detailed in the instructions of the NucleoSpin 96 Plant II kit (Macherey-Nagel). Accordingly, each well of the microtitre plate contained gDNA from flour of 10 grains.

DNA derived from PFGLP #10072 was analysed as described above. The data was analysed using the software QuantaSoft (version v1.7, Bio-Rad Laboratories). The threshold was determined using the 2-D plot and set at 2500 for Channel 1 amplitude and 1700 for Channel 2 amplitude. Two individual wells in the microtitre plate (B10 and G05) were identified that showed a fractional abundance of 7.6% and 5.2%, all indicating the presence of two individual mutants in 2 independent wells of PDGLP #10072.

All 10 grains from well B10 of PDGLP #10072 were germinated. Leaf material from all 10 plantlets was harvested and subjected to DNA extraction using REDExtract (Sigma Aldrich). The gDNA derived from leaf samples was analysed as described above. The data was analysed using the software QuantaSoft (version v1.7, Bio-Rad Laboratories). The threshold was determined using the 2-D plot and set at 2000 for Channel 1 amplitude and 1600 for Channel 2 amplitude. One plantlet derived from well C03 of PDGLP #10072 showed a fractional abundance of 99%, confirming the presence of a homozygous mutant.

Additional trait verification was performed using direct sequencing on the identified mutant and a reference sample. DNA was extracted from leaf material using the REDExtract DNA extraction procedure (Sigma Aldrich). For the sequencing analysis a 50-µl PCR reaction was prepared that contained 1-µl of purified gDNA, 20-µl REDExtract (Sigma Aldrich), 500 nM of a target specific forward primer, 500 nM of a target specific reverse primer and water. The samples were thermally cycled using the following PCR conditions: denaturation at 94° C. for 2 min, 38 cycles of PCR at 94° C. for 45 sec, 58° C. for 45 sec and 72° C. for 45 sec, and a final extension at 72° C. for 5 min before storage of the PCR plate at 8° C. Individual PCR products were purified using the NucleoSpin Gel and PCR clean up kit. All samples were sequenced using a target specific forward primer and a target specific reverse primer.

The plantlet that was positive for the mutation in the ddPCR analysis also showed a heterozygous mutant genotype at the predetermined genomic location. The reference sample showed a homozygous wild type genotype at the same location.

Example 23

A barley plant carrying a specific mutation was identified by the combined use of two technologies, of which one was provided by Rain Dance Technologies and the other by Bio-Rad Laboratories. In general terms, the RainDance technology was utilized to identify specific, yet complex samples that contain gDNA templates from numerous mutant grains, while subsequent BioRad-based analyses helped to identify single grains characterized by the mutation of interest. The naming of the various pools etc. was done using the naming shown in FIG. 2.

As described, the methods can be used for identification of any mutant. The present Example describes the identification of a specific mutation (guanine to adenine) leading to the exchange of amino acid tryptophan to a translational stop in the codon region of a barley gene encoding a putative BAHD acyltransferase (HvBADH1) at position 31.

ddPCR Assay

A specific ddPCR assay was designed, which specifically distinguishes between the mutant allele and wild type allele of HvBADH1 at nucleotide position 93. The wild type coding sequence (cDNA sequence) is provided herein as SEQ ID NO:17 and the mutant coding sequence is provided herein as SEQ ID NO:18. The amino acid sequence of HvBADH1 is provided as SEQ ID NO:19. The mutant detection probe was complementary to part of the coding sequence containing an adenine at nucleotide position 93 of SEQ ID NO:17. The reference detection probe was complementary to part the coding sequence containing a guanine at nucleotide position 93. Two flanking primers were designed to amplify the genomic sequence surrounding nucleotide 93 in the coding sequence. Additionally a blocking probe was developed, using the nucleotide sequence of the reference detection probe, supplemented with a 3' spacer, which prevents extension of the reference sequencing, by DNA polymerases during PCR. The following primers and probes were developed for the specific HvBADH1 locus:

```
target specific forward primer
                                    (SEQ ID NO: 20)
(5'-CCCGACCACACGC-3')

target specific reverse primer
                                    (SEQ ID NO: 21)
(5'-ACTCCACCAGGCCG-3')

mutant detection probe
                                    (SEQ ID NO: 22)
(5'-CTGGCGTGAGTGGAC-3')-labelled
with 6-carboxyfluorescein-FAM reference detection probe
                                    (SEQ ID NO: 23)
(5'-CTGGCGTGGGTGGA-3')-labelled
with tetrachlorofluorescein-TET blocking probe
                                    (SEQ ID NO: 24)
(5'-CTGGCGTGGGTGGA-3')-labelled
with a 2',3'-dideoxyC spacer
```

Preparing "Super-Pools" of gDNA.

Simply, 50 µl of each gDNA extract of all 94 "Aliquots of individual sub flour totals (ASFTs)" represented on one 96 well plate, were pooled into one "Super-pool."

Determining Whether a 'Super-Pool' Contains Mutated Grains

It was then determined whether a 'Super-pool', comprising DNA from 94 ASFTs contained mutated grains, essentially as described in Example 17 herein above with the following specifics:

Firstly, 2 µl of gDNA from a super-pool was added to a 50-0 enrichment and blocking PCR containing 10 µl 5×Q5 Reaction Buffer (New England Biolabs), 200 µM dNTPs, 0.02 U/µl Q5 High-Fidelity DNA Polymerase, 100 nM of target-specific forward PCR primer, 100 nM of target-specific reverse PCR primer, 100 nM blocking probe (2',3'-dideoxyC spacer) and water. The PCR mixture was thermally cycled using standard PCR conditions: denaturing at 98° C. for 2 min, 20 cycles of PCR at 98° C. for 10 sec, 57° C. for 20 sec and 72° C. for 10 sec, and a final extension at 72° C. for 5 min before storage at 8° C.

Secondly, droplets for 4 individually enriched and blocked "Super-pools" were generated using the RainDrop Source instrument. A 10-µl aliquot of enriched and blocked PCR product from each "Super-pool" was individually combined with 25 µl Supermix for Probes (Bio-Rad); 1× Droplet Stabilizer (RainDance); 900 nM of the target-specific forward primer; 900 nM of the target specific reverse primer; 120 nM of the reference detection probe (TET); 440 nM of the mutant detection probe (FAM), and; H₂O for adjustment to a total reaction volume of 50 µl. A total of 4 individual reaction mixtures, representing 4 individual "Super-pools" of gDNAs, were added to the source chip (RainDance), and processed on the Source Instrument (RainDance).

The 8-well PCR strip containing the droplets generated from the reaction mixtures by the Source Instrument (RainDance), described herein above, were sealed and thermally cycled using standard PCR conditions: denaturing at 95° C. for 10 min, 40 cycles of PCR at 95° C. for 15 sec, 55° C. for 1 min, and a final extension at 98° C. for 10 min before storage at 8° C. Thereafter, the amplified mixtures were transferred to the Sense Instrument (RainDance), and analyzed using the RainDrop Analyst data analysis software.

The average fractional abundance of 4 super-pools was 0.0115%. Super-pool SP-gDNA #05 had a fractional abundance of 0.0228%, indicating a high probability that this super-pool contains DNA from mutant grains.

Determining Whether a Library Sample Contains Mutated Grains

It was then determined whether the plate of 94 ASFTs corresponding to SP-gDNA #05 contained mutated grains, essentially as described in Example 7 herein above with the following specifics:

The screening was performed on a total of 94 SGTs (sub grain totals), representing approximately 30.000 mutated barley plants. The gDNA used for this part of the screening was the gDNA purified from the ASFT—i.e. DNA, which had not been enriched. For analytical purposes, 5 µl of purified gDNA derived from gDNA (GT #377-GT #470) was added to a 17-0 PCR mixture containing 11 µl 2× ddPCR Supermix for probes (No. dUTP; Bio-Rad Laboratories), 900 nM target-specific PCR primers primer, 250 nM mutant detection probe (6-carboxyfluorescein—FAM) and wild-type detection probe (tetrachlorofluorescein—TET) probes. The reaction mixture was loaded onto the AutoDG Droplet Generator (Bio-Rad) and droplet generation carried out according to the manufacturer's manual. The droplet emulsion was thermally cycled using standard PCR conditions: denaturing at 95° C. for 10 min, 40 cycles of PCR at 94° C. for 30 sec and 55° C. for 1 min, and a final extension at 98° C. for 10 min before storage of the microtitre plate at 8° C. PCR amplification in droplets was confirmed using the QX200 Droplet Reader (Bio-Rad Laboratories).

The PCR plate was loaded onto the QX200 Droplet Reader (Bio-Rad Laboratories) for droplet analysis. The data was analysed using the software QuantaSoft (version v1.7, Bio-Rad Laboratories). The threshold was determined using the 2-D plot and set at 2200 for Channel 1 amplitude and 2700 for Channel 2 amplitude. Comparison of the individual values for fractional abundance showed that gDNA (GT #416) contained more signal derived from the mutant detection than any other sample. The fractional abundance of gDNA (GT #416) was 0.4% compared to 0.073% which represents the average fractional abundance of all 94 tested gDNA samples.

Finding Individual Grain(s) Characterized by a Mutation of Interest

Individual barley grains carrying the mutation were identified essentially as described herein above in Examples 9 to 15 with the following specifics: Based on analysis of gDNA (GT #416) with a HvBADH1 specific ddPCR assay, it was considered highly likely that the 4500 grains of GLP #416 (corresponding to positive sample gDNA (GT #416)) would comprise one or more grains with the identical mutation of interest.

FGLP #416 was established by sequentially removing 96 samples of 12 grains each from GLP #416. Each 12-grain aliquot was placed on a piece of weighing paper, and then consecutively fixed with a pair of forceps while an engraving machine (Marathon-3, Saeyang Microtech) equipped with a 1.6-mm drill was used to drill a small, 2-3 mm deep hole into the endosperm. The rotating movement moved flour from the endosperm onto the top of the grain and the surrounding weighing paper. The 10-grain drilled samples were placed in separate 2-ml wells of a microtiter plate, yielding the secondary sub-pool of drilled barley grains PDGLP #416. The 96 flour samples, each with flour derived from 12 drilled barley grains were transferred to separate wells of a 1.5-ml microtitre plate (PFGLP #416) keeping a sample numbering system matching that of the drilled grains.

PFGLP #416 was subjected to extraction of gDNA using a semi-automated DNA extraction procedure as detailed in the instructions of the NucleoSpin 96 Plant II kit (Macherey-Nagel). Accordingly, each well of the microtitre plate contained gDNA from flour of 12 grains.

DNA derived from PFGLP #416 was analysed using the same PCR mixture and PCR reaction conditions as described above (Determining whether a library sample contains mutated grains). The data was analysed using the software QuantaSoft (version v1.7, Bio-Rad Laboratories). The threshold was determined using the 2-D plot and set at 3000 for Channel 1 amplitude and 2500 for Channel 2 amplitude. Two individual wells in the microtitre plate (D10 and F02) were identified that showed a fractional abundance of 3.4% and 13.7%, indicating the presence of two individual mutants in 2 independent wells of PDGLP #416.

All 12 grains from well F02 of PDGLP #416 were germinated. Leaf material from all 12 plantlets was harvested and subjected to DNA extraction using REDExtract (Sigma Aldrich). The gDNA derived from leaf samples was analysed using the same PCR mixture and PCR reaction conditions as described above (Determining whether a library sample contains mutated grains). The data was analysed using the software QuantaSoft (version v1.7, Bio-Rad Laboratories). The threshold was determined using the 2-D plot and set at 5000 for Channel 1 amplitude and 3200 for Channel 2 amplitude. One plantlet derived from well F02 of PDGLP #416 showed a fractional abundance of 39%, confirming the presence of a heterozygous mutant.

REFERENCES

Andrew J. Goodall, Pankaj Kumar and Alyson K. Tobin (2013). Identification and expression analyses of cytosolic glutamine synthetase genes in barley (*Hordeum vulgare* L.). Plant Cell Physiol. 54: 492-505.

Botticella, E., Sestili, F., Hernandez-Lopez, A., Phillips, A., & Lafiandra, D. (2011). High resolution melting analysis for the detection of EMS induced mutations in wheat Sbella genes. BMC Plant Biology 11: 156.

Inoue, H., Nojima, H. and Okayama, H., (1990). High efficiency transformation of *Escherichia coli* with plasmids. Gene 96, 23-28.

Jiang, F. et al. (2016). Structures of a CRISPR-Cas9 R-loop complex primed for DNA cleavage. Science 351: 867-871.

Pleasance, et al. (2010). A comprehensive catalogue of somatic mutations from a human cancer genome. Nature 463: 191-196.

Schuster-Böchler, B. and Lehner, B. (2012). Chromatin organization is a major influence on regional mutation rates in human cancer cells. Nature 488: 504-507.

Yamaya, T. and Kusano, M. (2014). Evidence supporting distinct functions of three cytosolic glutamine synthetases and two NADH-glutamate synthases in rice. J. Exp. Bot. 65: 5519-5525.

Wellner, V. P. and Meister, A. (1966). Binding of Adenosine Triphosphate and Adenosine Diphosphate by Glutamine Synthetase. Biochemistry 5: 872-879.

The invention claimed is:

1. A method of identifying an organism of a predefined species carrying one or more predetermined mutations in one or more nucleotides of interest (NOIs) in a target sequence, wherein the predetermined mutation is a deletion or substitution of one or more NOIs, said method comprising the steps of:

a) Subjecting the organisms of said species, or reproductive parts thereof, to random mutagenesis, thereby providing a pool of organisms from said species or reproductive parts thereof, representing a plurality of genotypes;

b) Dividing said pool into one or more sub-pools of organisms or reproductive parts thereof;

c) Preparing genomic DNA (gDNA) samples, each sample comprising gDNA from each genotype within a sub-pool, while maintaining the potential for multiplication of organisms of each genotype within said sub-pool;

d) Performing a plurality of PCR amplifications, each comprising (i) the gDNA sample from one sub-pool, (ii) one or more sets of primers, each set flanking one or more target sequences in the gDNA sample, and (iii) PCR reagents; thereby amplifying the one or more target sequences, wherein each PCR amplification comprises a plurality of compartmentalized PCR amplifications, each compartmentalized PCR amplification comprising part of said gDNA sample;

e) Detecting one or more PCR amplification products from (d), the one or more amplification products comprising one or more target sequences comprising the one or more predetermined mutations in the one or more NOIs, thereby identifying one or more sub-pools that comprise said one or more predetermined mutations;

f) Dividing the organisms or reproductive parts thereof of the one or more identified sub-pools of (e) into secondary sub-pools;

g) Preparing gDNA samples, each comprising gDNA from each genotype within a secondary sub-pool, while maintaining the potential for multiplication of organisms of each genotype within said secondary sub-pool;

h) Performing a plurality of PCR amplifications, each comprising (i) the gDNA sample from one secondary sub-pool, (ii) one or more sets of primers, each set flanking one or more target sequences in the gDNA sample, and (iii) PCR reagents, thereby amplifying the one or more target sequences;

i) Detecting PCR amplification products from (h) that comprise one or more target sequences comprising the one or more predetermined mutations in the one or more NOIs, thereby identifying one or more secondary sub-pools that comprise said one or more mutations; and j) Identifying an organism or reproductive part thereof within one or more secondary sub-pools that carries said one or more predetermined mutations, wherein the pool comprises at least 100,000 organisms or reproductive parts thereof; or wherein each sub-pool comprises at least 100 organisms or reproductive parts thereof with different genotypes.

2. The method according to claim 1, wherein the PCR amplifications of step d) are performed by a method comprising the following steps:
Preparing one or more PCR amplifications comprising (i) the gDNA sample, (ii) the one or more sets of primers, each set flanking a target sequence, and (iii) the PCR reagents;
Partitioning said one or more PCR amplifications into a plurality of spatially separated compartments for performing compartmentalized PCR amplifications;
Performing PCR amplifications in the spatially separated compartments; and
Detecting PCR amplification products from the PCR amplifications.

3. The method according to claim 2, wherein said spatially separated compartments are droplets.

4. The method according to claim 1, wherein each PCR amplification is compartmentalized into a range of 1000 to 100,000 spatially separated compartments.

5. The method according to claim 1, wherein the method further comprises a step of reproducing the organisms or the reproductive parts thereof within the pool, and wherein the reproducing step is performed simultaneously with or subsequent to step b) of dividing the pool into one or more sub-pools.

6. The method according to claim 1, wherein the species is a plant, and wherein steps a) and b) of said method, taken together, comprise:
Providing a plurality of seeds of the plant;
Subjecting said seeds to random mutagenesis, thereby obtaining seeds of generation M0;
Growing said seeds of generation M0 into mature plants, and obtaining seeds from said mature plants, wherein said seeds are seeds of generation M1;
Optionally repeating the previous step at least once, to obtain plants comprising seeds of generation M(1+X), where X is the number of times the previous step is repeated;
Obtaining seeds of either generation M1 or M(1+X) from said mature plants, thereby obtaining a pool of seeds; and
Dividing said pool of seeds into one or more sub-pools, wherein all seeds from a given mature plant are placed into the same sub-pool.

7. The method according to claim 6, wherein at least 500,000 seeds are provided.

8. The method according to claim 1, wherein the species is a unicellular organism, and steps a) and b) of the method, taken together, comprise:
Providing a plurality of unicellular organisms;
Subjecting said organisms to random mutagenesis;
Dividing the mutagenized organisms into one or more sub-pools; and
Subjecting each sub-pool to reproduction.

9. The method according to claim 1, wherein the species is a unicellular species, and step f) of the method comprises:
Providing a sub-pool of unicellular organisms comprising the one or more predetermined mutations in the one or more NOIs;
Reproducing some or all of the organisms of said sub-pool in a clonal manner to obtain clonal cultures; and
Combining a fraction of organisms from a plurality of said clonal cultures to obtain secondary sub-pools.

10. The method according to claim 1, wherein the species is a plant, and steps f) and g), taken together, comprise:
Providing a sub-pool comprising a plurality of seeds of the plant, wherein said sub-pool comprises one or more mutations in one or more NOIs;
Dividing the seeds of said sub-pool into secondary sub-pools, each comprising 1 to 100 seeds;
Obtaining a sample from each seed of the secondary sub-pools, in a manner that leaves the seeds sufficiently intact to be capable of developing into a plant;
Combining all samples from all seeds of each secondary sub-pool; and
Preparing a gDNA sample from said combined samples.

11. The method according to claim 10, wherein said sample from each seed is obtained by drilling a hole into the seed followed by collecting flour from the seed.

12. The method according to claim 1, wherein the method further comprises a step of identifying a super-pool comprising one or more mutations in the one or more NOIs, wherein the super-pool is a group of sub-pools.

13. The method according to claim 12, comprising:
Following step c), obtaining a fraction of each gDNA sample from each sub-pool; and
Combining a plurality of fractions into super-pools, thereby obtaining gDNA sample super-pools comprising gDNA samples from a plurality of sub-pools, wherein gDNA from each sub-pool is only present in one super-pool; and
wherein steps d) and e) comprise:
Performing a plurality of PCR amplifications, each amplification comprising (i) a gDNA sample super-pool, (ii) one or more sets of primers, each set flanking a target sequence, and (iii) PCR reagents; thereby amplifying one or more target sequences, wherein each PCR amplification comprises a plurality of compartmentalised PCR amplifications, each comprising part of said gDNA sample super-pool; and Detecting PCR amplification products comprising one or more target sequences comprising the one or more predetermined mutations in the one or more NOIs, thereby identifying one or more super-pools that comprise said one or more predetermined mutations.

14. The method according to claim 1, wherein the species is a unicellular organism.

15. The method according to claim 1, wherein the species is a plant.

16. The method according to claim 1, wherein the species is a cereal.

17. The method according to claim 1, wherein the one or more predetermined mutations comprise a substitution of a single nucleotide.

18. The method according to claim 1, wherein the method identifies more than one predetermined mutation.

19. A method of identifying a sub-pool of organisms from a predefined species or reproductive parts thereof, wherein the sub-pool comprises an organism with one or more predetermined mutations in one or more nucleotides of interest (NOI) in a target sequence, wherein the predetermined mutation is a deletion or substitution of one or more NOIs, said method comprising the steps of:
   a) Subjecting the organisms of said species, or reproductive parts thereof, to random mutagenesis, thereby providing a pool of organisms from said species or reproductive parts thereof, the pool representing a plurality of genotypes;
   b) Dividing said pool into one or more sub-pools of organisms or reproductive parts thereof, wherein each sub-pool comprises more than one individual organism or reproductive part thereof of each genotype, wherein all progeny of one organism or reproductive part thereof from said pool are comprised within one sub-pool;
   c) Randomly dividing the one or more sub-pools into parts such that each part is intended to comprise organisms or reproductive parts thereof representing each genotype of the sub-pool;
   d) Preparing genomic DNA (gDNA) samples from one of said parts and storing the remainder of organisms or reproductive parts thereof under conditions maintaining the reproductive potential;
   e) Performing a plurality of PCR amplifications, each amplification comprising the gDNA sample from the parts of one sub-pool, and further comprising one or more sets of primers, wherein each set of primers flanks a target sequence, and PCR reagents, thereby amplifying one or more target sequences; and
   f) Detecting one or more PCR amplification products comprising one or more target sequences, said one or more target sequences comprising the one or more mutations in the one or more NOI, thereby identifying one or more sub-pools comprising said one or more mutations,
   wherein the pool comprises at least 100,000 organisms or reproductive parts thereof; or
   wherein each sub-pool comprises at least 100 organisms or reproductive parts thereof with different genotypes.

20. A method of identifying a sub-pool of plants of a predefined plant species or reproductive parts thereof, wherein the sub-pool comprises a plant carrying one or more predetermined mutations in one or more nucleotides of interest (NOI) in a target sequence, wherein the predetermined mutation is a deletion or substitution of one or more NOIs, said method comprising the steps of:
   a) Providing a plurality of reproductive parts of the plant species, the plurality comprising at least 100 reproductive parts with different genotypes;
   b) Subjecting said reproductive parts to random mutagenesis, thereby obtaining reproductive parts of generation M0;
   c) Growing said reproductive parts of generation M0 into mature plants and obtaining reproductive parts from said mature plants, wherein said reproductive parts are reproductive parts of generation M1;
   d) Obtaining reproductive parts of generation M1 from said mature plants, thereby obtaining a pool of reproductive parts;
   e) Dividing said pool of reproductive parts of generation M1 into sub-pools, wherein all reproductive parts from a given mature M0 plant are placed into the same sub-pool, wherein each sub-pool comprises a plurality of genotypes;
   f) Preparing genomic DNA (gDNA) samples, each sample comprising gDNA from each genotype within a sub-pool, while maintaining the potential for multiplication of plants of each genotype within said sub-pool;
   g) Performing a plurality of PCR amplifications, each comprising a gDNA sample from one sub-pool, one or more sets of primers, wherein each set of primers flanks a target sequence, and PCR reagents, thereby amplifying one or more target sequences;
   h) Detecting one or more PCR amplification products comprising one or more target sequences, said one or more target sequences comprising the one or more mutations in the one or more NOI, thereby identifying one or more sub-pools comprising said one or more mutations,
   wherein the pool obtained in step (d) comprises at least 100,000 reproductive parts; or
   wherein each sub-pool obtained in step (e) comprises at least 100 reproductive parts with different genotypes.

21. The method of claim 1, wherein the pool comprises at least 100,000 organisms or reproductive parts thereof.

22. The method of claim 1, wherein the pool comprises at least 100,000 organisms or reproductive parts thereof and wherein each sub-pool comprises at least 100 organisms or reproductive parts thereof with different genotypes.

* * * * *